(12) United States Patent
Ungi et al.

(10) Patent No.: US 12,274,507 B2
(45) Date of Patent: Apr. 15, 2025

(54) SYSTEM AND METHOD FOR PROVIDING SURGICAL PLANNING AND GUIDANCE WITH THREE-DIMENSIONAL VISUALIZATION

(71) Applicant: Medical Robotic Research, LLC, Wilmington, DE (US)

(72) Inventors: Tamas Ungi, Kingston (CA); Paul St. John, Kingston (CA)

(73) Assignee: Medical Robotoic Research, LLC, Wilmington, DE (US)

( * ) Notice: Subject to any disclaimer, the term of this patent is extended or adjusted under 35 U.S.C. 154(b) by 501 days.

(21) Appl. No.: 17/541,965

(22) Filed: Dec. 3, 2021

(65) Prior Publication Data
US 2022/0175455 A1    Jun. 9, 2022

Related U.S. Application Data

(60) Provisional application No. 63/121,029, filed on Dec. 3, 2020.

(51) Int. Cl.
| | |
|---|---|
| *A61B 34/10* | (2016.01) |
| *A61F 2/46* | (2006.01) |
| *G06T 5/70* | (2024.01) |
| *G06T 7/33* | (2017.01) |
| *G06T 7/73* | (2017.01) |
| *G16H 20/40* | (2018.01) |
| *G16H 30/40* | (2018.01) |

(52) U.S. Cl.
CPC ............ *A61B 34/10* (2016.02); *A61F 2/46* (2013.01); *G06T 5/70* (2024.01); *G06T 7/33* (2017.01); *G06T 7/73* (2017.01); *G16H 20/40* (2018.01); *G16H 30/40* (2018.01); *A61B 2034/104* (2016.02); *A61B 2034/105* (2016.02); *A61B 2034/108* (2016.02); *A61F 2002/4633* (2013.01); *G06T 2200/24* (2013.01); *G06T 2207/20084* (2013.01); *G06T 2207/30008* (2013.01); *G06T 2207/30052* (2013.01)

(58) Field of Classification Search
None
See application file for complete search history.

(56) References Cited

U.S. PATENT DOCUMENTS

2020/0275976 A1*    9/2020   McKinnon .............. A61B 90/37

\* cited by examiner

*Primary Examiner* — Leon Flores
(74) *Attorney, Agent, or Firm* — Greenberg Traurig, LLP; Mammen P. Zachariah ("Roy")

(57) ABSTRACT

A system for providing surgical planning and guidance with three-dimensional visualization is disclosed. In particular, the system obtains an image set of an anatomy of interest of a subject, and renders the image set on a user interface using volume rendering. Notably, the system accomplishes the foregoing without generating surface models or conducting bone contouring. The system may, during generation of an implant plan for implanting an implant onto the anatomy of interest, suggest landmark points in the volume rendered image set. Once the landmark points are confirmed, the system may facilitate implant positioning via implant controls. The system conducts a registration process to confirm a match between the physical anatomy of interest and the information contained in volume-rendered image set in the plan. If there is a match, the system may facilitate performance of a surgical procedure for implanting the implant onto the anatomy of interest of the subject.

20 Claims, 108 Drawing Sheets
(49 of 108 Drawing Sheet(s) Filed in Color)

| ICON | NAME | PURPOSE |
|---|---|---|
| 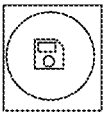 | SAVE | SAVES THE CURRENT PLAN, OVERWRITING PREVIOUS VERSION. |
| 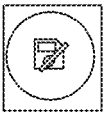 | SAVE AS | SAVES CURRENT PLAN TO A NEW FILE. |
| 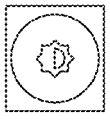 | WINDOWING | ALLOWS USING THE MOUSE TO ADJUST CONTRAST AND BRIGHTNESS. |
| 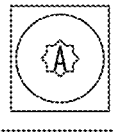 | AUTO WINDOWING | AUTOMATICALLY CHOOSE A CONTRAST AND BRIGHTNESS FOR IMAGES. |
| 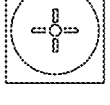 | SLICE INTERSECTION | SHOWS ORTHOGONAL IMAGES AS COLOR COORDINATED SLICE INTERSECTIONS. |
| 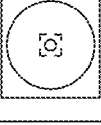 | SYNC SLICES | SYNCHRONIZES 2D IMAGE VIEWS IF MOUSE IS MOVED WITH LEFT BUTTON PRESSED. |
| 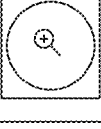 | ZOOM WITH MOUSE WHEEL | MOUSE WHEEL WILL ZOOM 2D IMAGES (NORMALLY MOUSE WILL SCROLLS 2D IMAGES). |
| 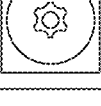 | PREFERENCES | OPENS DIALOG FOR APPLICATION AND SURGEON PREFERENCES. |
| 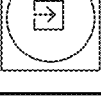 | EXIT | EXITS THE APPLICATION, PROMPTS FOR SAVING IF CHANGES HAVE BEEN MADE. |

FIG. 54

SYSTEM AND METHOD FOR PROVIDING SURGICAL PLANNING AND GUIDANCE WITH THREE-DIMENSIONAL VISUALIZATION

CROSS-REFERENCE TO RELATED APPLICATIONS

The present application claims priority to and the benefit of U.S. Provisional Patent Application Ser. No. 63/121,029, filed on Dec. 3, 2020, which is incorporated herein by reference in its entirety.

FIELD OF THE INVENTION

The present application relates to surgical navigation technologies, implant positioning technologies, imaging technologies, surgical planning technologies, registration technologies, robotics technologies, and more particularly, to a system and method for providing surgical planning and guidance with three-dimensional visualization.

BACKGROUND

In today's society, companies and individuals are increasingly spending time, financial resources, and efforts to develop technologies that provide more effective and efficient healthcare for subjects, such as patients. For example, through innovation, a variety of technologies have been developed that facilitate the performance of surgical procedures on subjects. Such technologies include, but are not limited to, passive and active surgical robots, innovative medical equipment and tools, software and componentry for facilitating surgical navigation, among other technologies. Despite the existence of such technologies, there remains room for substantial enhancements to existing technologies and the development of new technologies, especially in the context of orthopedic surgical procedures.

In joint replacement surgery (i.e. arthroplasty), such as for a knee replacement, the subject's affected anatomy is removed and then replaced with an artificial joint implant. For example, in the context of the knee replacement, the bone and joint in the subject's knee area are removed and replaced with an artificial joint implant. Notably, however, arthroplasty requires accurate planning of the implant pose (i.e. the implant's position and orientation) relative to the subject's anatomy. Without the optimal implant pose, the subject may experience complications after the surgery, such as, but not limited to, pain and limited range of motion. In order to plan the poses of the implant, the current practice standard first involves scanning the subject's anatomy by utilizing one or more medical imaging modalities, such as X-ray, computed tomography (CT), magnetic resonance imaging (MRI), or other imaging technologies. Once the images of the anatomy are generated, the implant plan is prepared based on the scanned images of the subject's anatomy. In particular, the implant poses are planned relative to the subject's anatomy. A goal of planning is to optimally align the implant, and to restore the normal and pain-free function of the joint. When planning the implant pose, surgeons need to consider multiple distance and angle metrics. Notably, however, implant planning is a time-consuming process that requires experienced professionals to achieve proper implant placement.

Once the implant position is planned, the next challenge is to place the physical implant components in the appropriate planned poses. In order to facilitate and guide implant placement during surgery, several real-time navigation methodologies are available for the surgeon operating on the subject. For example, surgeons can utilize surgical navigation systems in this regard. These surgical navigation systems typically track the pose of the bones and the cutting tools in real time, and display guidance information for the surgeon on a screen in the operating room that helps them position the cutting tools to achieve the planned cuts. In order to conduct accurate navigation, all currently-existing image-based navigation systems rely on a process called registration. Typically, a 3D navigation system determines the pose of the bones of the subject. Portions of the affected anatomy are typically localized using tracked pointers, surface scanner devices, or other methods. Once enough information is collected of the subject bone location, the registration algorithm matches this data with the bone and joint surfaces detected in the image set (e.g. images obtained via CT) to establish the spatial relationship between the subject's anatomy and the information provided in the image set. The registration process conventionally uses a digital model of the bone surface derived from manually or semi-automatically defined contours in the image set. These bone contours are currently created in a time-consuming, labor-intensive process, especially when pathological bones have reduced the signal in the image set. Additionally, current surgical methods that use an image set (e.g. a 3D image set) for planning and guidance start by delineating the bone contours in the images of the image set. Then, based on the delineated bone contours, 3D computer-graphics models of the bones are generated. The generated bone models are utilized to show the spatial relationships between implants and bone surfaces during the planning stage. Notably, the generated bone models are also used to define anatomical landmark points to measure distances and angles between the anatomy and the implant. During a surgery on a subject, the bone contours are used in the registration process to determine the planned implant position relative to the subject's bones.

Notably, precise implant planning is required by navigation and robotic surgical methodologies before or during surgery. Early technologies on surgical assistance methods required bone surface contours to be defined before planning the position of the implant. Additionally, the first versions of robotic arthroplasty systems relied on contouring of the bone surfaces in images taken before surgery. These technologies are still utilized in current surgical planning systems. In certain instances, manual contouring is often enhanced with semi-automatic methods, such as by morphing a generic anatomical model based on points defined in the current 3D image set. Still further, recent research on bone contouring involves utilizing deep convolutional neural networks to automatically find bone surfaces in the 3D image sets.

Regarding the implants utilized in the surgeries, the implants can be customized in shape and size based on anatomical landmark points defined in medical images. This customization process facilitates and enables better fitting of the implant in subjects, but the process comes with additional preparation time and cost for each implant. Additionally, if the customized implant is not inserted in the subject in the optimal position, then the benefits of the customized shape may be limited. Currently, the widely used approach is to select implant sizes from a set of sizes offered by various manufacturers. These standard implants may restore joint function with reduced reported pain after surgery if the implants' positions are optimally planned and the plan is accurately executed during surgery.

Notably, while currently existing technologies provide for various benefits, such technologies still come with various drawbacks and inefficiencies. For example, the bone contouring process utilized for planning and registration usually takes significant amounts of time and resources, whether conducted by a human or even by using computerized technologies and neural networks. This is especially true for subjects having pathological bone density or bone deformations. Additionally, the process of contouring frequently requires manual steps that may introduce human error and lead to variable outcomes between different users. Based on the foregoing, current technologies may be improved and enhanced so as to provide for faster planning, enhanced registration capabilities, reduced usage of resources, reduced errors, greater efficiencies, fewer user interactions, enhanced visualization capabilities, and improved information. Such enhancements and improvements to methodologies and technologies may provide for increased surgical effectiveness, improved surgical outcomes, and increased ease-of-use for surgeons.

SUMMARY

A system and accompanying methods for providing surgical planning and guidance with three-dimensional visualization are disclosed. In particular, the system and methods facilitate implant planning and registration by utilizing software to provide 3D image set-based implant positioning functionality that does not require bone contouring of a subject's bones in the images of the image set. The system and method include conducting imaging of a subject's anatomy of interest. For example, the imaging may be 3D imaging, such as provided by a computed tomography (CT) device, magnetic resonance imaging (MRI) device, or other suitable imaging device and/or technology. In certain embodiments, other imaging technologies may be utilized, such as, but not limited to, X-ray imaging technologies. In certain embodiments, the image set that results from conducting the imaging of the subject's anatomy may be processed by utilizing automatic 3D image filters to reduce noise and eliminate portions of the subject's anatomy that are not required for implant planning and registration. The system and methods may then include rendering the 3D images of the subject's bones on a display by utilizing volume rendering. Notably, the rendering may be accomplished without having to generate surface models. Once the rendering of the 3D images is completed, the system and methods may include, during generation of a plan for surgery for the subject, receiving inputs suggesting and/or defining anatomical landmark points in the rendered volume shown in the 3D images. In certain embodiments, a user or the system itself may refine the suggested landmark points as necessary before the landmark points are accepted. The system and methods may also utilize any other types of inputs for generation of the plan including, but not limited to, the implant type of the implant to be implanted, the type of approach to be utilized for implantation, information associated with the sides of the anatomy and/or implant itself, bone density information, bone size information, bone surface information, information associated with the subject, any other information, or a combination thereof.

Once the anatomical landmarks are defined and/or any other inputs are received for the plan, the system and methods may include conducting implant positioning using real-time visual feedback, such as via a computing device and accompanying user interface. In certain embodiments, the implant positioning may be performed by a surgeon, an active robot, a passive robot, medical devices, other devices, artificial intelligence-based technologies, or a combination thereof. During the positioning of the implant, the system and methods may include generating and displaying, on a user interface, one or more position controls for controlling the position of the implant. In certain embodiments, the position controls for positioning the implant may be visually displayed intuitively such that the position controls are rendered in proximity to the subject interface views where the volume rendering of the subject's bones are displayed. Each time the position of the implant is adjusted by a surgeon (or device), the system and methods may update the corresponding bone cuts of the anatomy of the subject and visualize the updated bone cuts in real-time using volume rendering. In certain embodiments, the system and methods may calculate measurements related to the implant pose each time the implant positions are adjusted. The measurements related to the implant pose may be blended and displayed with volume rendering to assist the surgeon (or device) to select the optimal implant positions for the implant. Once the desired implant positions are selected, the system and methods may save the implant positions relative to the accepted landmark points in the plan for the subject.

The system and methods may then proceed to the registration process, which may include having the surgeon (or device) examine the subject and determine the actual position of the bones of the subject, such as by utilizing a surgical navigation system. This process may occur during or before surgery on the subject. Once the actual position of the bones and/or associated anatomy are determined, the system and methods may match the actual positions directly to the position data in the plan for the subject. If the registration process fails and/or match cannot be achieved, the system and methods may include re-attempting or refining the registration process to match the actual positions of the anatomy to the position data in the plan for the subject. In certain embodiments, if the registration fails, the surgeon may proceed with performing a conventional surgical implant procedure on the subject without the plan. If, however, the registration process and matching is successful, the system and methods may include enabling the surgeon (or device) to proceed with the surgery using the plan. During surgery, the system and methods may then include utilizing surgical navigation systems to guide the surgeon (or device) in terms of cutting the bones and accurately positioning the implant components onto the anatomy of interest of the subject.

Notably, the functionality and features provided by the system and methods minimize the time of image set-based implant planning (e.g. 3D image set-based planning) by optimizing image processing and display. The system and methods further enable the simultaneous display of 3D bone cuts with critical distance and angle metrics for a surgeon (or device) during the planning process. Additionally, the system and methods provide for a registration process that does not require contouring or the use of digital surface models. Instead, the system and methods accomplish the registration process by directly using the 3D image set enhanced via the volume rendering. The volume rendering utilized by the system and methods has greater speed and fewer user interactions than bone contouring. Indeed, contouring only defines the outer surface of perceived bones in the image sets, while information on the internal structure of the bone is typically lost. In contrast, the volume rendering utilized by the system and method involves assigning a scale of visible colors (e.g. such as, but not limited to, a continuous scale) and opacity to variable pixel values, variable voxel values, or both, in the 3D image sets. In certain embodiments, in the context of image(s), the pixel or voxel values may be related to bone density information. As an illustrative example, in the context of CT images, the pixel value in Hounsfield Units may be related to bone density information, however, in the context of Mill images, the pixel value may not represent density information. However, in certain instances, MM images may be converted to CT-like images with pixel/voxel values matching Hounsfield units of equivalent CT. When the planned implant model is observed in the context of volume rendering, the position can be optimized not only based on bone surface geometry, but also on maximum support by dense bone contact with the implant. This may ultimately lead to more stable and longer lasting implants. Based on at least the foregoing, the system and methods provide for faster planning, enhanced registration capabilities, reduced usage of resources, reduced errors, greater efficiencies, fewer patient/subject interactions, enhanced visualization capabilities, and enhanced information. Such enhancements facilitate increased surgical effectiveness, improved surgical outcomes, and increased ease-of-use for surgeons.

In one embodiment, a system for providing surgical planning and guidance with three-dimensional visualization is provided. The system may include a memory that stores instructions and a processor that executes the instructions to perform various operations of the system. The system may perform an operation that includes obtaining an image (or image set) of an anatomy of interest of a subject. For example, the image may be taken by utilizing a 3D technology system, such, as but not limited to an Mill device, a CT device, an X-ray device, any type of imaging device, or a combination thereof. In certain embodiments, the image (or image set) may be processed by utilizing automatic 3D image filters to reduce noise and/or eliminate portions of the anatomy that are not required for implant planning and/or registration. The system may proceed to perform an operation that includes rendering, by utilizing volume rendering, an enhanced version of the image of the anatomy of interest on a user interface. Additionally, the system may perform an operation that includes generating a plan for implanting an implant onto the anatomy of interest based on an input including a landmark point for the enhanced version of the image of the anatomy of interest. In certain embodiments, other inputs may also be utilized for generating the plan, such as, but not limited to, information relating to the implant type of the implant to be implanted, the type of approach to be utilized for implantation, information associated with the sides of the anatomy and/or implant itself, bone density information, bone size information, bone surface information, information associated with the subject, information associated with the type of surgical procedure, any other information, or a combination thereof. The system may proceed to perform an operation that includes facilitating, via an implant position control, implant positioning for the plan for the implant. In certain embodiments, selection of an implant position for the plan for the implant is facilitated based on the implant positioning. The system may proceed to perform an operation that includes conducting a registration process to match the anatomy of interest of the subject with the information contained in the enhanced version of the image of the anatomy of interest in the plan. Once the registration process is performed, the system may perform an operation that includes facilitating, by utilizing the plan and based on the match conducted via the registration process, performance of a surgical procedure for implanting the implant onto the anatomy of interest of the subject.

In another embodiment, a method for providing surgical planning and guidance with three-dimensional visualization is disclosed. The method may include a memory that stores instructions and a processor that executes the instructions to perform the functionality of the method. In particular, the method may include obtaining an image of an anatomy of interest of a subject. Additionally, the method may include rendering, by utilizing volume rendering, an enhanced version of the image of the anatomy of interest on a user interface. Also, the method may include generating a plan for implanting an implant onto the anatomy of interest based on an input including a landmark point for the enhanced version of the image of the anatomy of interest. Other inputs, such as, but not limited to, the implant type of the implant to be implanted, the type of approach to be utilized for implantation, information associated with the sides of the anatomy and/or implant itself, bone density information, bone size information, bone surface information, information associated with the subject, any other information, or a combination thereof, may also be utilized in generating the plan. The method may proceed to include facilitating, via one or more implant position controls, implant positioning for the plan for the implant. Once the implant positioning for the plan has been conducted, the method may include conducting a registration process to match the anatomy of interest of the subject with the enhanced version of the image of the anatomy of interest in the plan. Furthermore, the method may include performing, by utilizing the plan and based on the match conducted via the registration process, a surgical procedure for implanting the implant onto the anatomy of interest of the subject.

According to yet another embodiment, a computer-readable device comprising instructions, which, when loaded and executed by a processor cause the processor to perform operations, the operations comprising: obtaining an image of an anatomy of interest of a subject; rendering, by utilizing volume rendering, an enhanced version of the image of the anatomy of interest on a user interface; generating a plan for implanting an implant onto the anatomy of interest based on an input including a landmark for the enhanced version of the image of the anatomy of interest; facilitating, via an implant position control, implant positioning for the plan for the implant; conducting a registration process to match the anatomy of interest of the subject with the enhanced version of the image of the anatomy of interest in the plan; and performing, by utilizing the plan and based on the match conducted via the registration process, a surgical procedure for implanting the implant onto the anatomy of interest of the subject.

These and other features of the systems and methods for providing surgical planning and guidance with three-dimensional visualization are described in the following detailed description, drawings, and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 7:
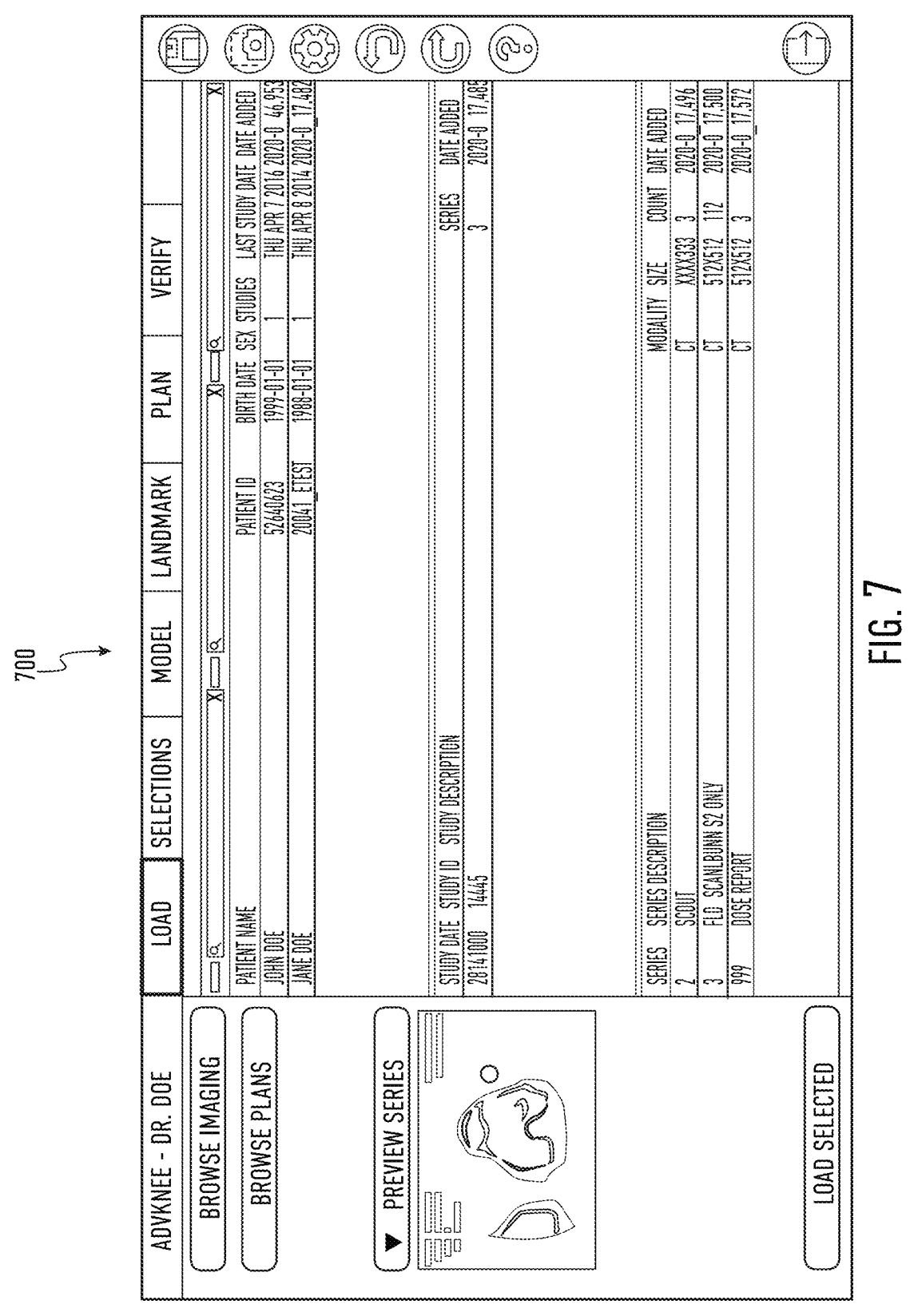

FIG. 7 is a sample user-interface of an application for use with the system of FIG. 1, which enables the importation and selection of an image set to be loaded into the system of FIG. 1.

FIG. 24 is a sample user-interface of an application for use with the system of FIG. 1, which facilitates a final review of landmarks prior to implant position planning.

FIG. 54 is an assortment of various controls that may be utilized by a user of the system of FIG. 1.

DETAILED DESCRIPTION OF THE DRAWINGS

Figure 1:
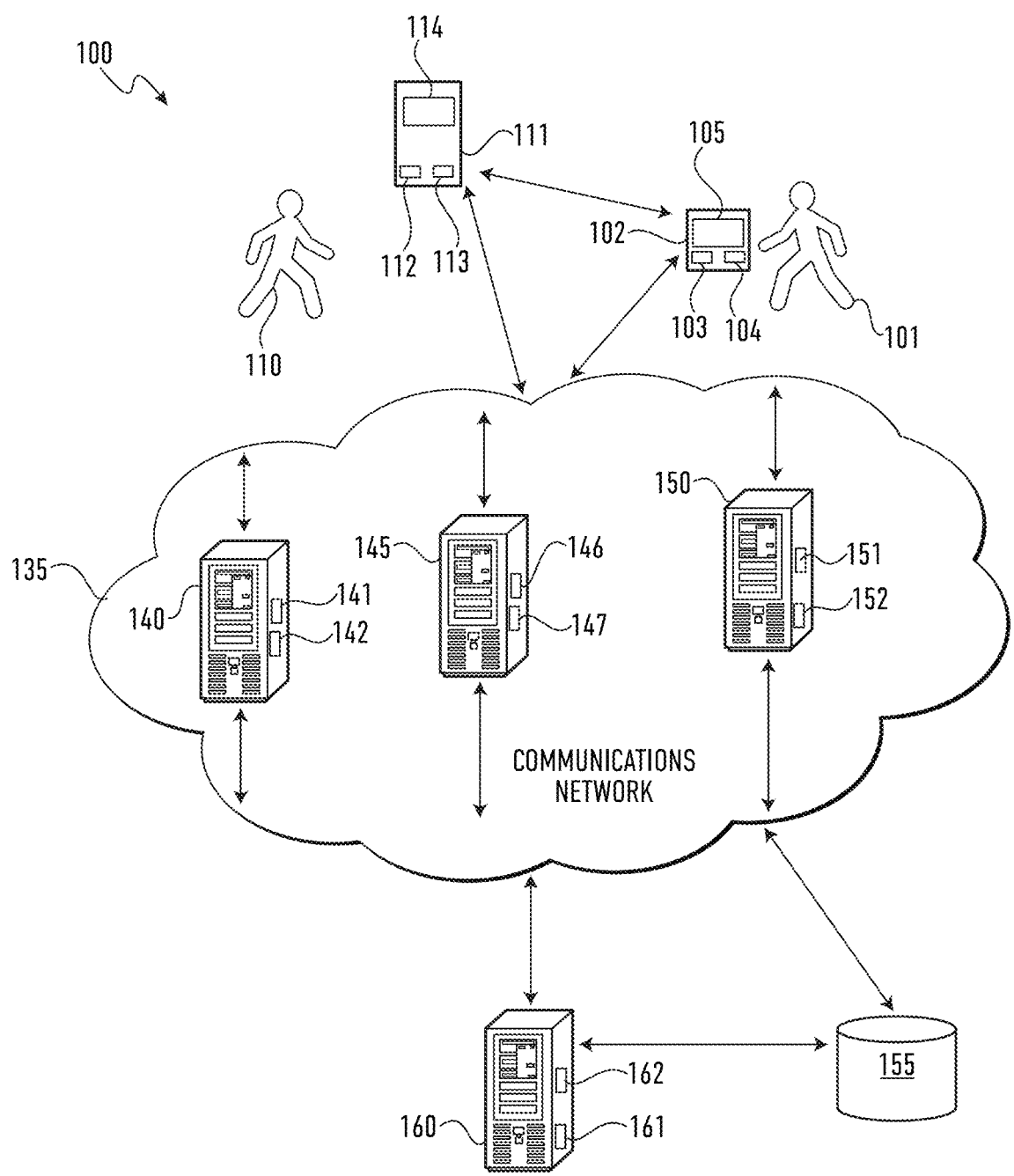
FIG. 1 is a schematic diagram of a system for providing surgical planning and guidance with three-dimensional visualization according to an embodiment of the present disclosure.

A system 100 and accompanying methods for providing surgical planning and guidance with three-dimensional visualization are disclosed. In particular, the system 100 and methods facilitate implant planning and registration by utilizing software to provide image set-based implant positioning functionality that does not require bone contouring of a subject's bones in the images of the image set. The system 100 and method include conducting imaging of a subject's anatomy of interest, such as by utilizing a CT device, Mill device, an X-ray device, and/or other suitable imaging device and/or technology. In certain embodiments, the image set that results from conducting the imaging of the subject's anatomy may be processed by utilizing automatic image filters to reduce noise and eliminate portions of the subject's anatomy that are not required for implant planning and registration. The system 100 and methods may then include rendering the images of the subject's bones on a display by utilizing volume rendering. Notably, the rendering may be accomplished without having to generate surface models or conducting bone contouring. Once the rendering of the images is completed, the system 100 and methods may include, during generation of a plan for surgery for the subject, receiving inputs suggesting and/or defining anatomical landmark points in the rendered volume shown in the images. In certain embodiments, a subject or the system 100 itself may refine the suggested landmark points as necessary before the landmark points are accepted for the plan. Notably, the system 100 and methods may also utilize any other types of inputs for generation of the plan including, but not limited to, the implant type of the implant to be implanted, the type of approach to be utilized for implantation, information associated with the sides of the anatomy and/or implant itself, bone density information, bone size information, bone surface information, information associated with the subject, any other information, or a combination thereof.

Once the anatomical landmarks are defined and accepted, and/or any other inputs are received for the plan, the system 100 and methods may include conducting implant positioning using real-time visual feedback, such as via a computing device and accompanying user interface. In certain embodiments, the implant positioning may be performed by a human surgeon, an active robot, a passive robot, medical devices, other devices, or a combination thereof. The system 100 and methods may include generating and displaying, on a user interface, one or more position controls for controlling the position of the implant. In certain embodiments, the position controls for positioning the implant may be visually displayed such that the position controls are rendered in proximity to the subject interface views where the volume rendering of the subject's bones are displayed. Whenever the position of the implant is adjusted by a surgeon (or device), the system 100 and methods may update the corresponding bone cuts of the anatomy of the subject and visualize the updated bone cuts in real-time using volume rendering. In certain embodiments, the system 100 and methods may calculate measurements related to the implant pose each time the implant positions are adjusted. The measurements related to the implant pose may be blended and displayed with volume rendering to assist the surgeon (or device) to select the optimal or desired implant positions for the implant. Once the optimal and/or desired implant positions are selected, the system 100 and methods may save the implant positions relative to the accepted landmark points in the plan for the subject.

The system 100 and methods may then proceed to the registration process, which may include having the surgeon (or device) examine the subject and determine the actual position of the bones of the subject, such as by utilizing a surgical navigation system. This process may occur during or before surgery on the subject, and may involve determining the position of the bones after surgically opening up the subject in the area of the anatomy of interest. Once the actual position of the bones and/or associated anatomy are determined, the system 100 and methods may match the actual positions to the position data in the plan for the subject. If the registration process fails and/or match cannot be achieved, the system 100 and methods may include re-attempting or refining the registration process to match the actual positions of the anatomy to the position data in the plan for the subject. In certain embodiments, if the registration fails, the surgeon may proceed with performing a conventional surgical implant procedure on the subject without using the plan. If, however, the registration process and matching is successful, the system 100 and methods may include enabling the surgeon (or device) to proceed with the surgery using the plan. During surgery, the system 100 and methods may then include utilizing surgical navigation systems to guide the surgeon (or device) in terms of cutting the bones and accurately positioning the implant components onto the anatomy of interest of the subject.

Figure 56:
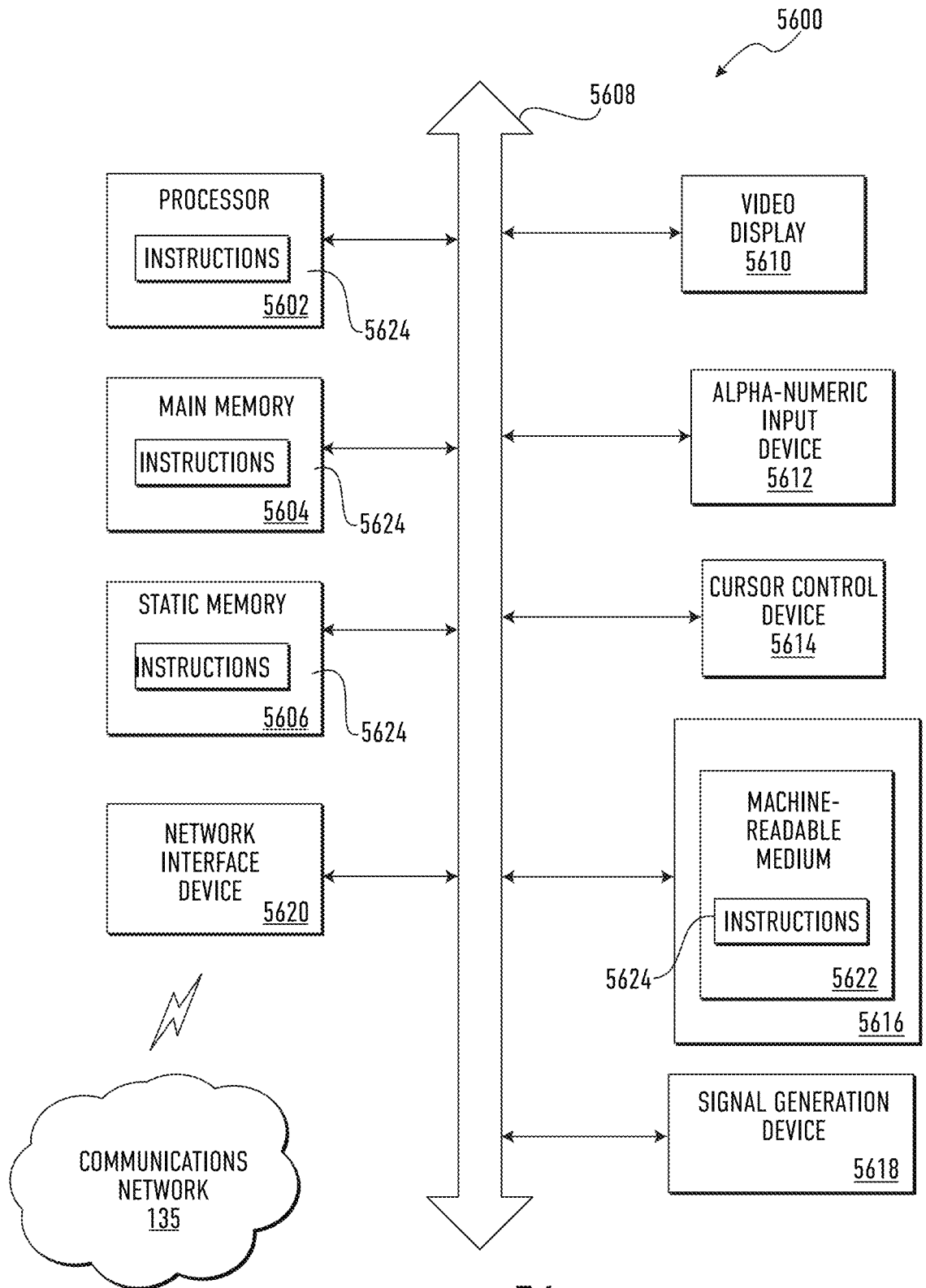
FIG. 56 is a schematic diagram of a machine in the form of a computer system within which a set of instructions, when executed, may cause the machine to provide surgical planning and guidance with three-dimensional visualization.
Figure 57:
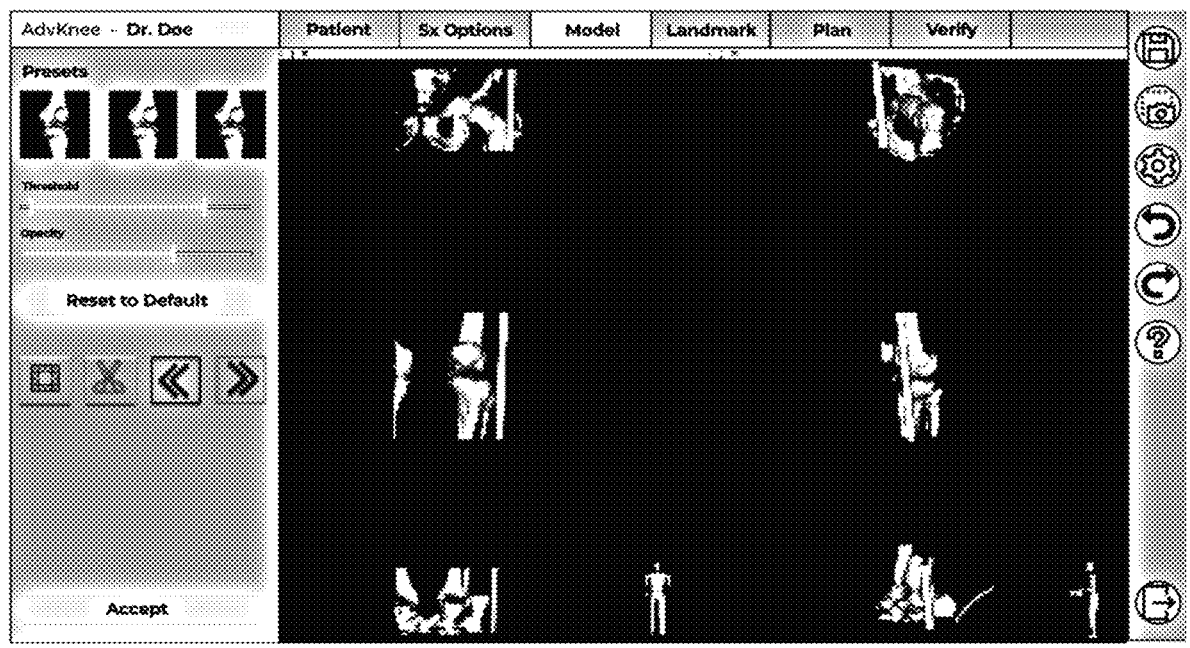
FIG. 57 is a sample user-interface of an application for use with the system of FIG. 1 presented in color, which enables viewing of an enhanced image set.
Figure 58:
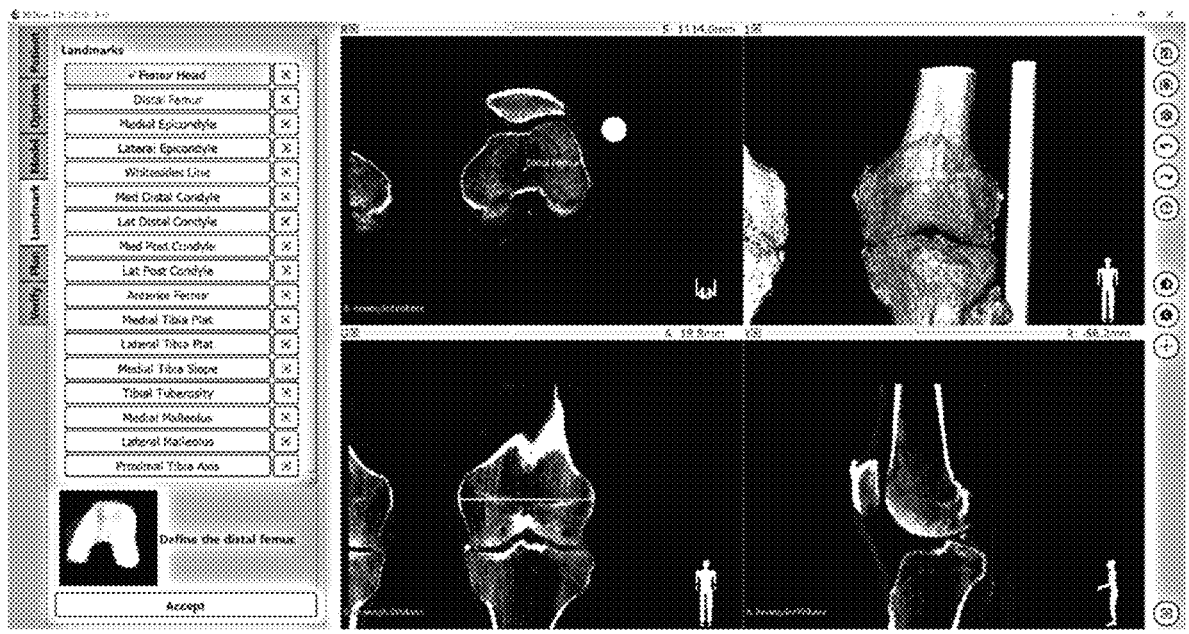
FIG. 58 is a sample user-interface of an application for use with the system of FIG. 1 presented in color, which facilitates the selection of landmark points on an anatomy of a subject.
Figure 59:
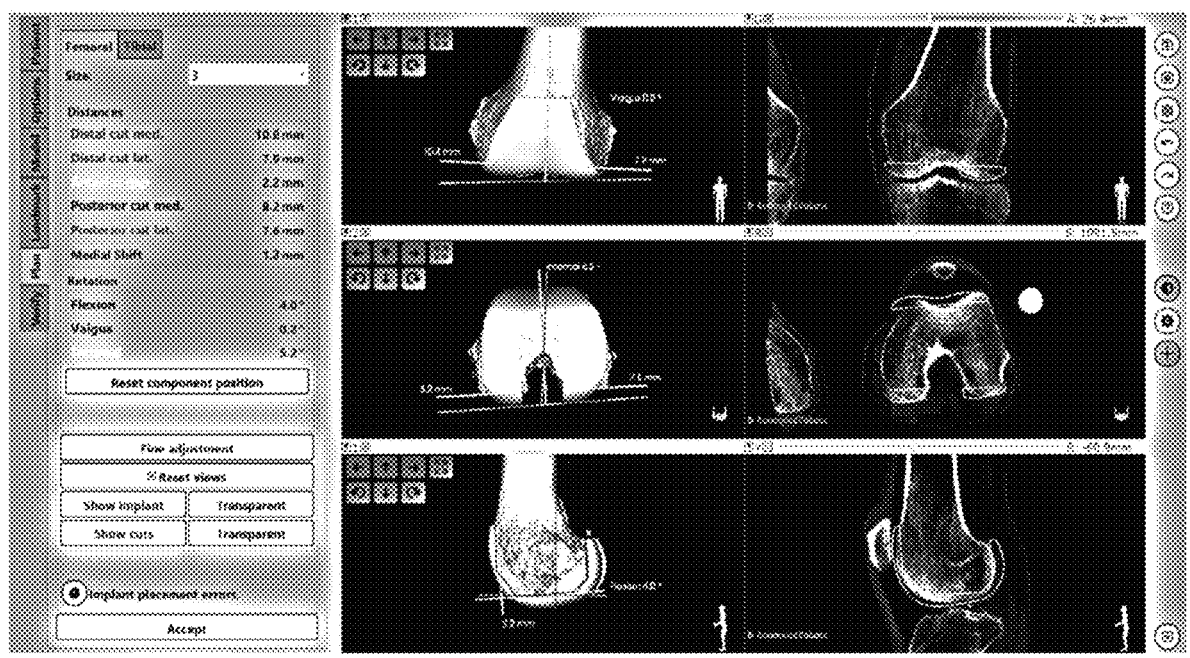
FIG. 59 is a sample user-interface of an application for use with the system of FIG. 1 presented in color, which facilitates implant positioning with real-time visual feedback.
Figure 60:
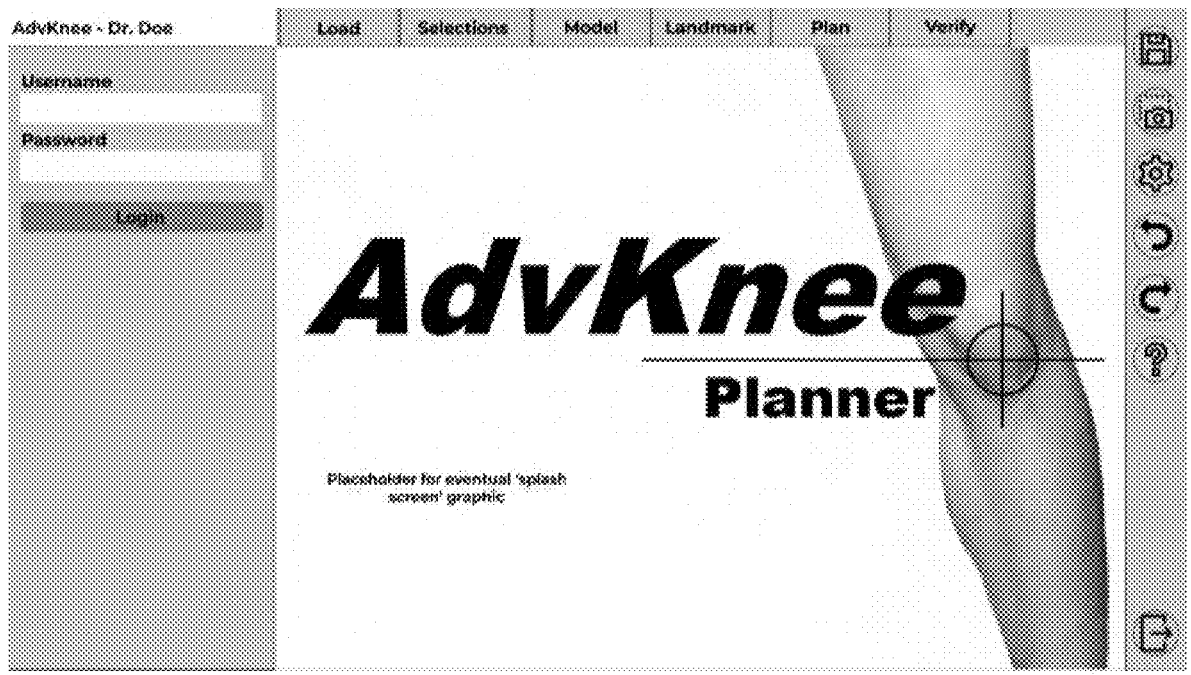
FIG. 60 is a sample user-interface of an application for use with the system of FIG. 1 presented in color, which enables a user to authenticate into and access the features of the system of FIG. 1.
Figure 61:
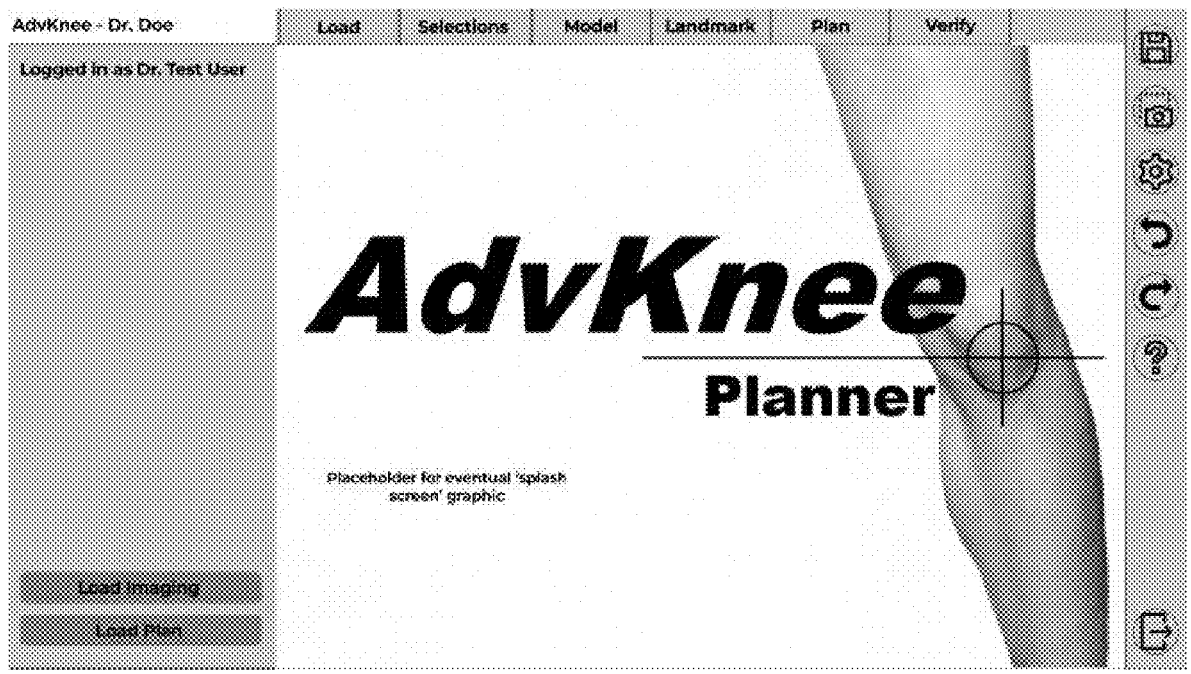
FIG. 61 is a sample user-interface of an application for use with the system of FIG. 1 presented in color, which facilitates loading of an image to start a new plan for a subject or load an existing plan for the subject.
Figure 62:
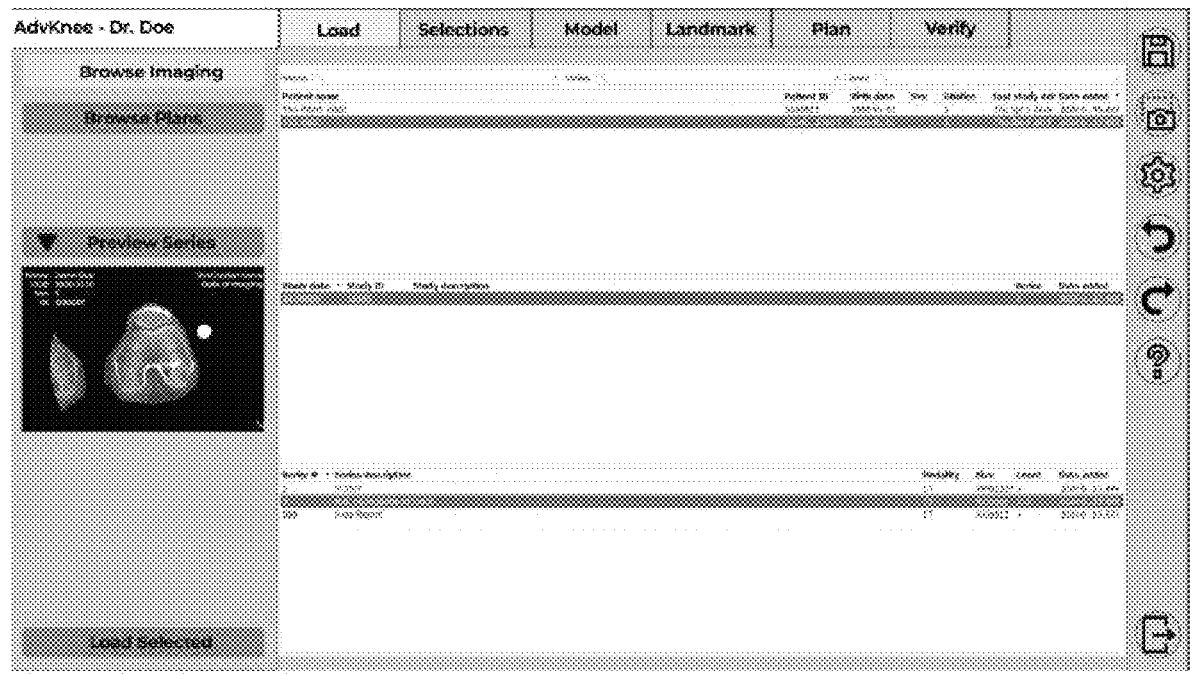
FIG. 62 is a sample user-interface of an application for use with the system of FIG. 1 presented in color, which enables the importation and selection of an image set to be loaded into the system of FIG. 1.
Figure 63:
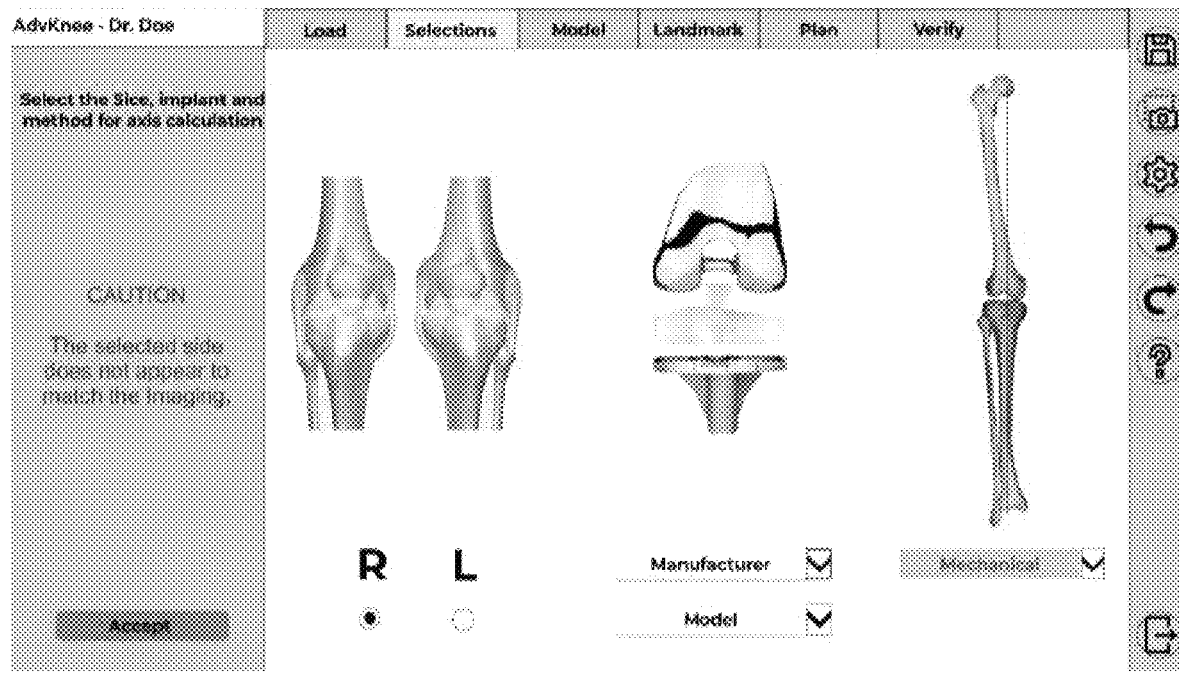
FIG. 63 is a sample user-interface of an application for use with the system of FIG. 1 presented in color, which facilitates the selection of the type of implant to be utilized for a surgical procedure, which side of the anatomy that the surgical procedure will be performed on, and the surgical method to be utilized for surgical procedure.
Figure 64:
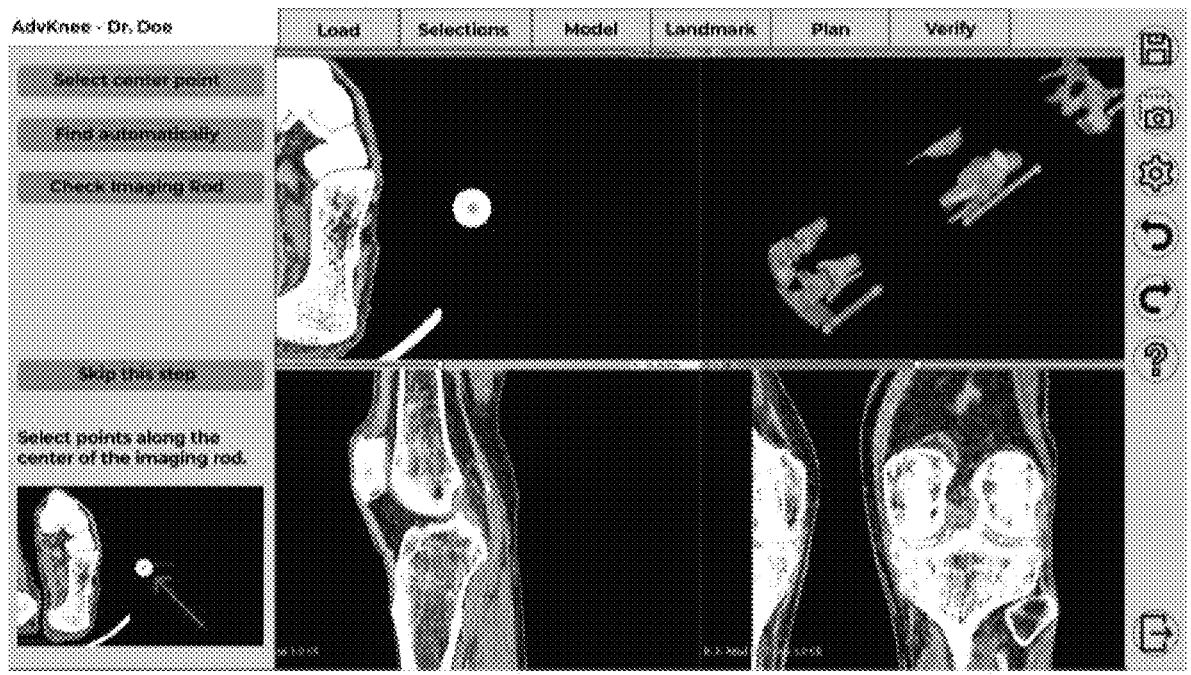
FIG. 64 is a sample user-interface of an application for use with the system of FIG. 1 presented in color, which facilitates selection of imaging rod points if an imaging rod is utilized with the system of FIG. 1.
Figure 65:
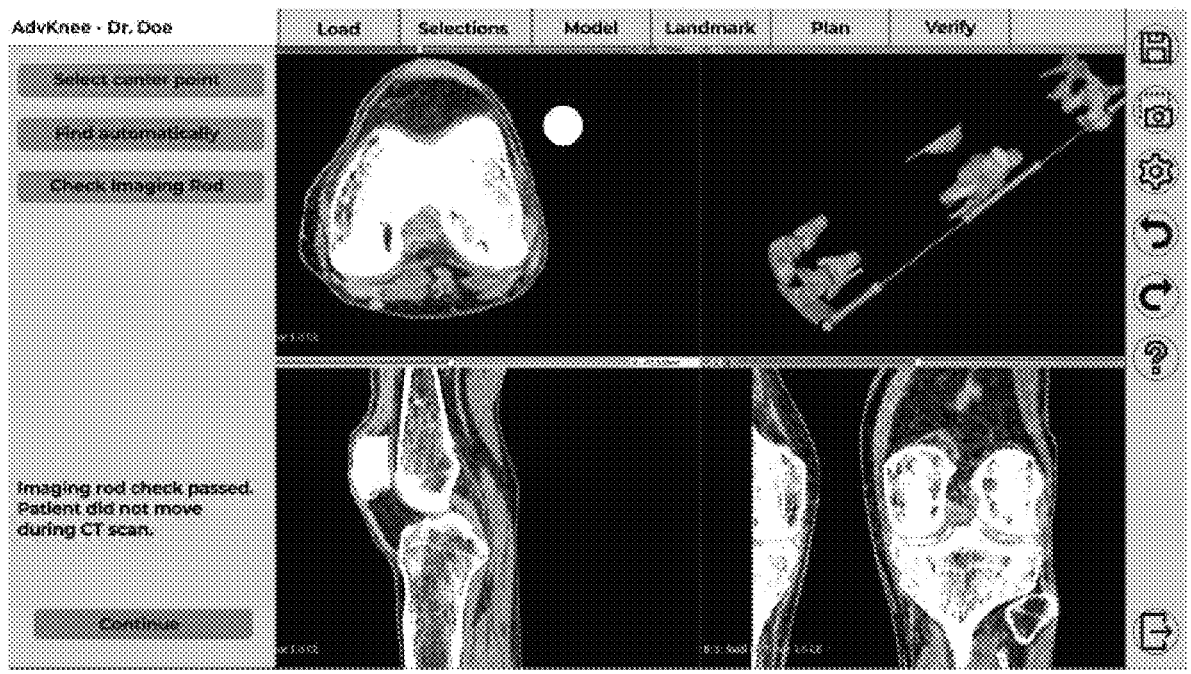
FIG. 65 is a sample user-interface of an application for use with the system of FIG. 1 presented in color, which facilitates the visualization of an imaging rod after selection of imaging rod points.
Figure 66:
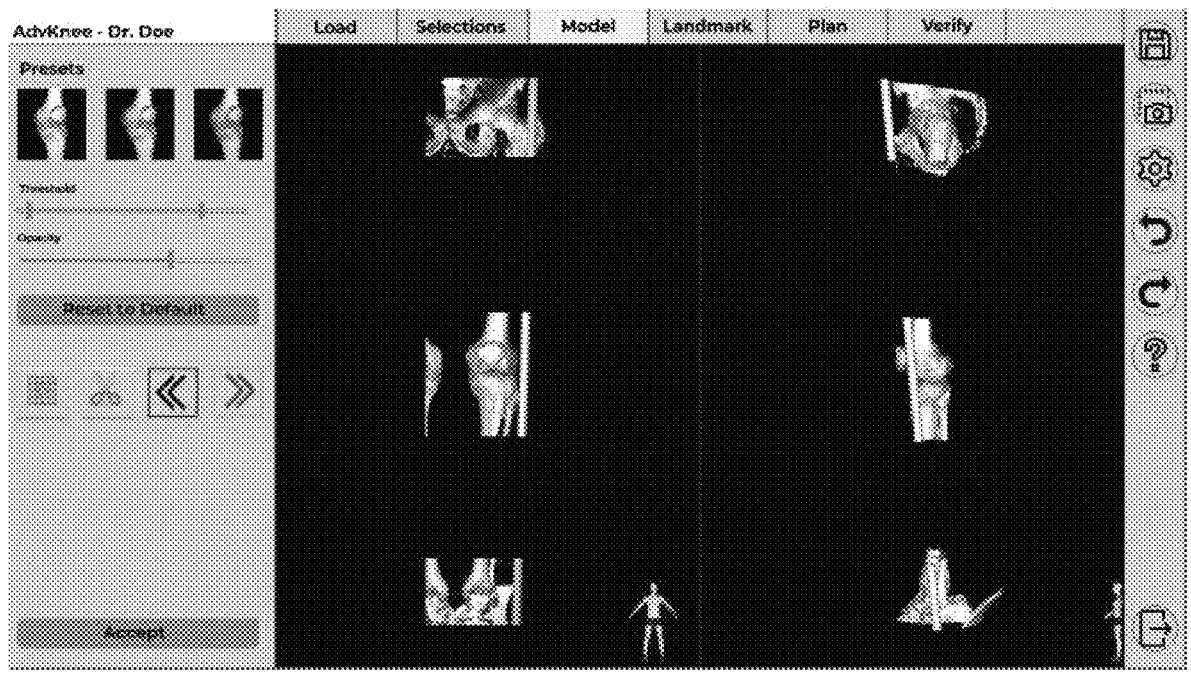
FIG. 66 is a sample user-interface of an application for use with the system of FIG. 1 presented in color, which facilitates the setting up of volume rendering that may be used for generating a plan for the subject.
Figure 67:
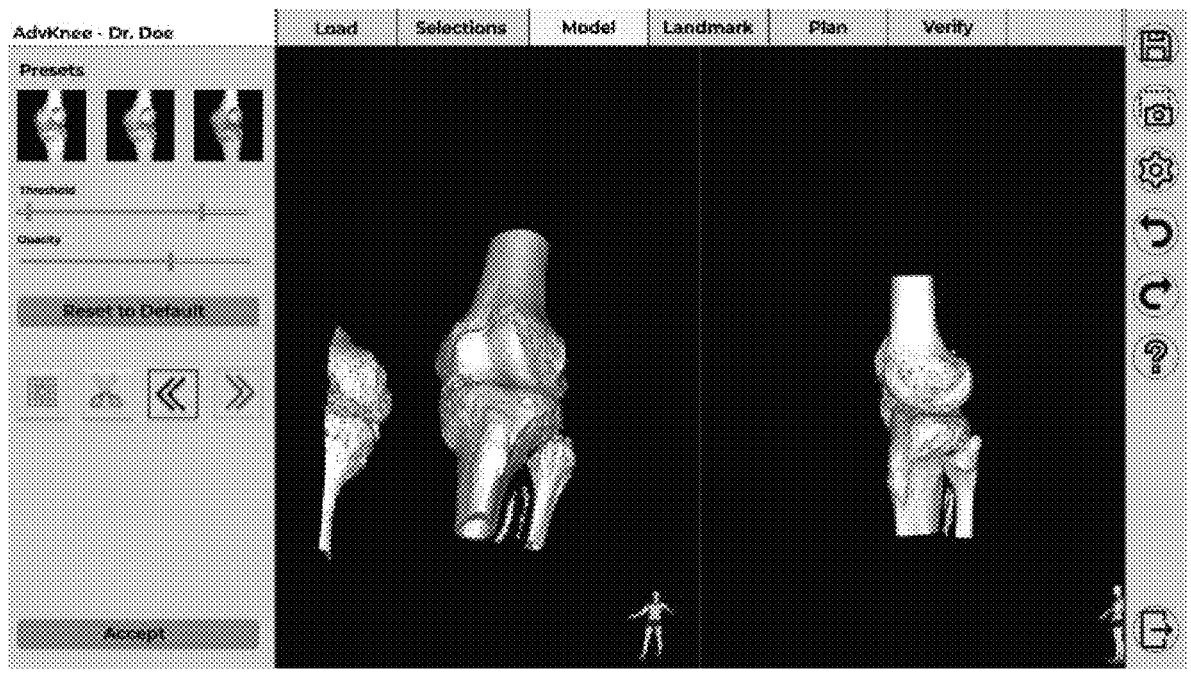
FIG. 67 is a sample user-interface of an application for use with the system of FIG. 1 presented in color, which facilitates the digital editing of the rendered volume of the anatomy.
Figure 68:
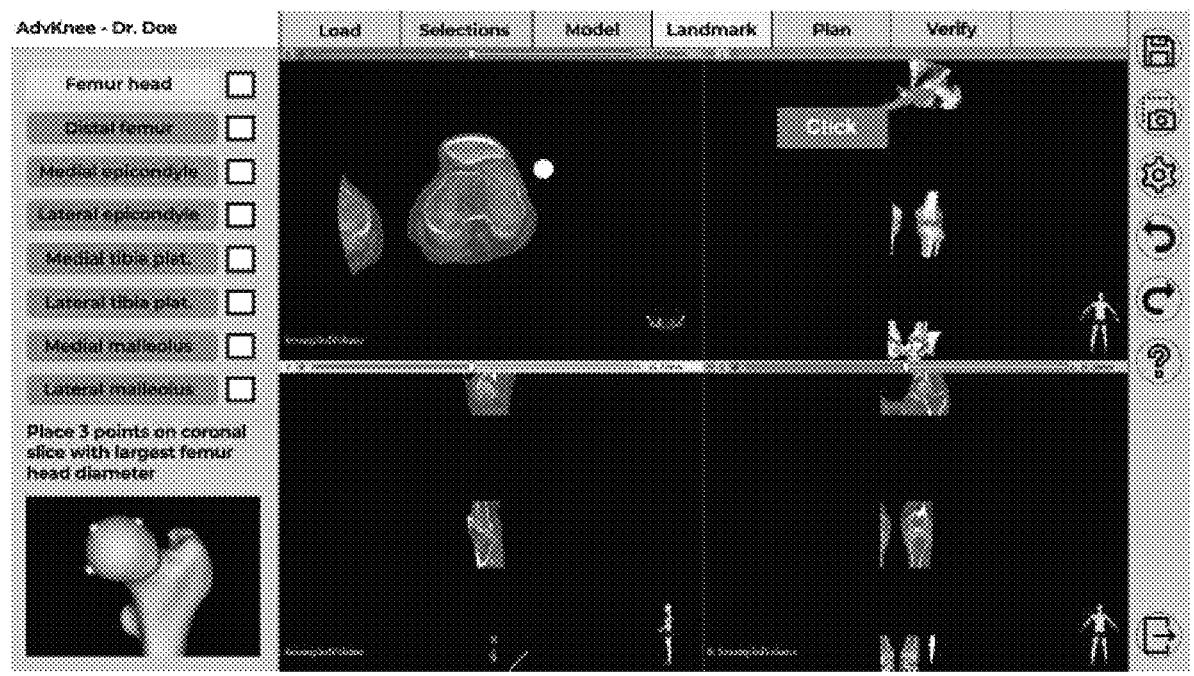
FIG. 68 is a sample user-interface of an application for use with the system of FIG. 1 presented in color, which facilitates anatomical landmarking.
Figure 69:
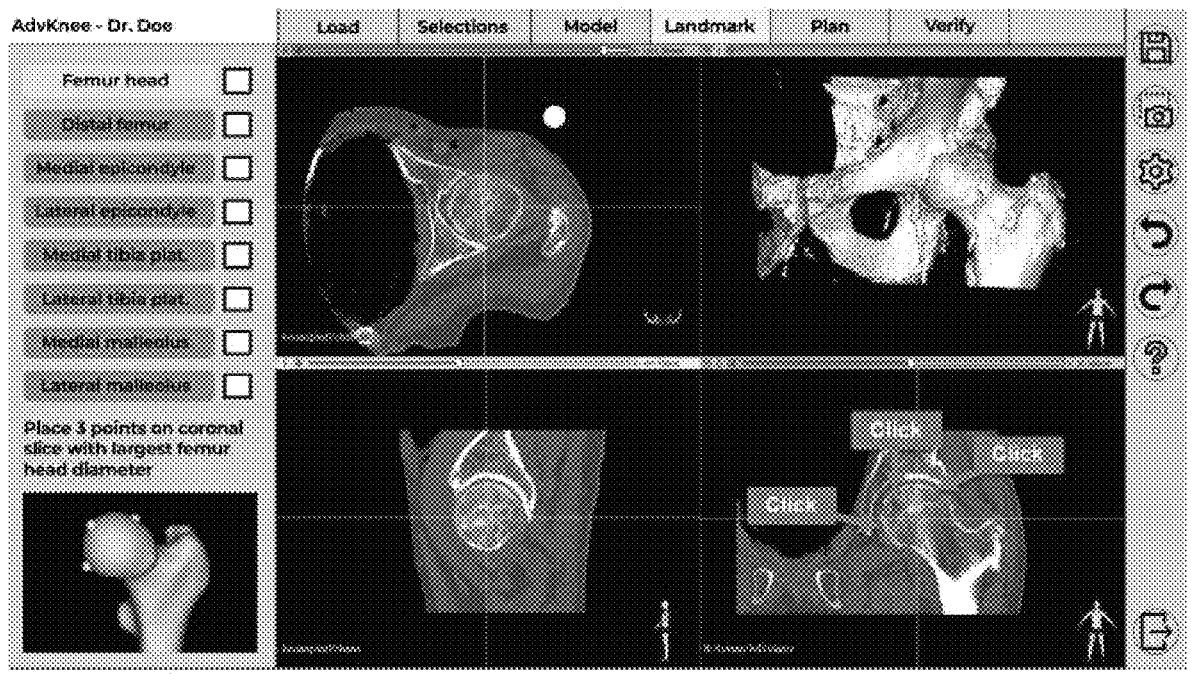
FIG. 69 is a sample user-interface of an application for use with the system of FIG. 1 presented in color, which facilitates the defining of landmark points for a portion of the anatomy of a subject.
Figure 70:
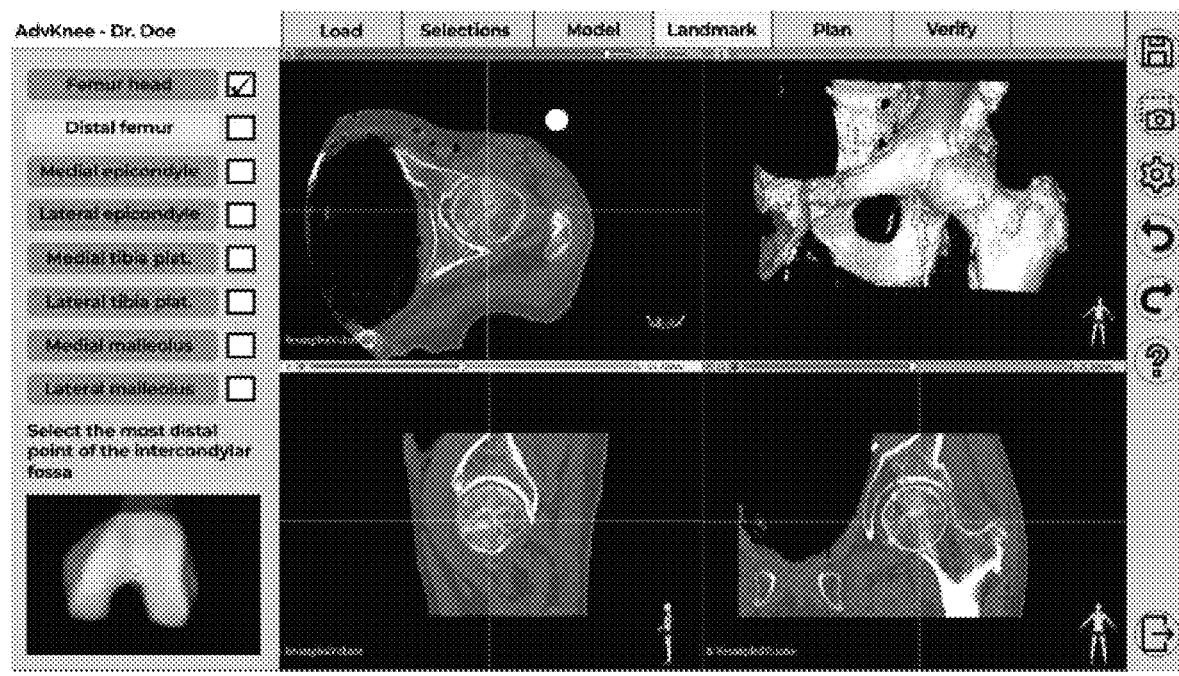
FIG. 70 is a sample user-interface of an application for use with the system of FIG. 1 presented in color, which facilitates anatomical landmarking for another portion of the anatomy of the subject.
Figure 71:
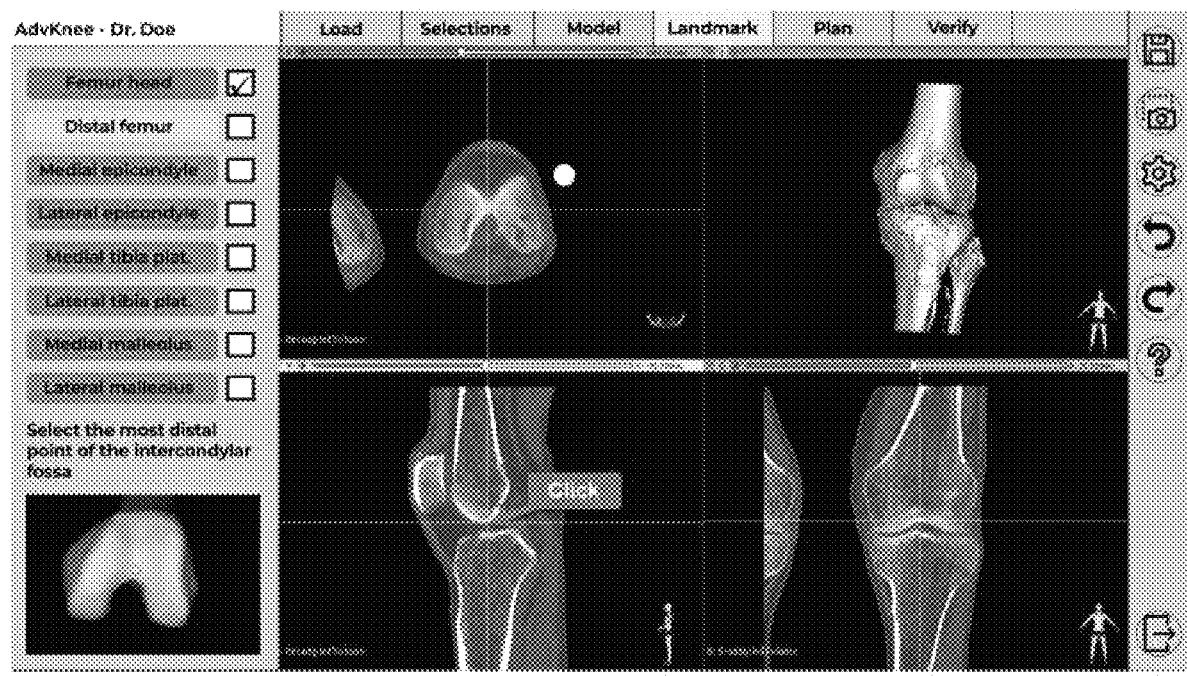
FIG. 71 is a sample user-interface of an application for use with the system of FIG. 1 presented in color, which facilitates the placement of landmark points for a portion of the anatomy.
Figure 72:
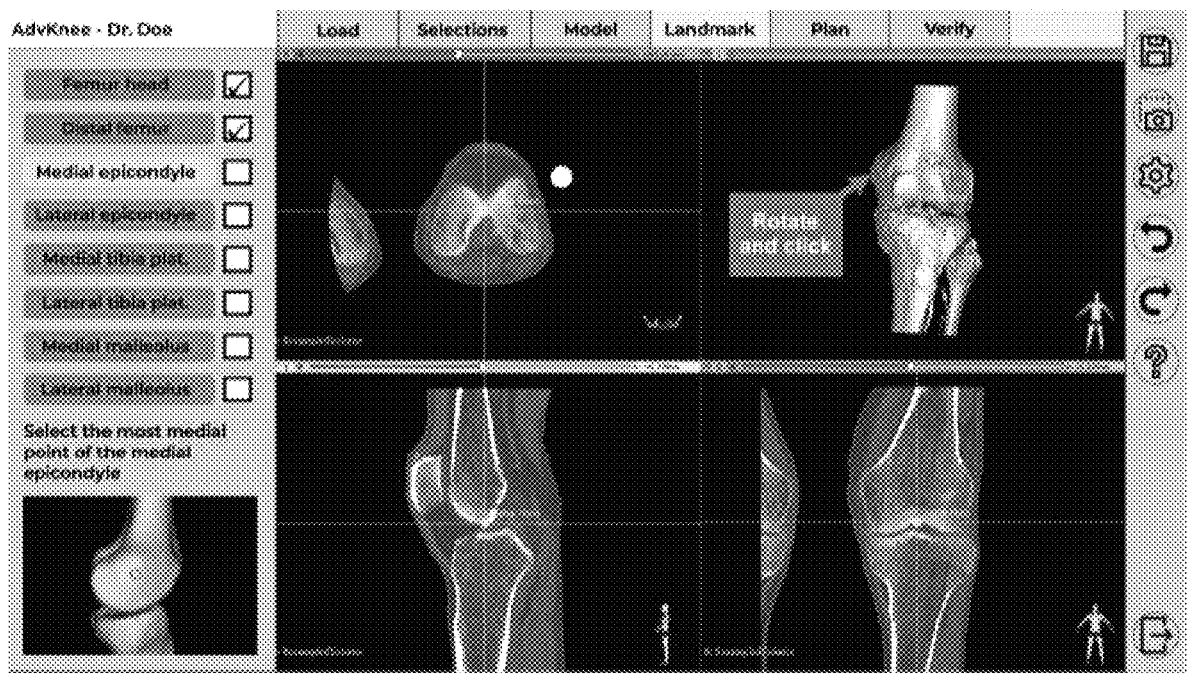
FIG. 72 is a sample user-interface of an application for use with the system of FIG. 1 presented in color, which facilitates anatomical landmarking for another portion of the anatomy of the subject.
Figure 73:
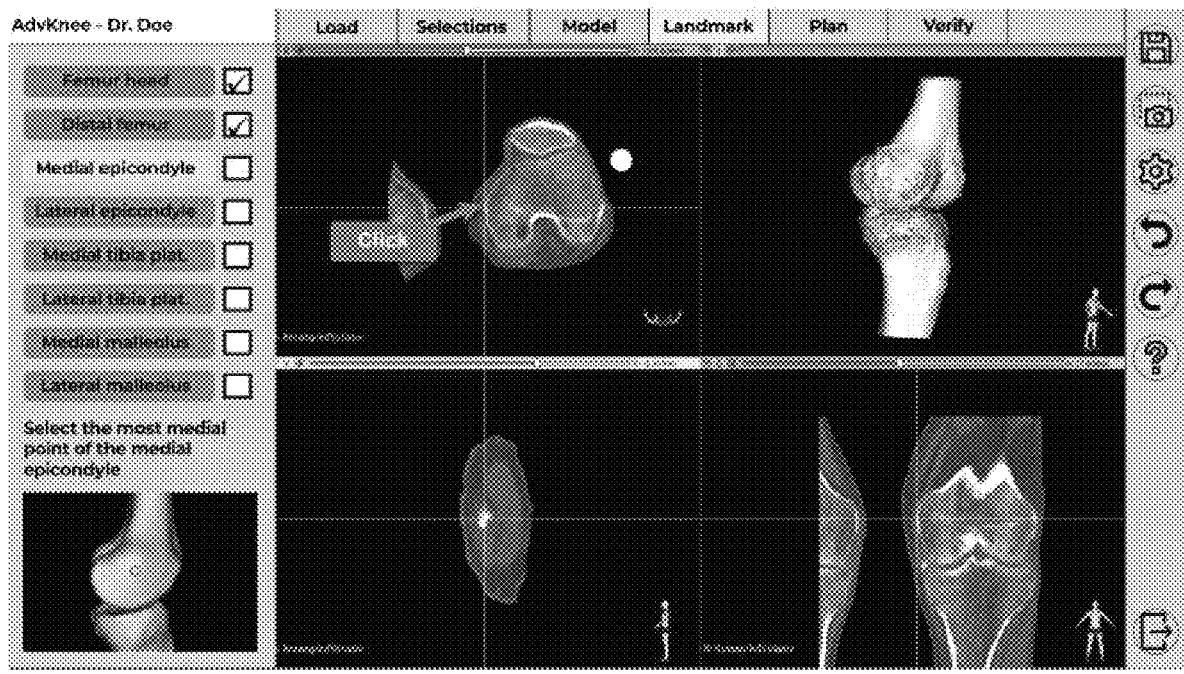
FIG. 73 is a sample user-interface of an application for use with the system of FIG. 1 presented in color, which facilitates the placement of landmark points for a portion of the anatomy.
Figure 74:
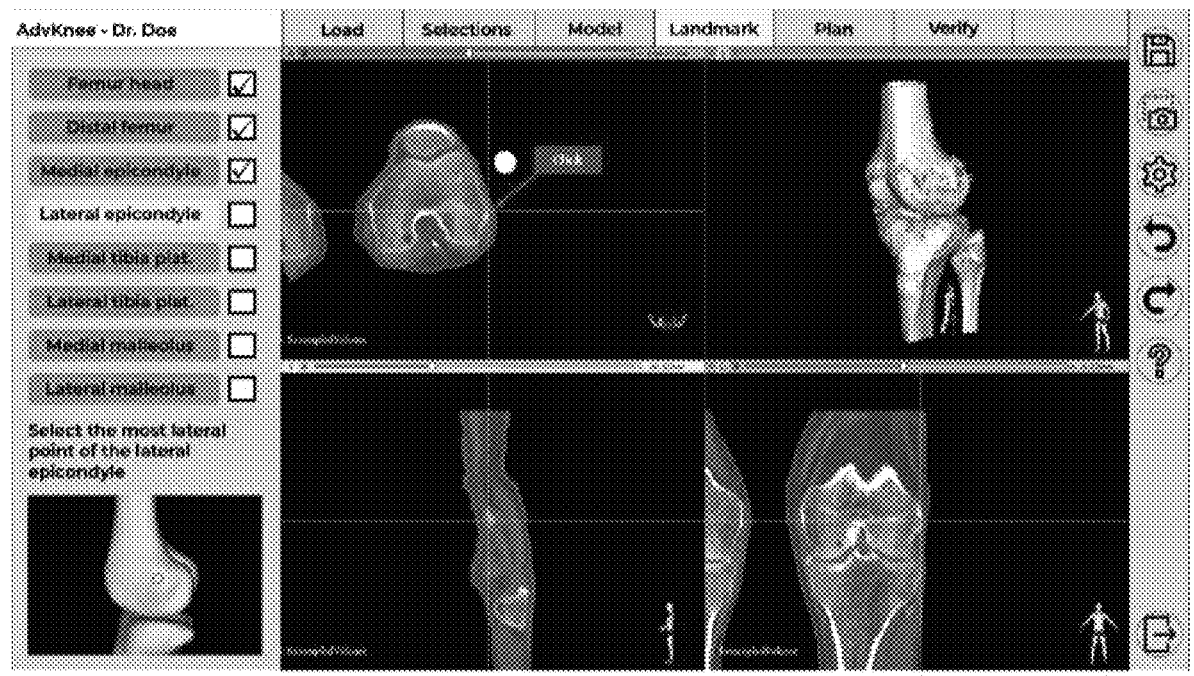
FIG. 74 is a sample user-interface of an application for use with the system of FIG. 1 presented in color, which facilitates anatomical landmarking for another portion of the anatomy of the subject.
Figure 75:
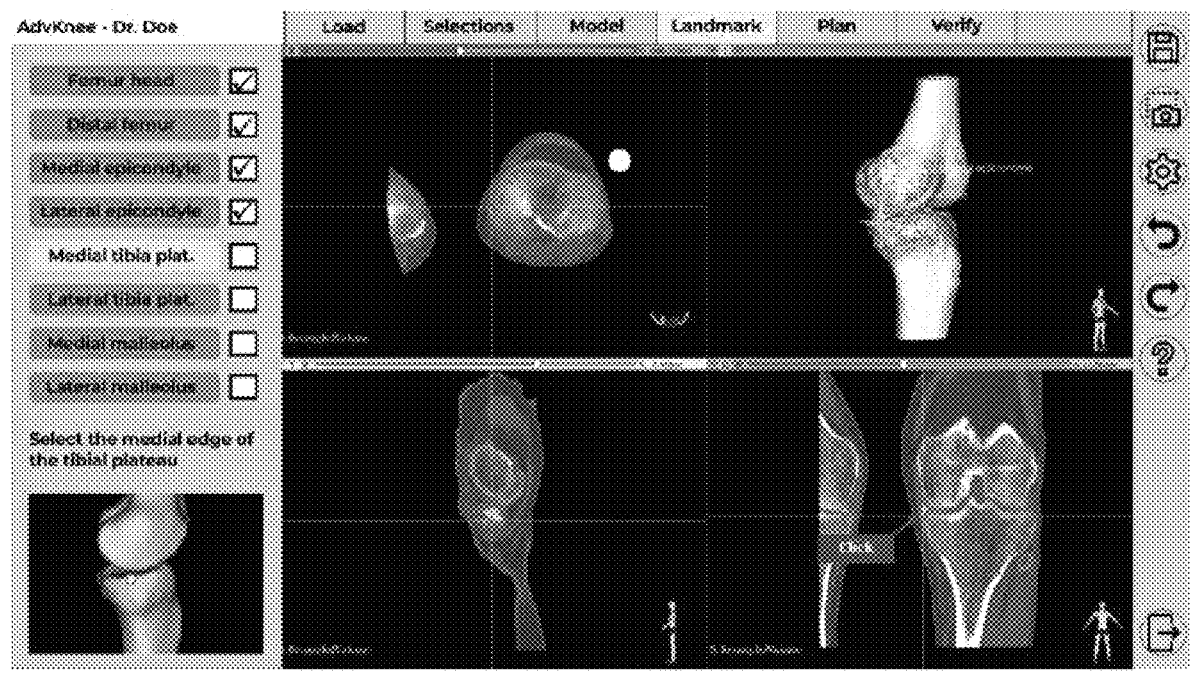
FIG. 75 is a sample user-interface of an application for use with the system of FIG. 1 presented in color, which facilitates anatomical landmarking for another portion of the anatomy of the subject.
Figure 76:
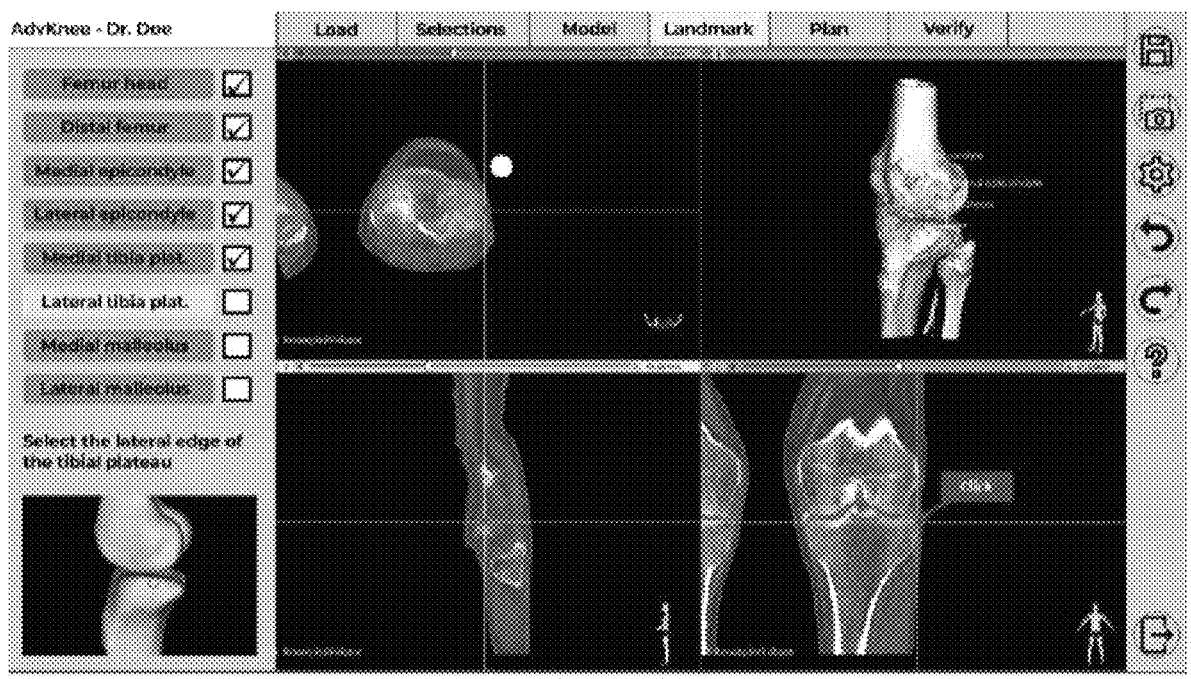
FIG. 76 is a sample user-interface of an application for use with the system of FIG. 1 presented in color, which facilitates anatomical landmarking for another portion of the anatomy of the subject.
Figure 77:
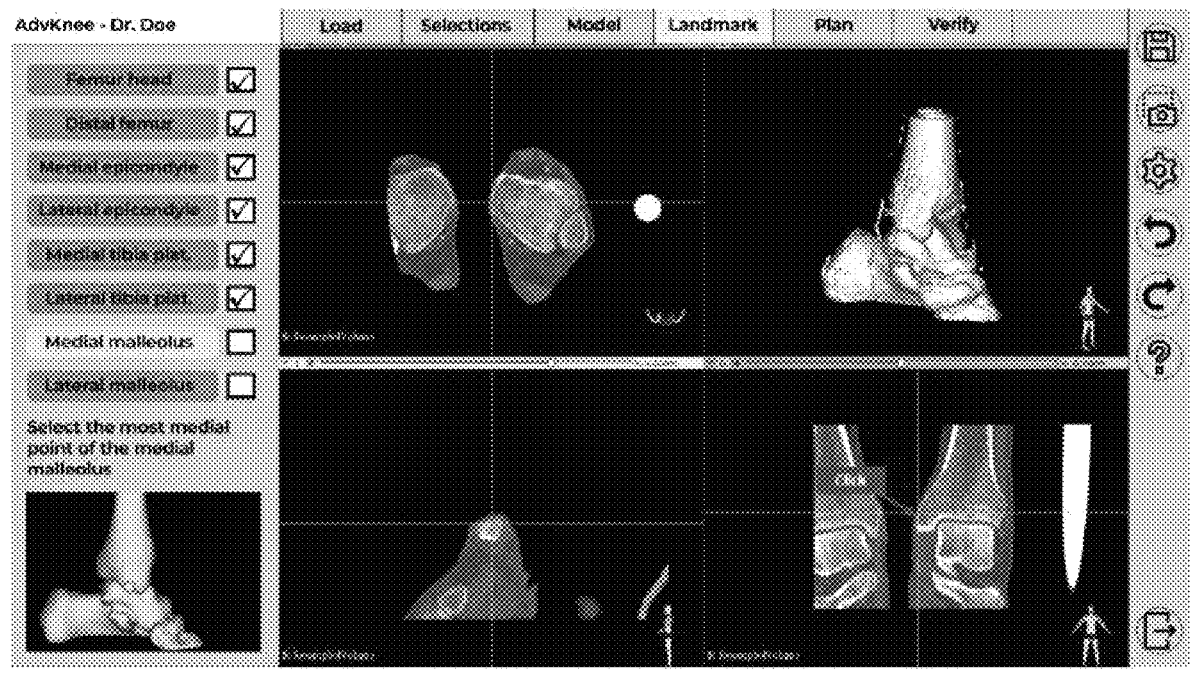
FIG. 77 is a sample user-interface of an application for use with the system of FIG. 1 presented in color, which facilitates anatomical landmarking for another portion of the anatomy of the subject.
Figure 78:
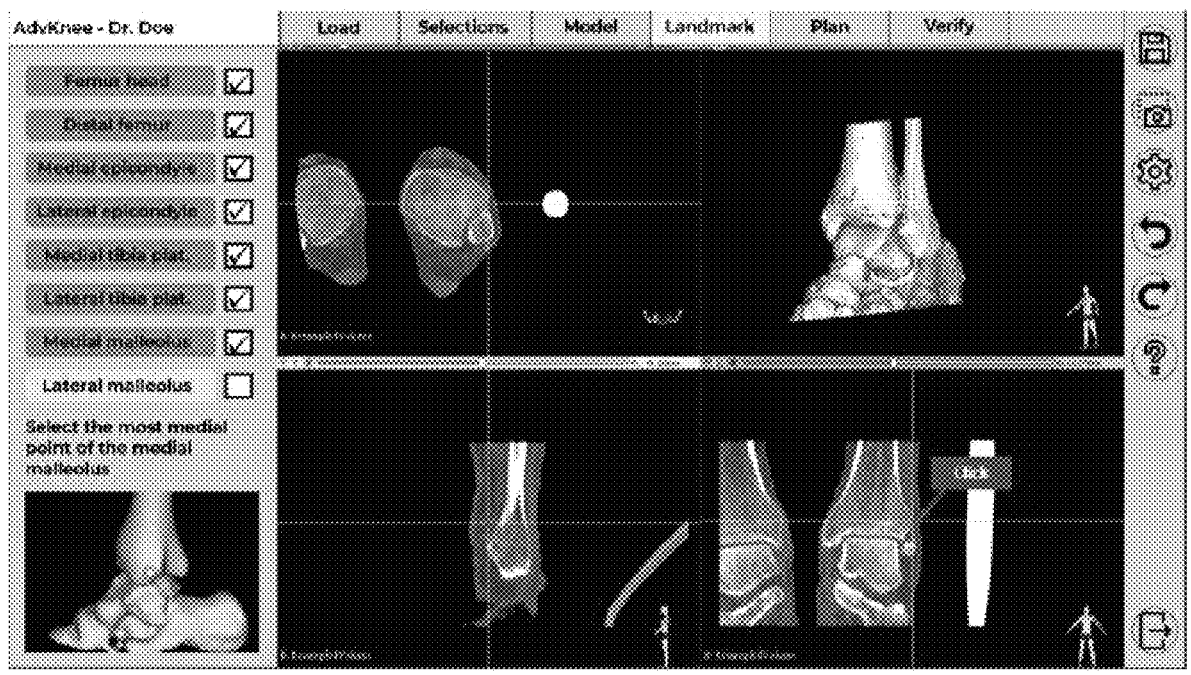
FIG. 78 is a sample user-interface of an application for use with the system of FIG. 1 presented in color, which facilitates anatomical landmarking for another portion of the anatomy of the subject.
Figure 79:
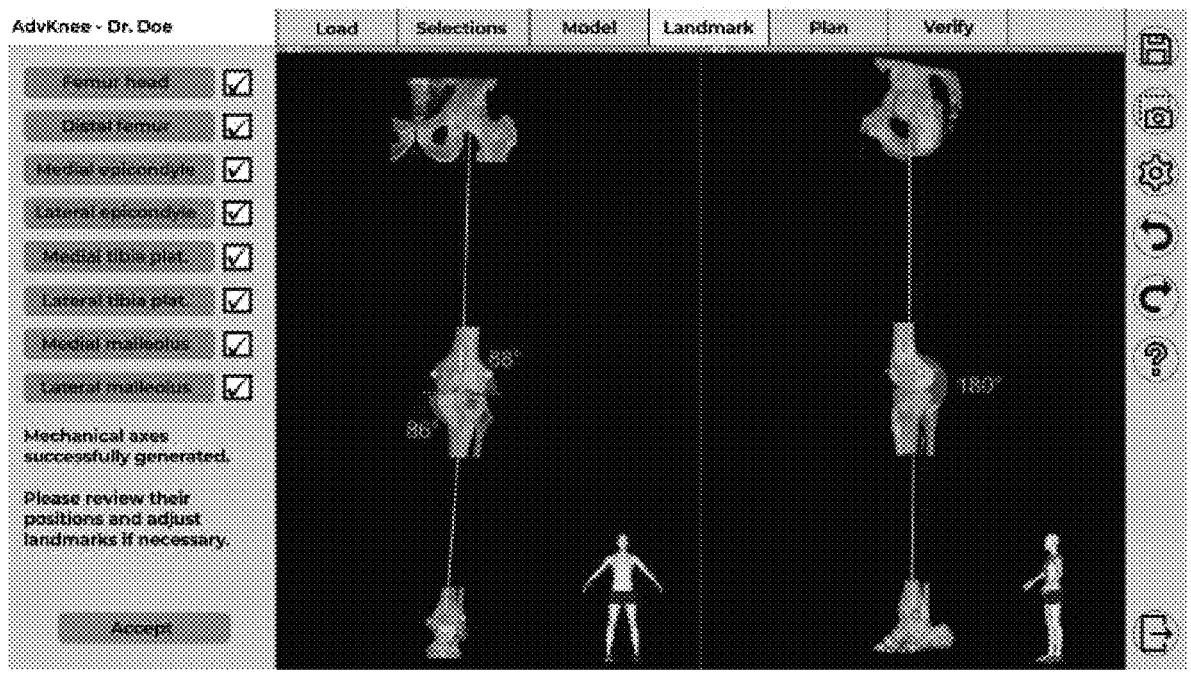
FIG. 79 is a sample user-interface of an application for use with the system of FIG. 1 presented in color, which facilitates a final review of landmarks prior to implant position planning.
Figure 80:
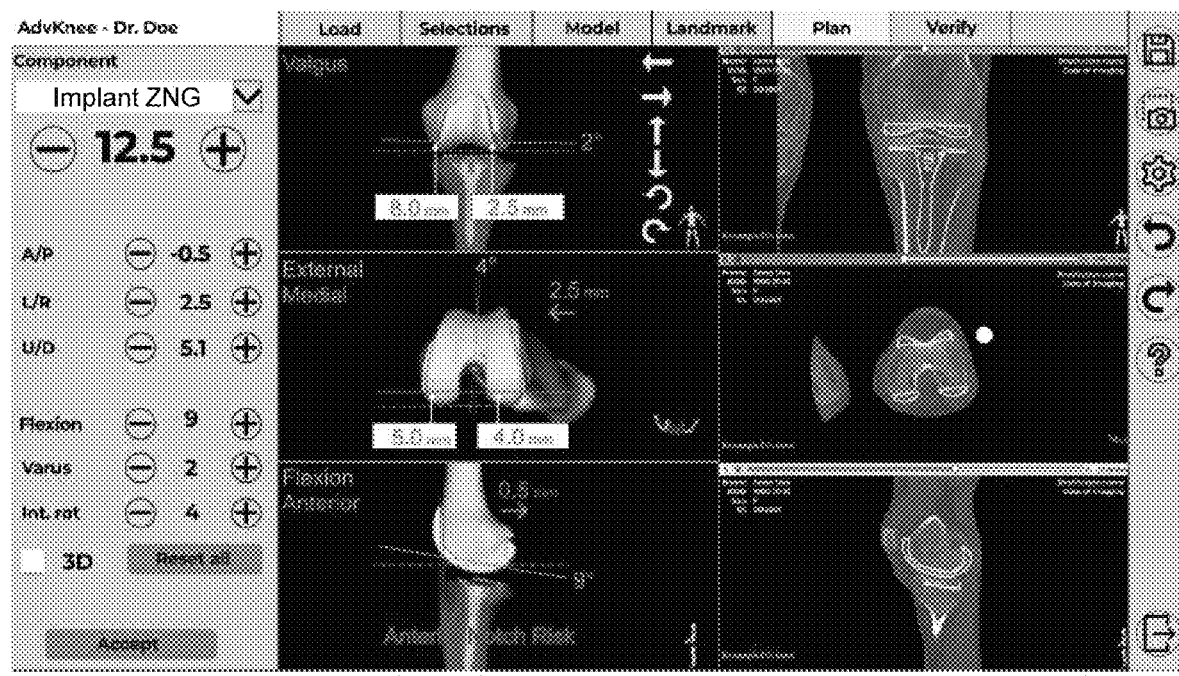
FIG. 80 is a sample user-interface of an application for use with the system of FIG. 1 presented in color, which facilitates implant planning for a component.
Figure 81:
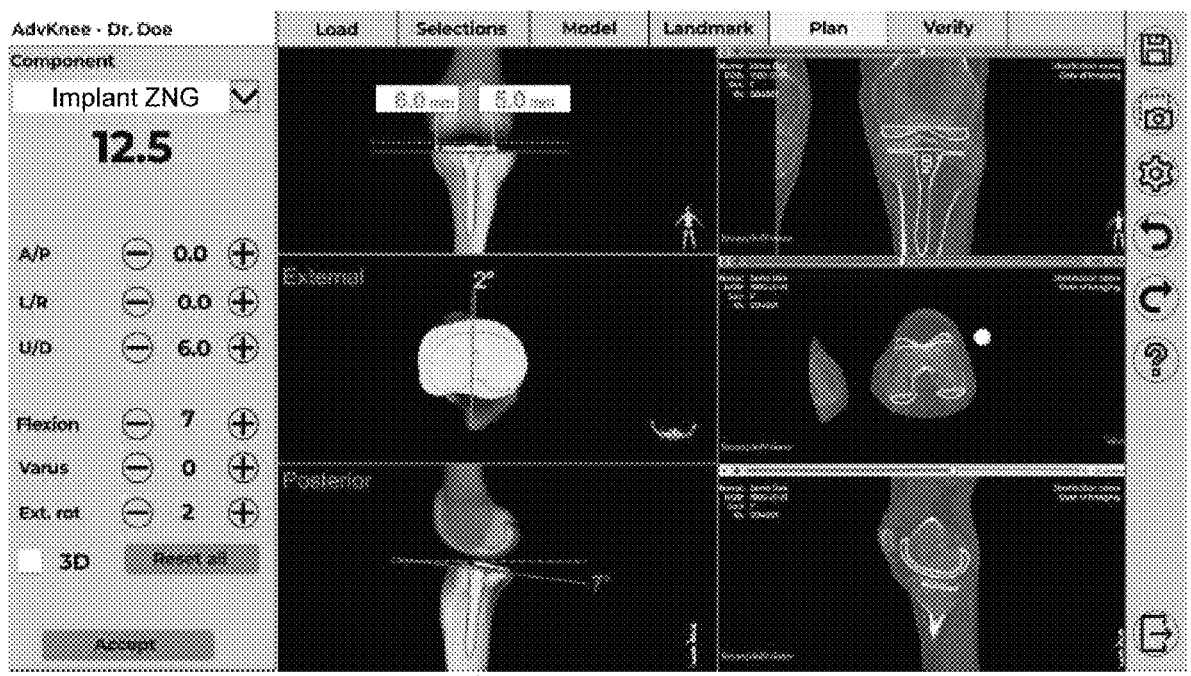
FIG. 81 is a sample user-interface of an application for use with the system of FIG. 1 presented in color, which facilitates implant planning for another component.
Figure 82:
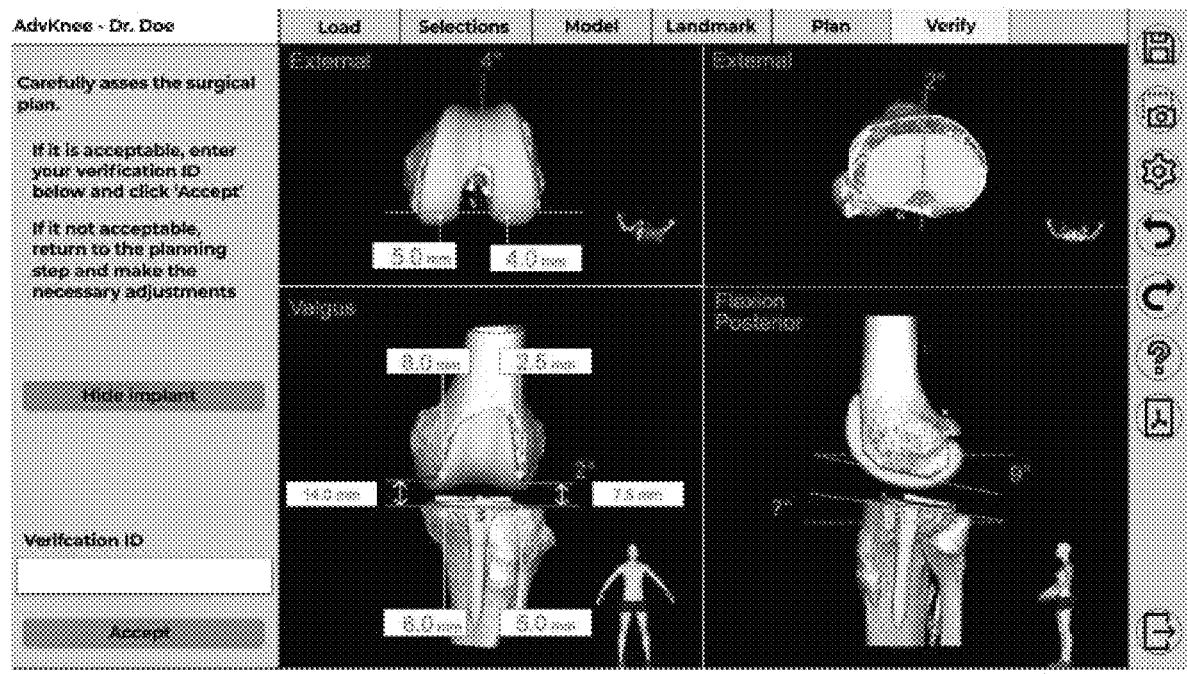
FIG. 82 is a sample user-interface of an application for use with the system of FIG. 1 presented in color, which facilitates verification and approval of implant positioning.
Figure 83:
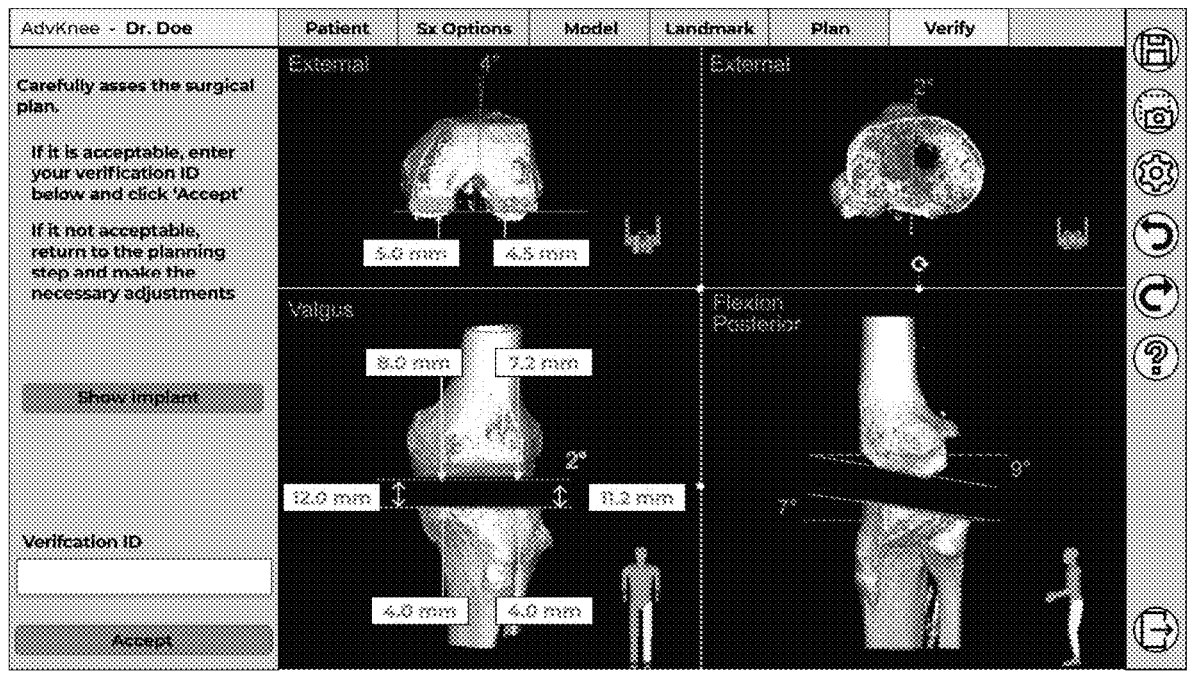
FIG. 83 is a sample user-interface of an application for use with the system of FIG. 1 presented in color, which provides a view option to hide implants to observe cut lines in relation to the subject's anatomy during the verification and approval of implant positioning.
Figure 84:
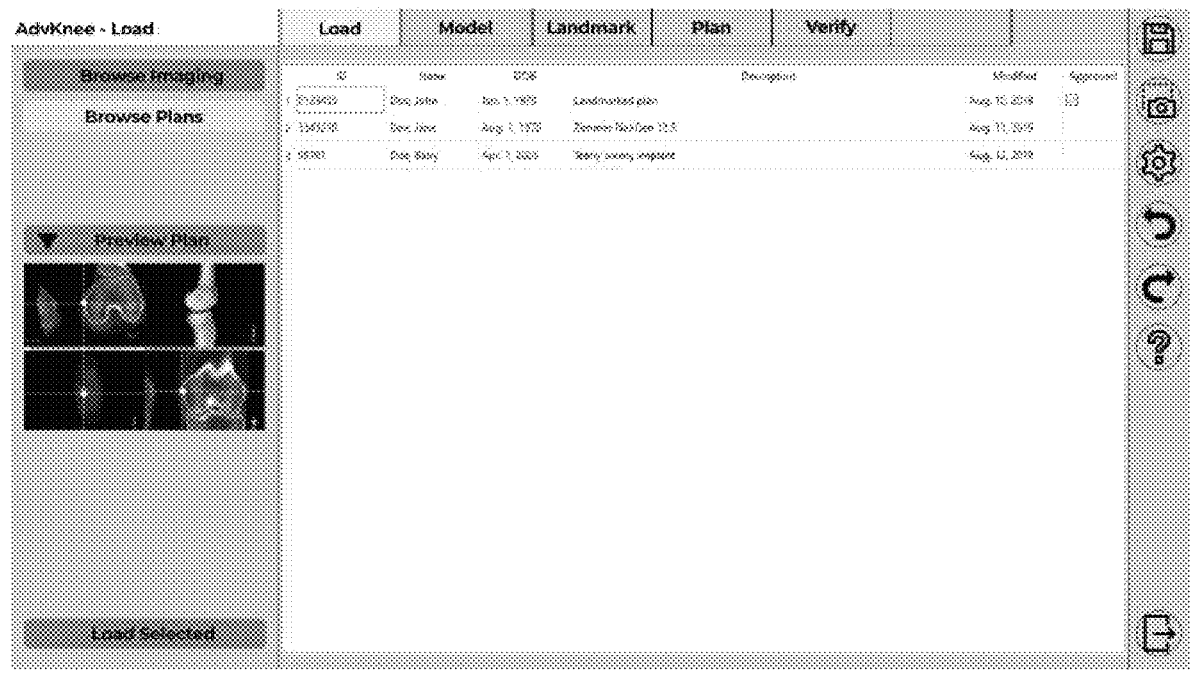
FIG. 84 is a sample user-interface of an application for use with the system of FIG. 1 presented in color, which provides the ability to initiate new plans or edit existing plans.
Figure 85:
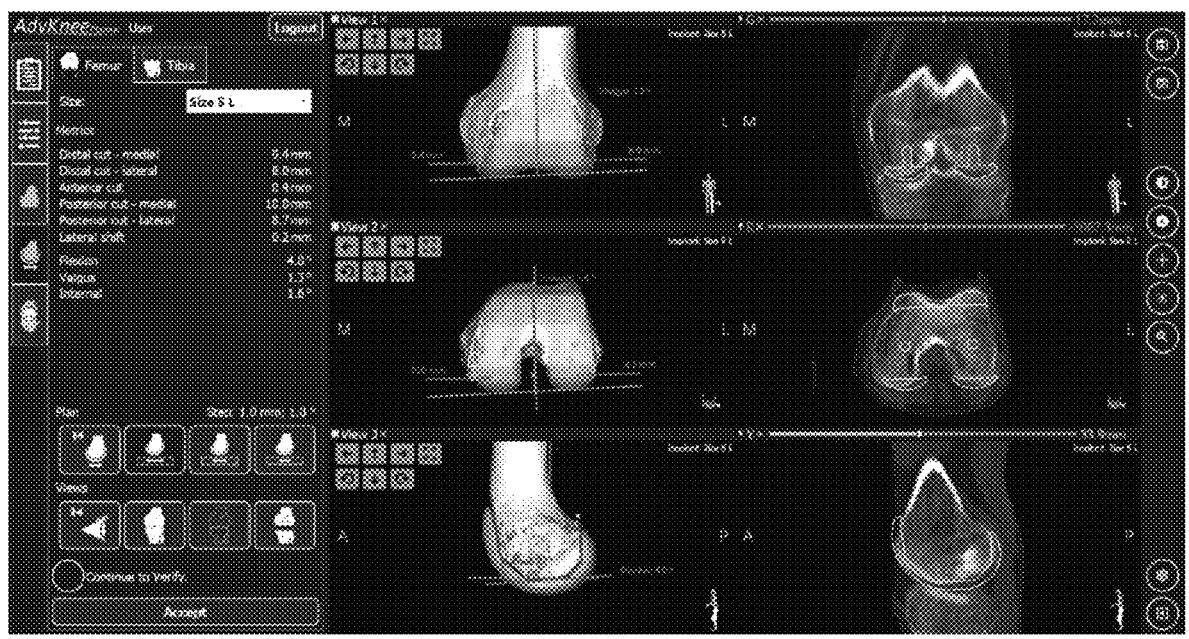
FIG. 85 is a sample user interface for use with the system of FIG. 1 presented in color and for facilitating surgical planning and guidance with three-dimensional visualization according to an embodiment of the present disclosure.
Figure 86:
FIG. 86 is a sample user-interface of an application for use with the system of FIG. 1 presented in color, which enables a user to authenticate into the system and access features and functionality of the system.
Figure 87:
FIG. 87 is a sample user-interface of an application for use with the system of FIG. 1 presented in color, which enables a user to browse various images stored by or made accessible to the system.
Figure 88:
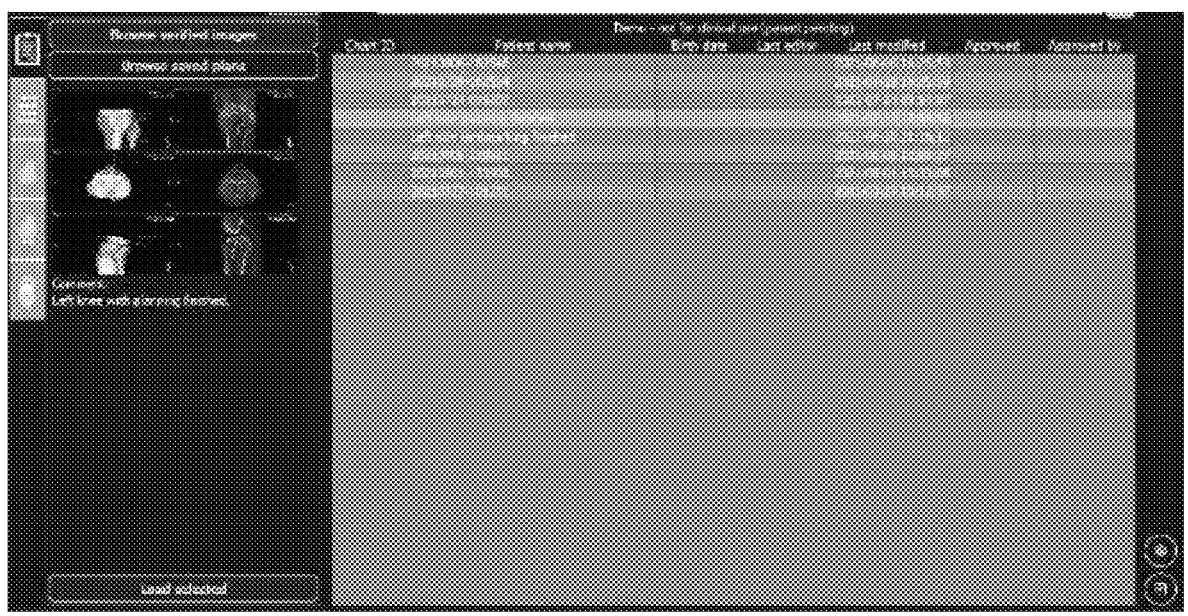
FIG. 88 is a sample user-interface of an application for use with the system of FIG. 1 presented in color, which enables a user to browse various surgical plans stored by or made accessible to the system.
Figure 89:
FIG. 89 is a sample user-interface of an application for use with the system of FIG. 1 presented in color, which enables selection of various options.
Figure 90:
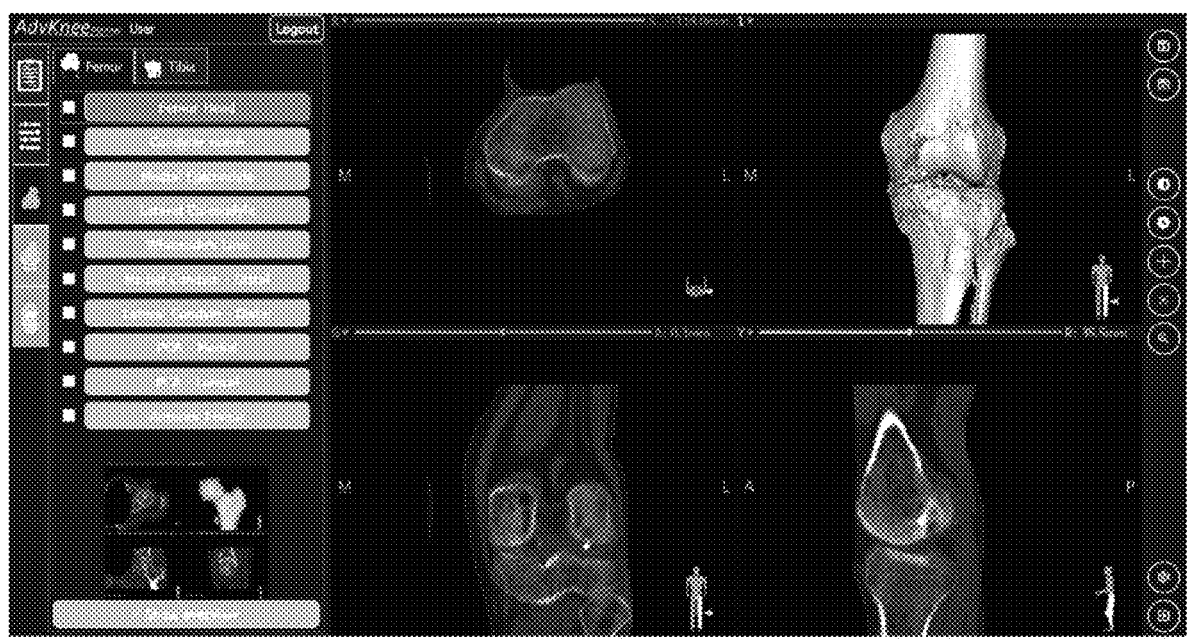
FIG. 90 is a sample user-interface of an application for use with the system of FIG. 1 presented in color, which facilitates the selection of landmark points for an anatomy of interest.
Figure 91:
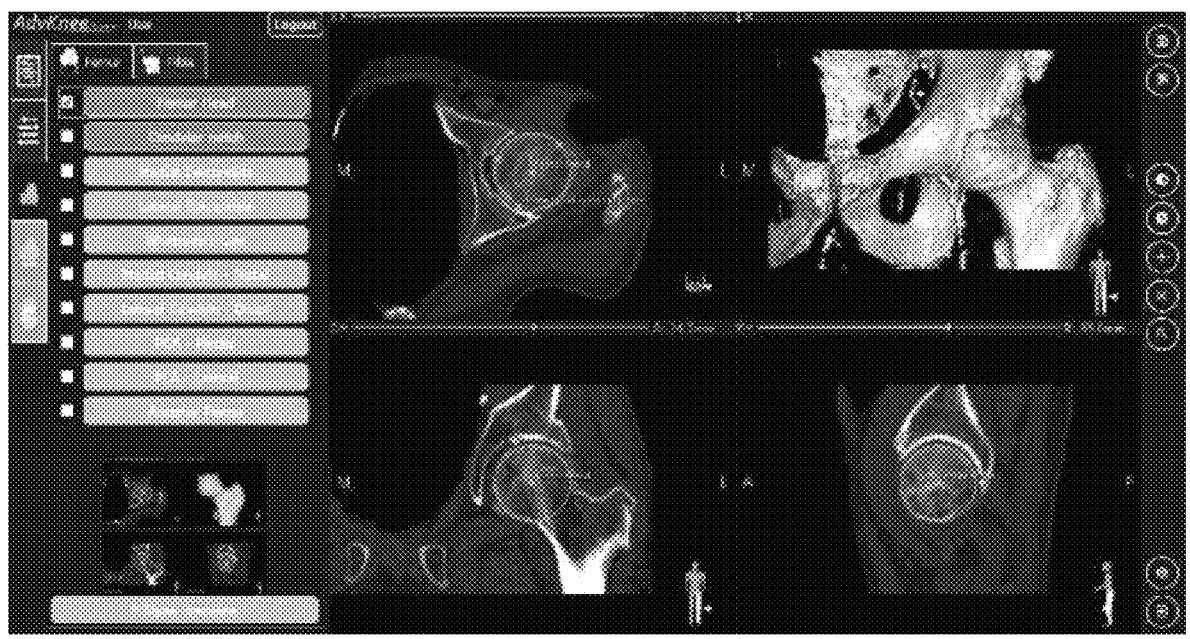
FIG. 91 is a sample user-interface of an application for use with the system of FIG. 1 presented in color, which facilitates femoral landmarking using a femur head.
Figure 92:
FIG. 92 is a sample user-interface of an application for use with the system of FIG. 1 presented in color, which facilitates femoral landmarking using a condylar notch.
Figure 93:
FIG. 93 is a sample user-interface of an application for use with the system of FIG. 1 presented in color, which facilitates femoral landmarking using epicondyles.
Figure 94:
FIG. 94 is a sample user-interface of an application for use with the system of FIG. 1 presented in color, which facilitates femoral landmarking using Whiteside's Line.
Figure 95:
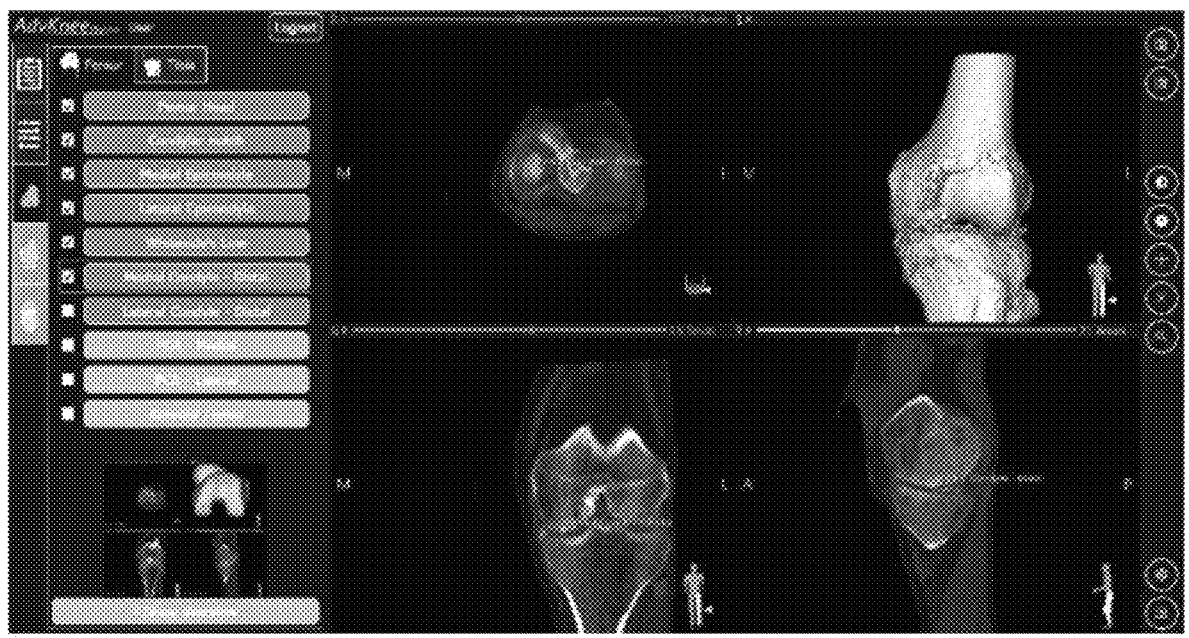
FIG. 95 is a sample user-interface of an application for use with the system of FIG. 1 presented in color, which facilitates femoral landmarking using distal condyles.
Figure 96:
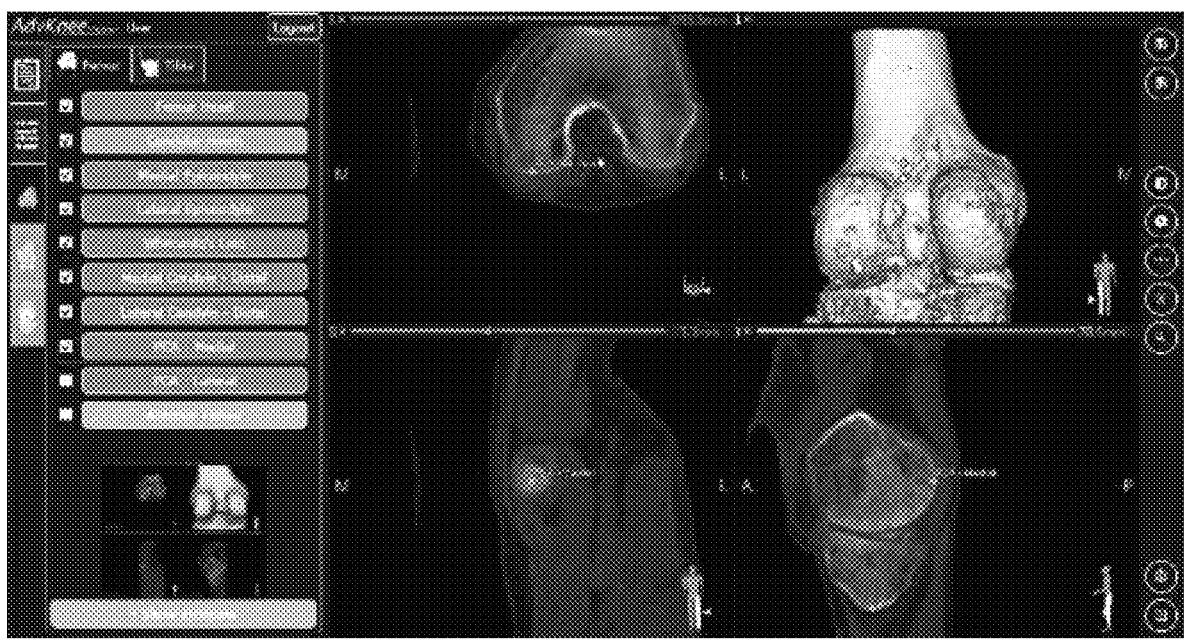
FIG. 96 is a sample user-interface of an application for use with the system of FIG. 1 presented in color, which facilitates femoral landmarking using posterior condylar axis points.
Figure 97:
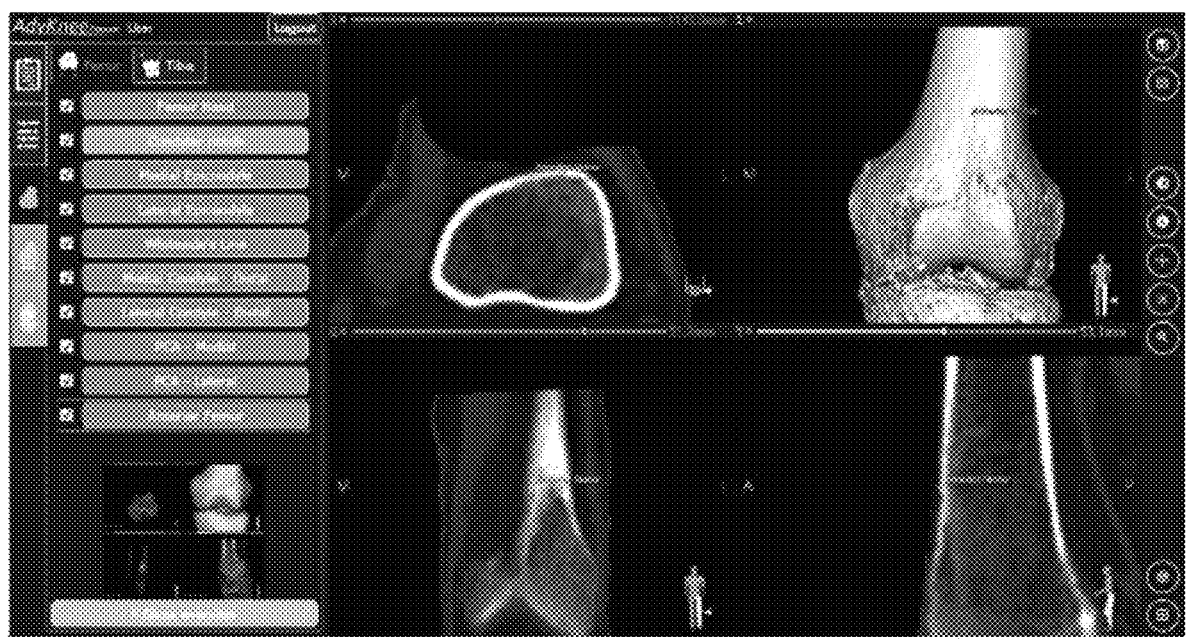
FIG. 97 is a sample user-interface of an application for use with the system of FIG. 1 presented in color, which facilitates femoral landmarking using an anterior femur.
Figure 98:
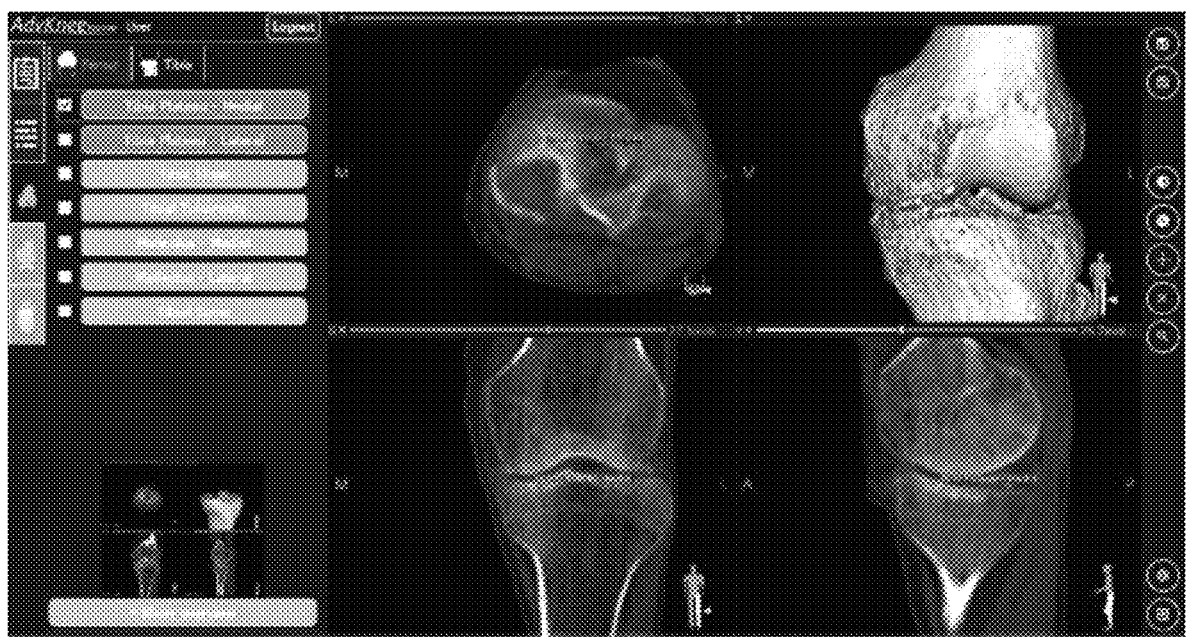
FIG. 98 is a sample user-interface of an application for use with the system of FIG. 1 presented in color, which facilitates tibial landmarking using tibia plateaus.
Figure 99:
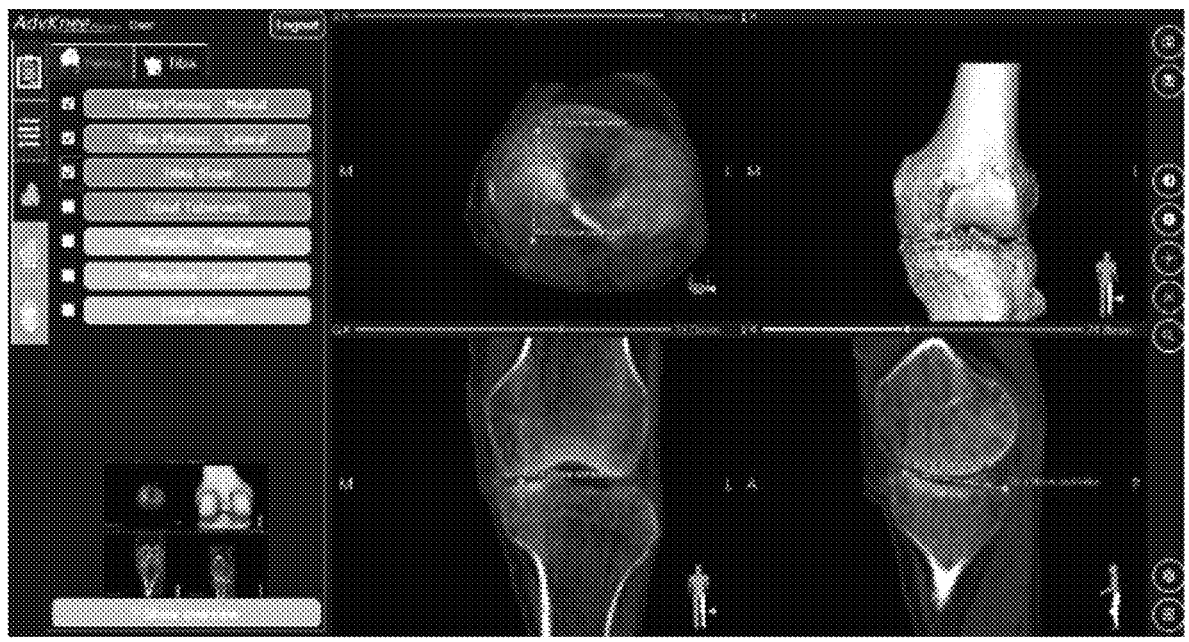
FIG. 99 is a sample user-interface of an application for use with the system of FIG. 1 presented in color, which facilitates tibial landmarking using a tibia slope.
Figure 100:
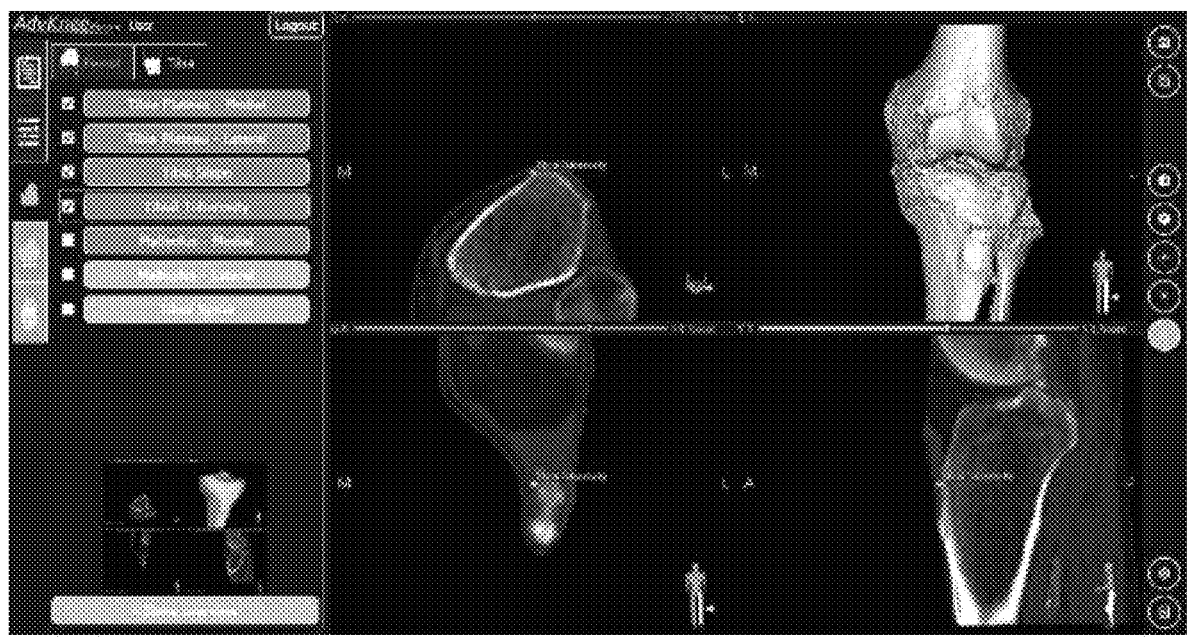
FIG. 100 is a sample user-interface of an application for use with the system of FIG. 1 presented in color, which facilitates tibial landmarking using tuberosity.
Figure 101:
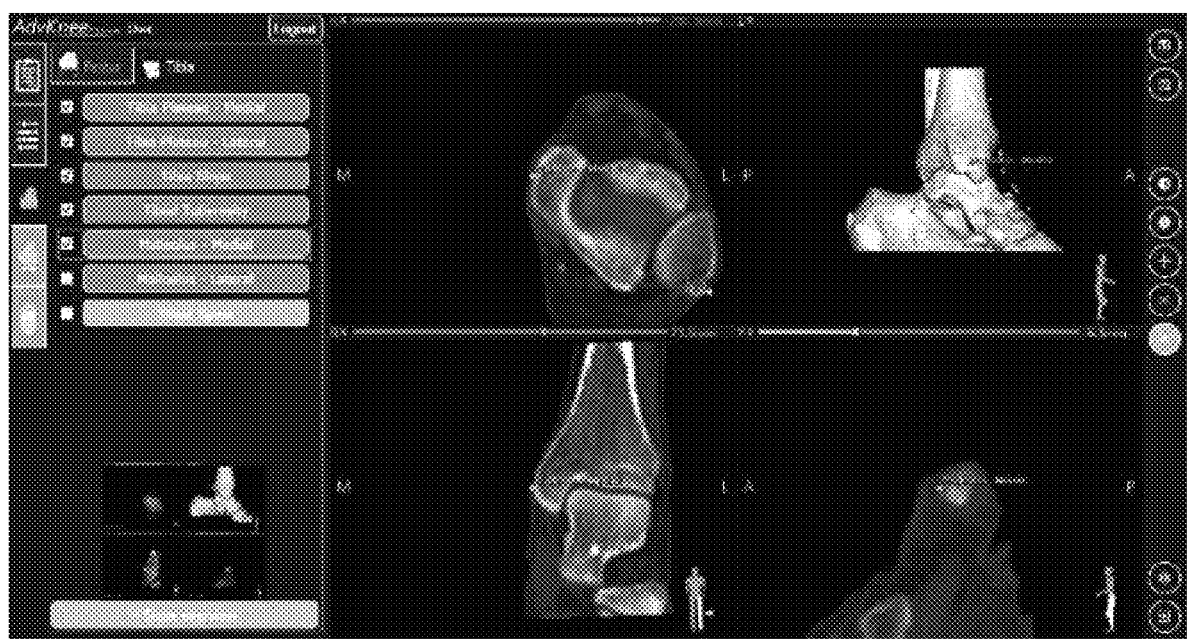
FIG. 101 is a sample user-interface of an application for use with the system of FIG. 1 presented in color, which facilitates tibial landmarking using malleoli.
Figure 102:
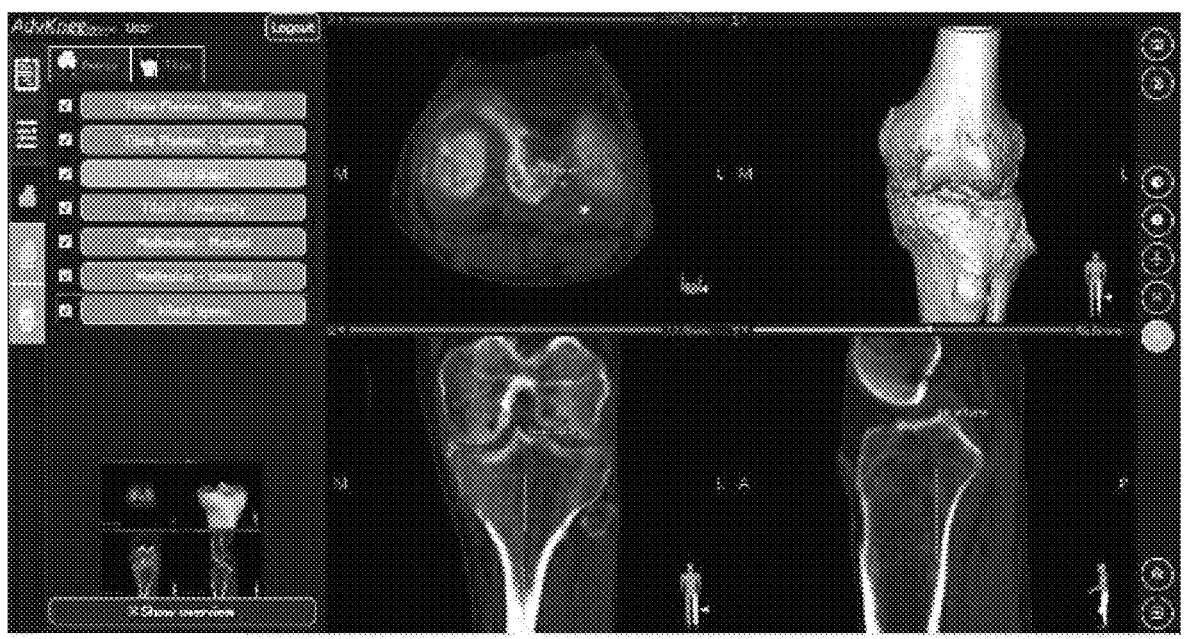
FIG. 102 is a sample user-interface of an application for use with the system of FIG. 1 presented in color, which facilitates tibial landmarking using a tibial spine.
Figure 103:
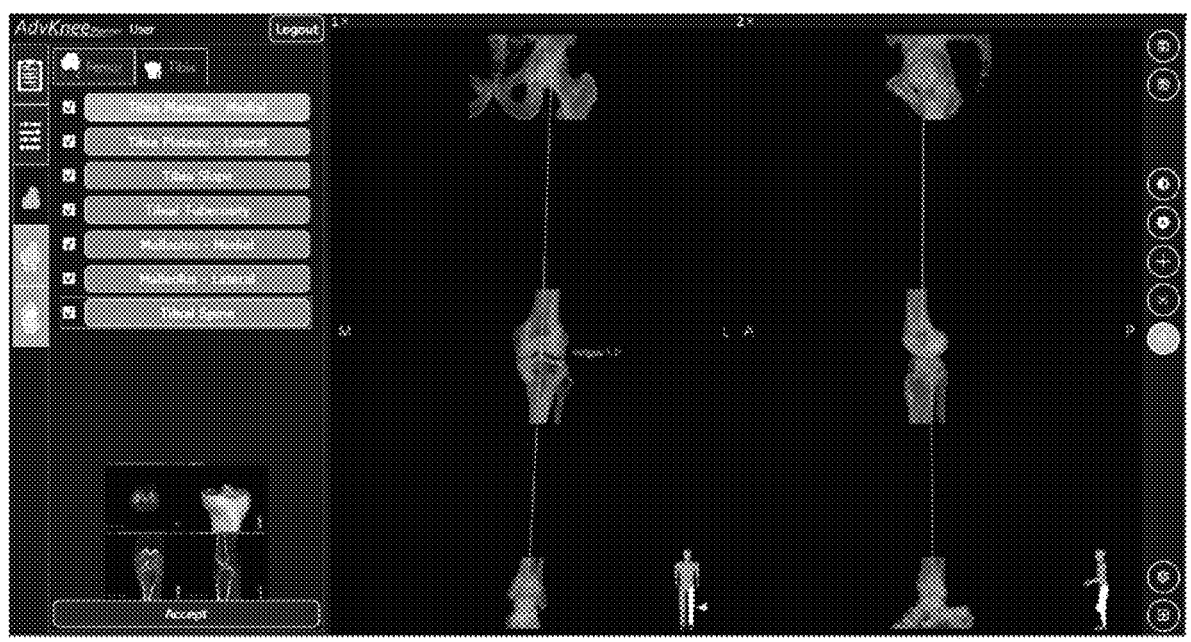
FIG. 103 is a sample user-interface of an application for use with the system of FIG. 1 presented in color, which provides a limb alignment overview once anatomical landmarks are defined.
Figure 104:
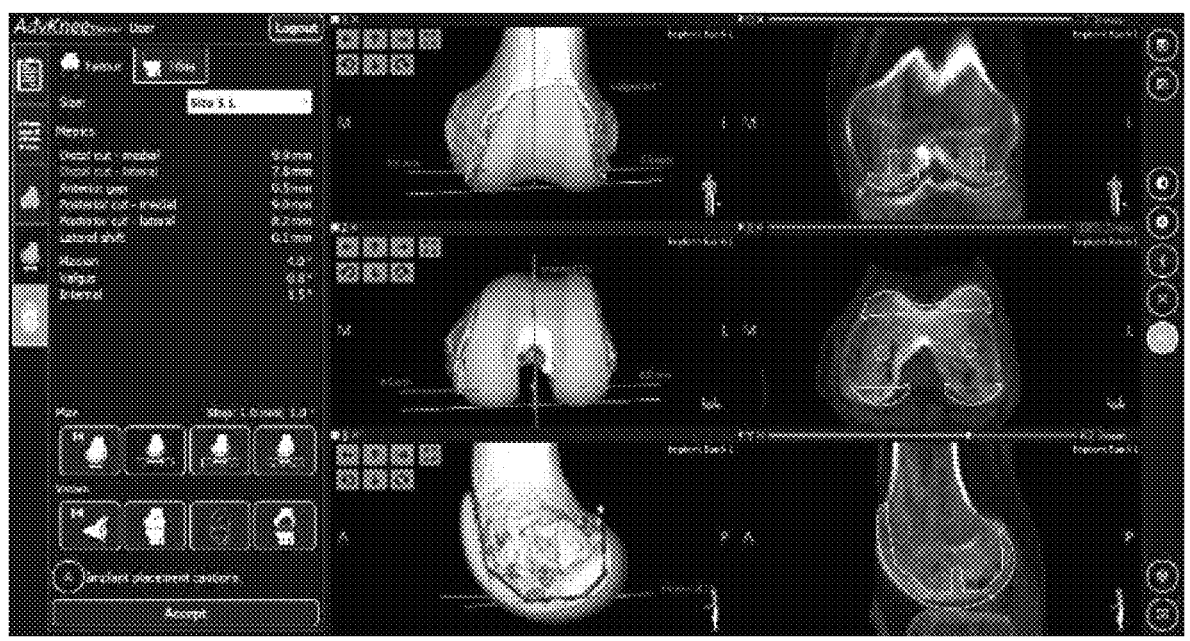
FIG. 104 is a sample user-interface of an application for use with the system of FIG. 1 presented in color, which facilitates surgical planning.
Figure 105:
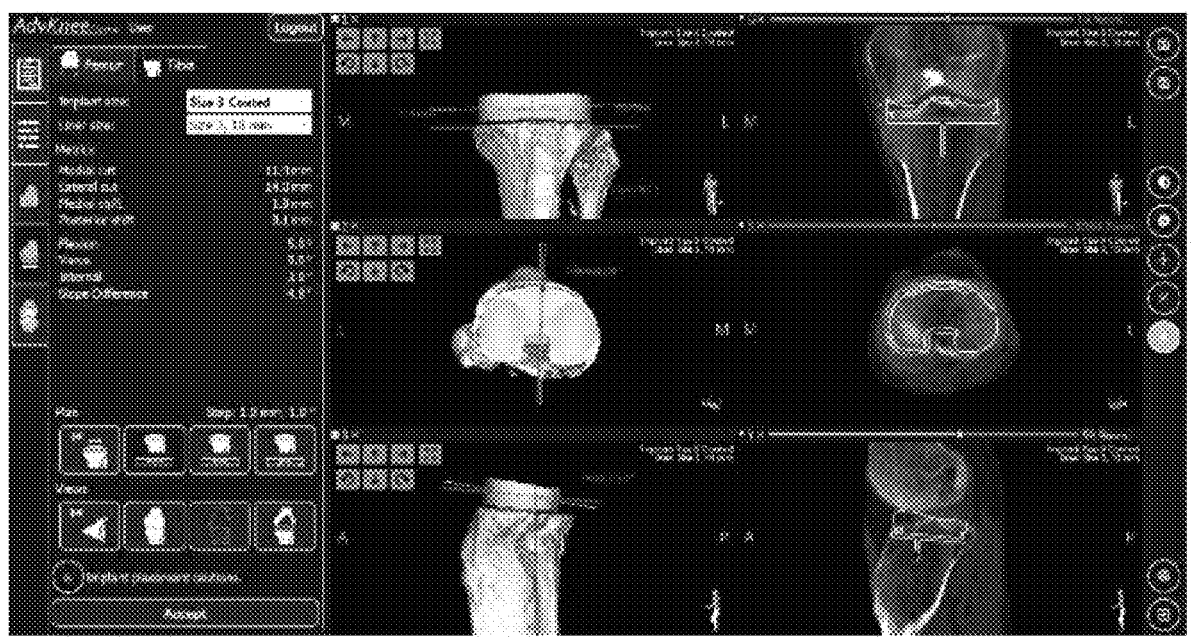
FIG. 105 is a sample user-interface of an application for use with the system of FIG. 1 presented in color, which facilitates selection of implant positioning for an implant.
Figure 106:
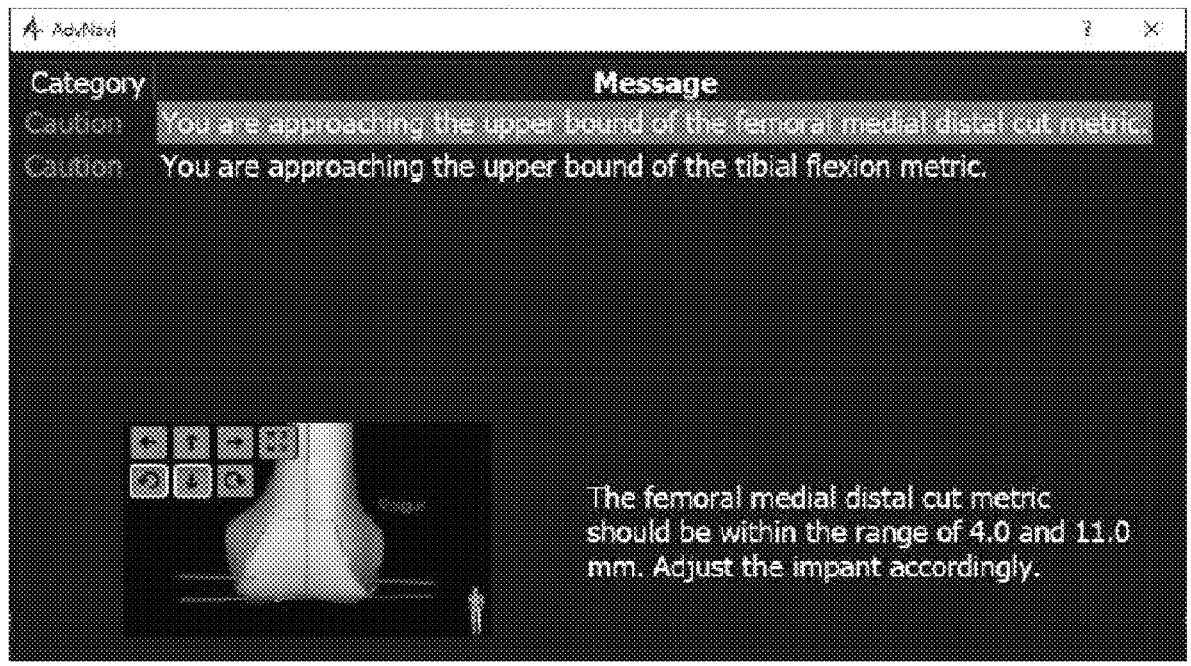
FIG. 106 is a sample user-interface of an application for use with the system of FIG. 1 presented in color, which provides implant positioning hints and alerts.
Figure 107:
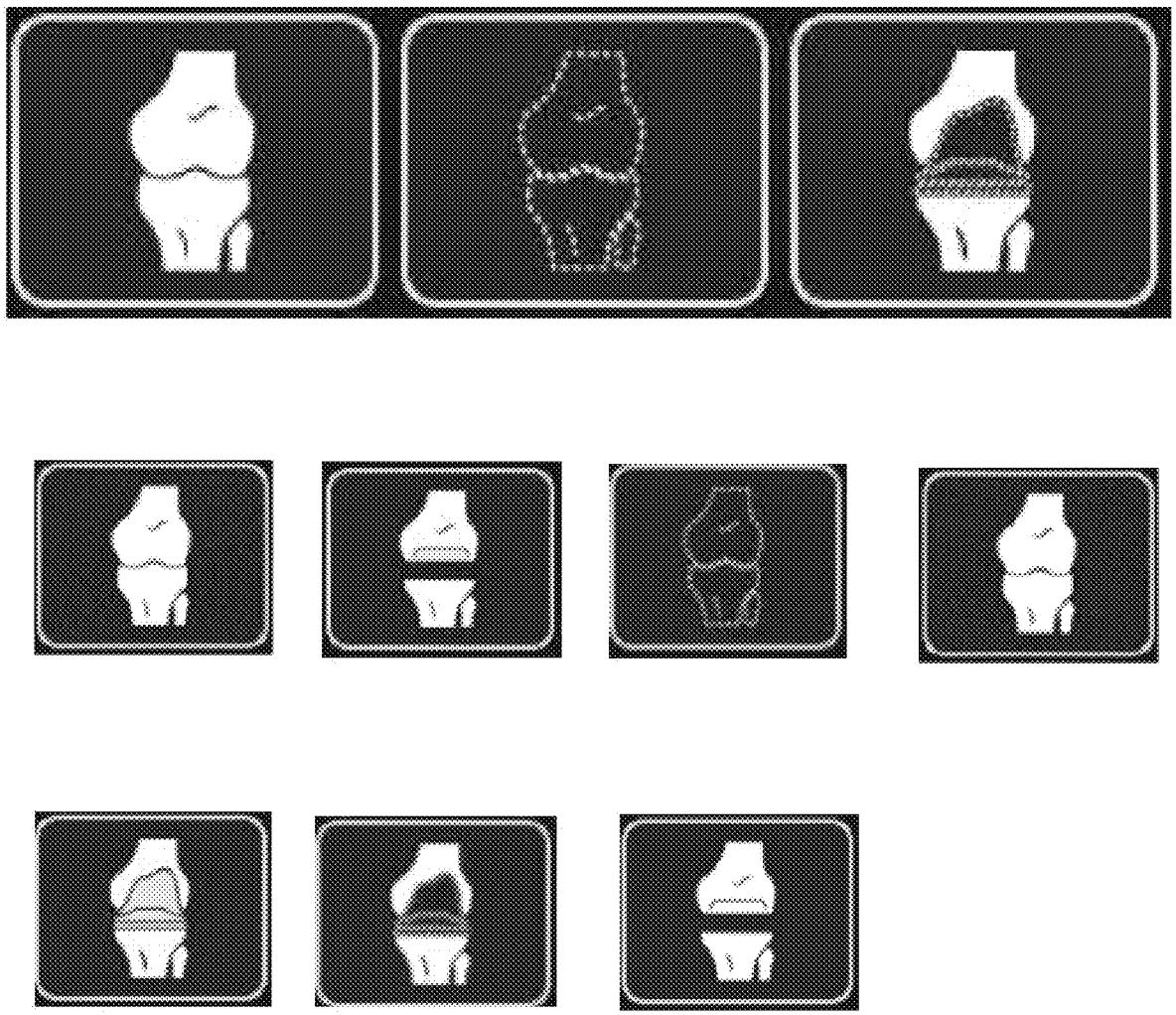
FIG. 107 features an assortment of various controls for adjusting the view of bone cuts and implants presented in color.
Figure 108:
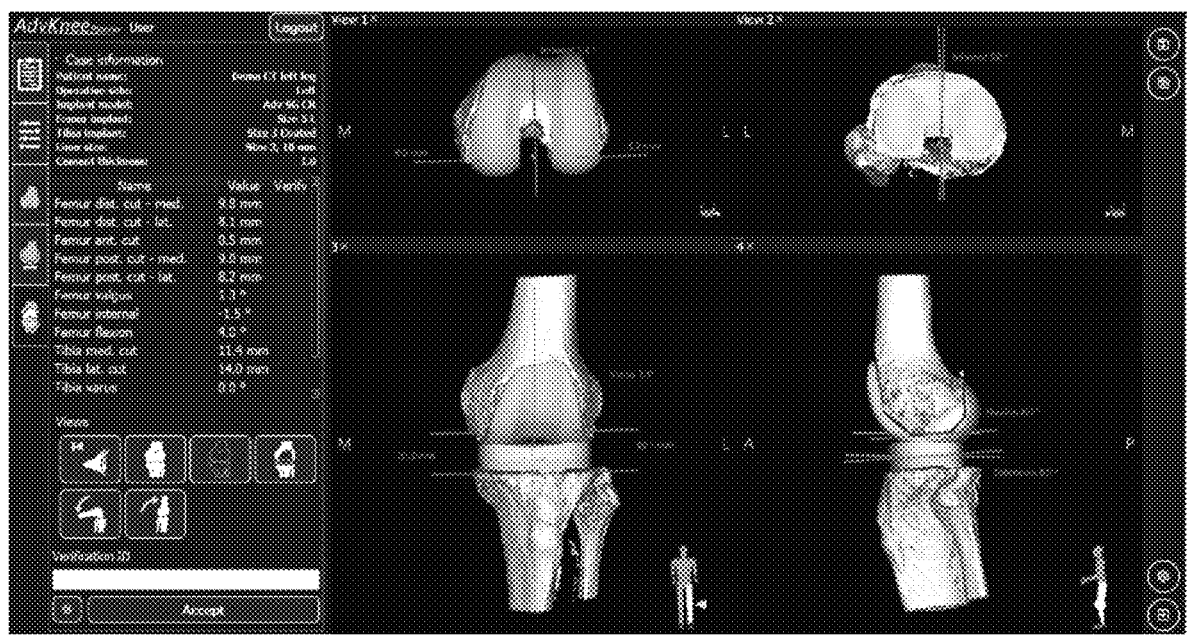
FIG. 108 is a sample user-interface of an application for use with the system of FIG. 1 presented in color, which facilitates verification the planned implant placement for an implant to be implanted onto a subject.

As shown in FIG. 1 and referring also to FIGS. 1-56, a system 100 for providing surgical planning and guidance with three-dimensional visualization is disclosed. Notably, the system 100 may be configured to support, but is not limited to supporting, surgical navigation systems and services, medical systems and services, artificial intelligence services and systems, machine learning services and systems, content delivery services, surveillance and monitoring services, cloud computing services, satellite services, telephone services, voice-over-internet protocol services (VoIP), software as a service (SaaS) applications, platform as a service (PaaS) applications, gaming applications and services, social media applications and services, operations management applications and services, productivity applications and services, mobile applications and services, and/or any other computing applications and services. Notably, the system 100 may include a first user 101, who may utilize a first user device 102 to access data, content, and services, or to perform a variety of other tasks and functions. As an example, the first user 101 may utilize first user device 102 to transmit signals to access various online services and content, such as those available on an internet, on other devices, and/or on various computing systems. As another example, the first user device 102 may be utilized to access an application that provides the operative functions of the system and/or provides surgical navigation capabilities. In certain embodiments, the first user 101 may be a physician, such as a surgeon, a surgical planning specialist (e.g. from an implant company, a hospital, and/or other institution), a clinical technician, a passive robot, an active robot, a humanoid, a program, a computer, any type of user, or a combination thereof. In certain embodiments, the first user 101 may be one or more first users 101. The first user device 102 may include a memory 103 that includes instructions, and a processor 104 that executes the instructions from the memory 103 to perform the various operations that are performed by the first user device 102. In certain embodiments, the processor 104 may be hardware, software, or a combination thereof. The first user device 102 may also include an interface 105 (e.g. screen, monitor, graphical user interface, etc.) that may enable the first user 101 to interact with various applications executing on the first user device 102 and to interact with the system 100. In certain embodiments, the first user device 102 may be and/or may include a computer, any type of sensor, a surgical navigation station, a laptop, a set-top-box, a tablet device, a phablet, a server, a mobile device, a smartphone, a smart watch, and/or any other type of computing device. Illustratively, the first user device 102 is shown as a smartphone device in FIG. 1. In certain embodiments, the first user device 102 may be utilized by the first user 101 to control the operative functionality of the system 100.

In addition to using first user device 102, the first user 101 may also utilize and/or have access to additional user devices. As with first user device 102, the first user 101 may utilize the additional user devices to transmit signals to access various online services and content. The additional user devices may include memories that include instructions, and processors that executes the instructions from the memories to perform the various operations that are performed by the additional user devices. In certain embodiments, the processors of the additional user devices may be hardware, software, or a combination thereof. The additional user devices may also include interfaces that may enable the first user 101 to interact with various applications executing on the additional user devices and to interact with the system 100. In certain embodiments, the additional user devices may be and/or may include a computer, any type of sensor, surgical navigation devices, a laptop, a set-top-box, a tablet device, a phablet, a server, a mobile device, a smartphone, a smart watch, and/or any other type of computing device, and/or any combination thereof.

The first user device 102 and/or additional user devices may belong to and/or form a communications network. In certain embodiments, the communications network may be a local, mesh, or other network that enables and/or facilitates various aspects of the functionality of the system 100. In certain embodiments, the communications network may be formed between the first user device 102 and additional user devices through the use of any type of wireless or other protocol and/or technology. For example, user devices may communicate with one another in the communications network by utilizing any protocol and/or wireless technology, satellite, fiber, or any combination thereof. Notably, the communications network may be configured to communicatively link with and/or communicate with any other network of the system 100 and/or outside the system 100.

In certain embodiments, the first user device 102 and additional user devices belonging to the communications network may share and exchange data with each other via the communications network. For example, the user devices may share information relating to the various components of the user devices, information associated with images (and/or other media content) of anatomy taken by the system 100 and/or by other devices, information associated with surgical plans generated and/or modified by the system 100, information identifying the locations of the user devices, information indicating the types of sensors that are contained in and/or on the user devices, information identifying the applications being utilized on the user devices, information identifying how the user devices are being utilized by a user, information identifying user profiles for users of the user devices, information identifying device profiles for the user devices, information identifying the number of devices in the communications network, information identifying devices being added to or removed from the communications network, any other information, or any combination thereof.

In addition to the first user 101, the system 100 may also include a second user 110. The second user 110 may be a subject for a surgical procedure to be conducted by the first user 101, a patient, any type of user, or a combination thereof. In certain embodiments, the second user 110 may be one or more second users 110. In certain embodiments, the first user 101 may perform some or any of the functionality of the system 100 without the need for the second user 110 and vice versa. The second user device 111 may be utilized by first user 101 (or potentially the second user 110) to transmit signals to request various types of content, services, and data provided by and/or accessible by communications network 135 or any other network in the system 100. In further embodiments, the second user 110 may be a robot, a computer, a humanoid, an animal, any type of user, or any combination thereof. The second user device 111 may include a memory 112 that includes instructions, and a processor 113 that executes the instructions from the memory 112 to perform the various operations that are performed by the second user device 111. In certain embodiments, the processor 113 may be hardware, software, or a combination thereof. The second user device 111 may also include an interface 114 (e.g. screen, monitor, graphical user interface, etc.) that may enable the first user 101 to interact with various applications executing on the second user device 111 and to interact with the system 100. In certain embodiments, the second user device 111 may be a surgical navigation device, a robot, a computer, a laptop, a set-top-box, a tablet device, a phablet, a server, a mobile device, a smartphone, a smart watch, and/or any other type of computing device. Illustratively, the second user device 111 is shown as a surgical navigation device in FIG. 1.

In certain embodiments, the first user device 102, the additional user devices, and/or the second user device 111 may have any number of software applications and/or application services stored and/or accessible thereon. For example, the first user device 102, the additional user devices, and/or the second user device 111 may include applications for controlling the operative features and functionality of the system 100, applications for controlling any device of the system 100, interactive social media applications, biometric applications, cloud-based applications, VoIP applications, other types of phone-based applications, product-ordering applications, business applications, e-commerce applications, media streaming applications, content-based applications, media-editing applications, database applications, gaming applications, internet-based applications, browser applications, mobile applications, service-based applications, productivity applications, video applications, music applications, social media applications, any other type of applications, any types of application services, or a combination thereof. In certain embodiments, the software applications may support the functionality provided by the system 100 and methods described in the present disclosure. In certain embodiments, the software applications and services may include one or more graphical user interfaces so as to enable the first and/or second users 101, 110 to readily interact with the software applications. The software applications and services may also be utilized by the first and/or second users 101, 110 to interact with any device in the system 100, any network in the system 100, or any combination thereof. In certain embodiments, the first user device 102, the additional user devices, and/or the second user device 111 may include associated telephone numbers, device identities, or any other identifiers to uniquely identify the first user device 102, the additional user devices, and/or the second user device 111.

The system 100 may also include a communications network 135. The communications network 135 may be under the control of a service provider, the first user 101, the second user 110, any other designated user, a computer, another network, or a combination thereof. The communications network 135 of the system 100 may be configured to link each of the devices in the system 100 to one another. For example, the communications network 135 may be utilized by the first user device 102 to connect with other devices within or outside communications network 135, such as, but not limited to, the second user device 111 (which may be a surgical navigation device, radiation device, or other suitable device), the server 140, the server 145, the server 150, and/or any other device. Additionally, the communications network 135 may be configured to transmit, generate, and receive any information and data traversing the system 100. In certain embodiments, the communications network 135 may include any number of servers, databases, or other componentry. The communications network 135 may also include and be connected to a mesh network, a local network, a cloud-computing network, an IMS network, a VoIP network, a security network, a VoLTE network, a wireless network, an Ethernet network, a satellite network, a broadband network, a cellular network, a private network, a cable network, the Internet, an internet protocol network, MPLS network, a content distribution network, any network, or any combination thereof. Illustratively, servers 140, 145, and 150 are shown as being included within communications network 135. In certain embodiments, the communications network 135 may be part of a single autonomous system that is located in a particular geographic region, or be part of multiple autonomous systems that span several geographic regions.

Notably, the functionality of the system 100 may be supported and executed by using any combination of the servers 140, 145, 150, and 160. The servers 140, 145, and 150 may reside in communications network 135, however, in certain embodiments, the servers 140, 145, 150 may reside outside communications network 135. The servers 140, 145, and 150 may provide and serve as a server service that performs the various operations and functions provided by the system 100. In certain embodiments, the server 140 may include a memory 141 that includes instructions, and a processor 142 that executes the instructions from the memory 141 to perform various operations that are performed by the server 140. The processor 142 may be hardware, software, or a combination thereof. Similarly, the server 145 may include a memory 146 that includes instructions, and a processor 147 that executes the instructions from the memory 146 to perform the various operations that are performed by the server 145. Furthermore, the server 150 may include a memory 151 that includes instructions, and a processor 152 that executes the instructions from the memory 151 to perform the various operations that are performed by the server 150. In certain embodiments, the servers 140, 145, 150, and 160 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 140, 145, 150 may be communicatively linked to the communications network 135, any network, any device in the system 100, or any combination thereof.

The database 155 of the system 100 may be utilized to store and relay information that traverses the system 100, cache content that traverses the system 100, store data about each of the devices in the system 100 and perform any other typical functions of a database. In certain embodiments, the database 155 may be connected to or reside within the communications network 135, any other network, or a combination thereof. In certain embodiments, the database 155 may serve as a central repository for any information associated with any of the devices and information associated with the system 100. Furthermore, the database 155 may include a processor and memory or be connected to a processor and memory to perform the various operation associated with the database 155. In certain embodiments, the database 155 may be connected to the servers 140, 145, 150, 160, the first user device 102, the second user device 111, the additional user devices, any devices in the system 100, any process of the system 100, any program of the system 100, any other device, any network, or any combination thereof.

The database 155 may also store information and metadata obtained from the system 100, store metadata and other information associated with the first and second users 101, 110, store surgical plans generated by the system 100, store landmark points set by users of the system 100 and/or suggested by the system 100, store image sets (and/or media content) taken of anatomy of users, store versions of the image sets (and/or media content) that have been enhanced via volume rendering, store information associated surgical registration processes conducted in the system 100, store implant positioning information, store surgical procedure information, store user profiles associated with the first and second users 101, 110, store device profiles associated with any device in the system 100, store communications traversing the system 100, store user preferences, store information associated with any device or signal in the system 100, store information relating to patterns of usage relating to the user devices 102, 111, store any information obtained from any of the networks in the system 100, store historical data associated with the first and second users 101, 110, store device characteristics, store information relating to any devices associated with the first and second users 101, 110, store information associated with the communications network 135, store any information generated and/or processed by the system 100, store any of the information disclosed for any of the operations and functions disclosed for the system 100 herewith, store any information traversing the system 100, or any combination thereof. Furthermore, the database 155 may be configured to process queries sent to it by any device in the system 100.

Figure 2:
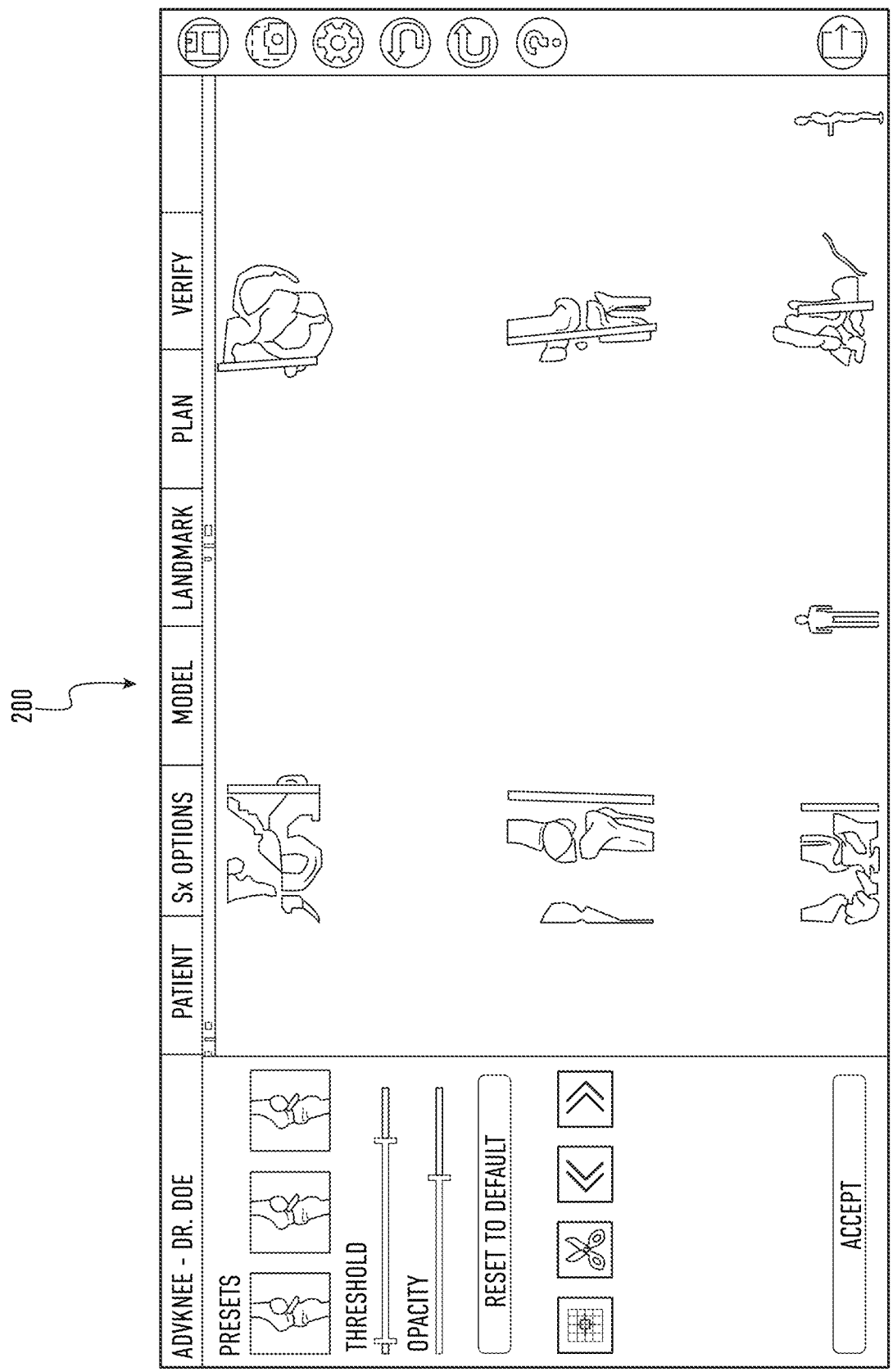
FIG. 2 is a sample user-interface of an application for use with the system of FIG. 1, which enables viewing of an enhanced image set.
Figure 3:
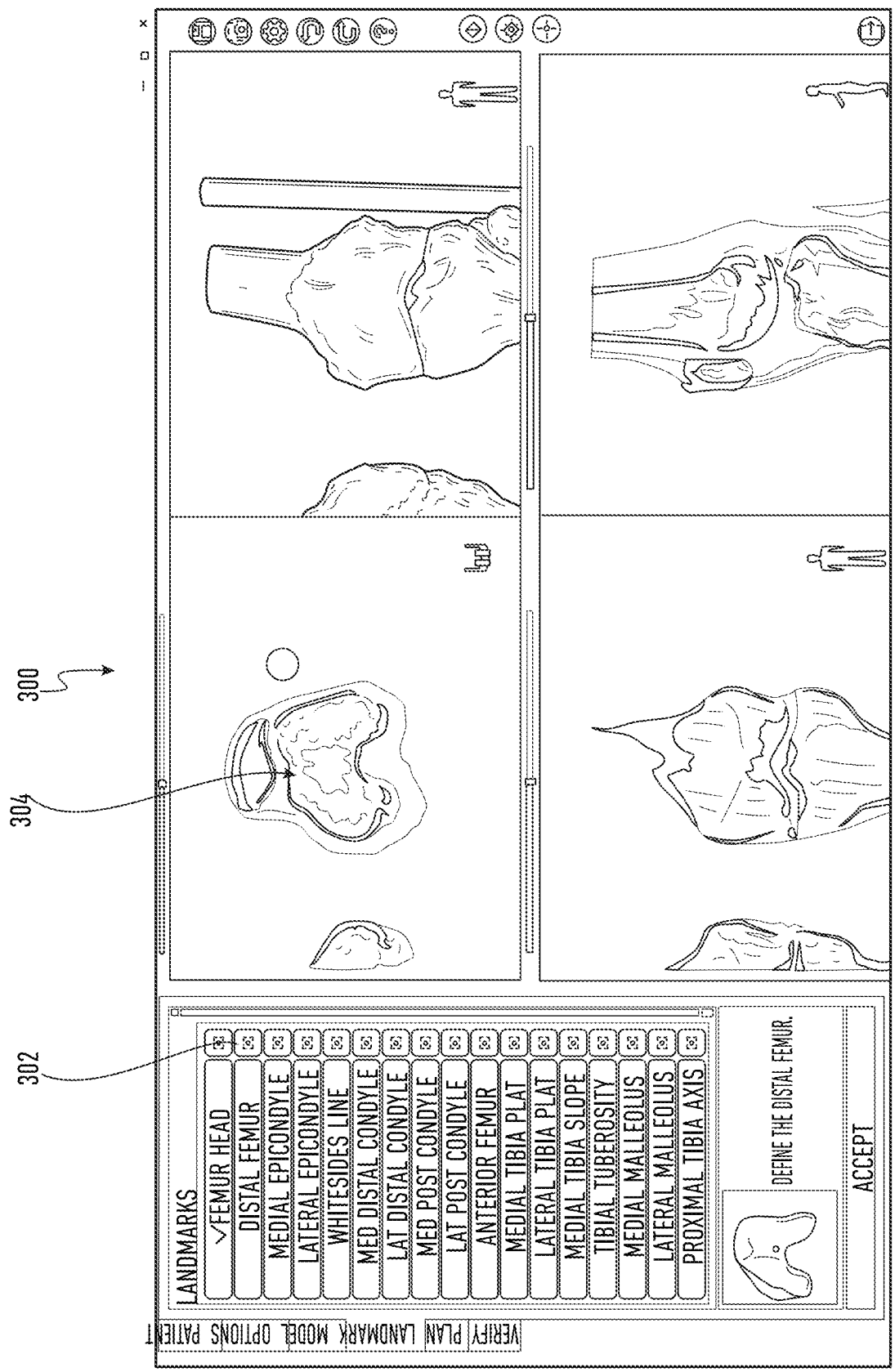
FIG. 3 is a sample user-interface of an application for use with the system of FIG. 1, which facilitates the selection of landmark points on an anatomy of a subject.
Figure 4:
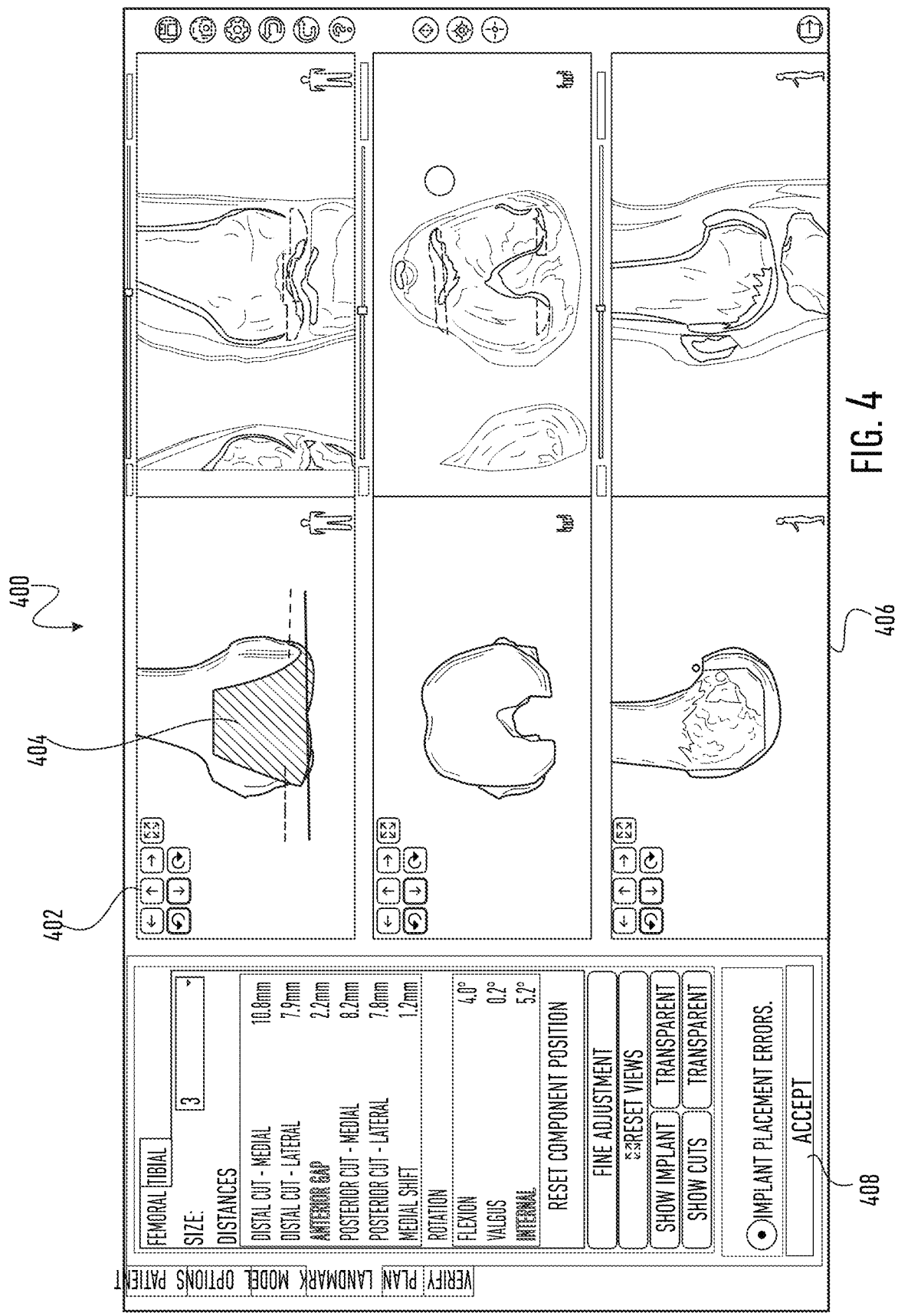
FIG. 4 is a sample user-interface of an application for use with the system of FIG. 1, which facilitates implant positioning with real-time visual feedback.

Operatively, the system 100 may operate and/or execute the functionality as described in the methods (e.g. method 3000 as described below) of the present disclosure and in the following description. Referring specifically to FIGS. 2-4, a surgeon or a physician may utilize an imaging device to take an image(s), image set, and/or media content of an anatomy of interest of a subject, such as a subject's knee, for the purposes of gathering information prior to performing a knee arthroplasty on the subject. The images and/or media content taken of the anatomy of the subject may, in certain embodiments, be processed using automatic 3D image filters to reduce noise and eliminate portions of anatomy that are not required for implant planning and/or registration. In certain embodiments, portions of the anatomy may be manually removed from the images and/or media content, such as by utilizing a manual tool provided by software. For example, the digital scissor tool shown in interface screen 200 may be utilized by a user of the system 100 to manually eliminate (or potentially modify) portions of the anatomy of a subject. In certain embodiments, a combination of manual and automatic elimination (or potentially modification) of portions of an anatomy may be conducted as desired as well. Interface screen 200 illustrates modeling that may be conducted by the system 100, such as for use with the implant plan. The system 100 may then render the 3D images on the user interface, such as on the user interface of second user device 111, without generating surface models or using bone contouring. As shown in FIG. 3, the system 100 may suggest anatomical landmark points in the rendered volume of the distal femur 302, for example, as shown in interface screen 300. The surgeon may refine the suggested anatomical landmark points 304 before accepting the landmark points, such as via inputs into the software program.

Once the anatomical landmarks are defined using the software program, the system 100 may then enable the surgeon to proceed with implant positioning for the plan with real-time visual feedback via the interface of the software program. The surgeon may conduct the implant positioning by utilizing implant controls rendered in the user interface of the software program. For example, the implant controls may be utilized to the adjust the orientation, location, distance, angles, and/or other metrics associated with positioning the implant. The implant positioning may also allow for rotating the implant and/or moving the implant back and forth along selected planes. In certain embodiments, the implant position controls may be rendered in the same views where the volume rendering of the bones is made visible. For example, as shown in interface screen 400, implant controls 402 are rendered in proximity to the volume rendered image 404 of the knee of the subject. As the surgeon adjusts the pose of the implant, the respective bone cuts may be updated and visualized by the system 100 via the interface. In certain embodiments, measurements related to the implant pose may be calculated by the program each time the implant positions are adjusted, and the measurements may be displayed blended with the volume rendering to assist the surgeon to select the optimal implant positions, as shown via reference 406. Once the desired implant positions are achieved and/or selected, the surgeon can save the positions relative to the anatomical landmarks via an "Accept" input button 408 of the user interface. The plan may be finalized and the registration process may be conducted to match the subject's anatomy with the information contained in images in the plan. Then, the surgeon may perform the implant surgery for the subject by using the plan.

Figure 5:
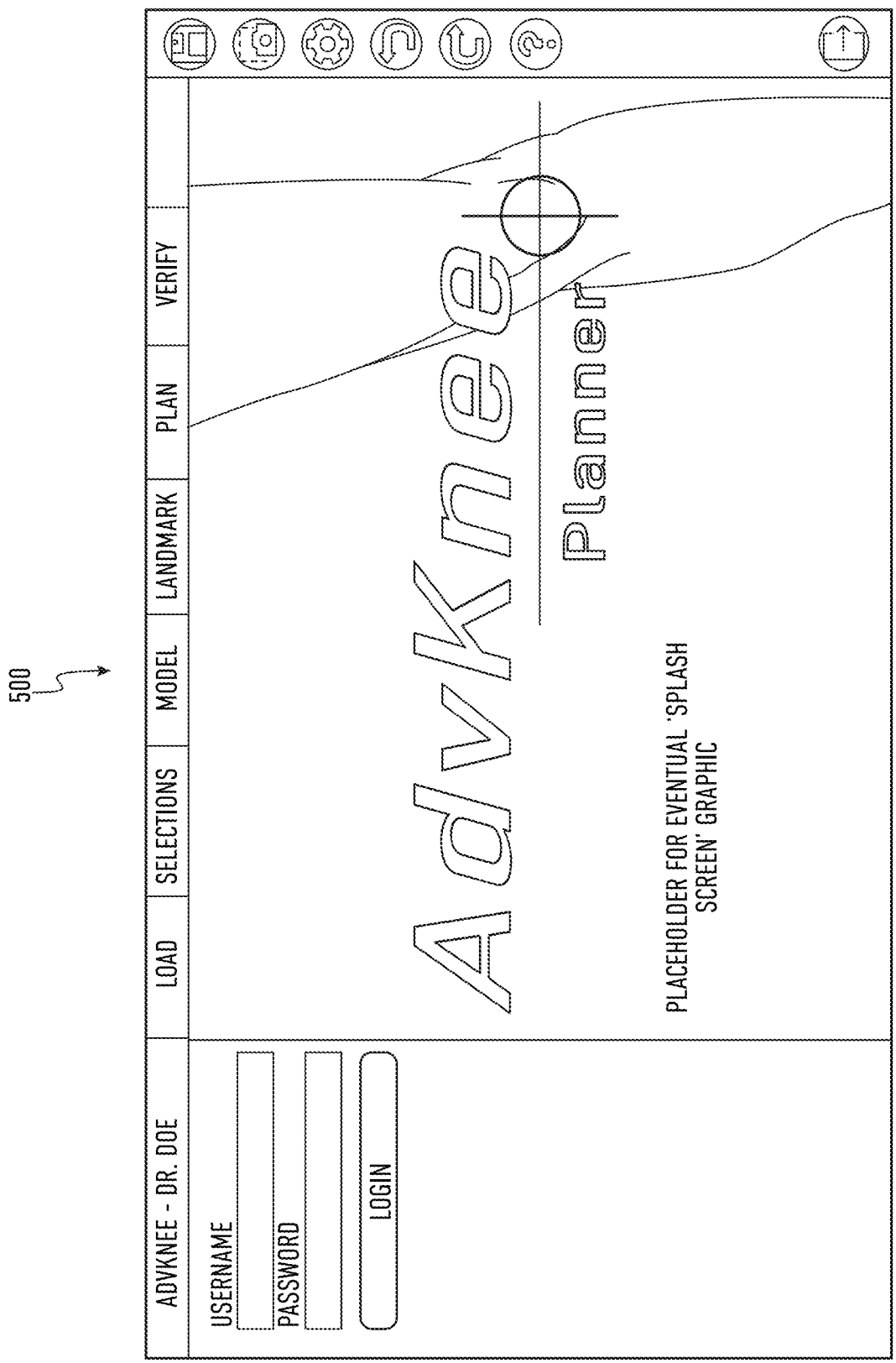
FIG. 5 is a sample user-interface of an application for use with the system of FIG. 1, which enables a user to authenticate into and access the features of the system of FIG. 1.
Figure 6:
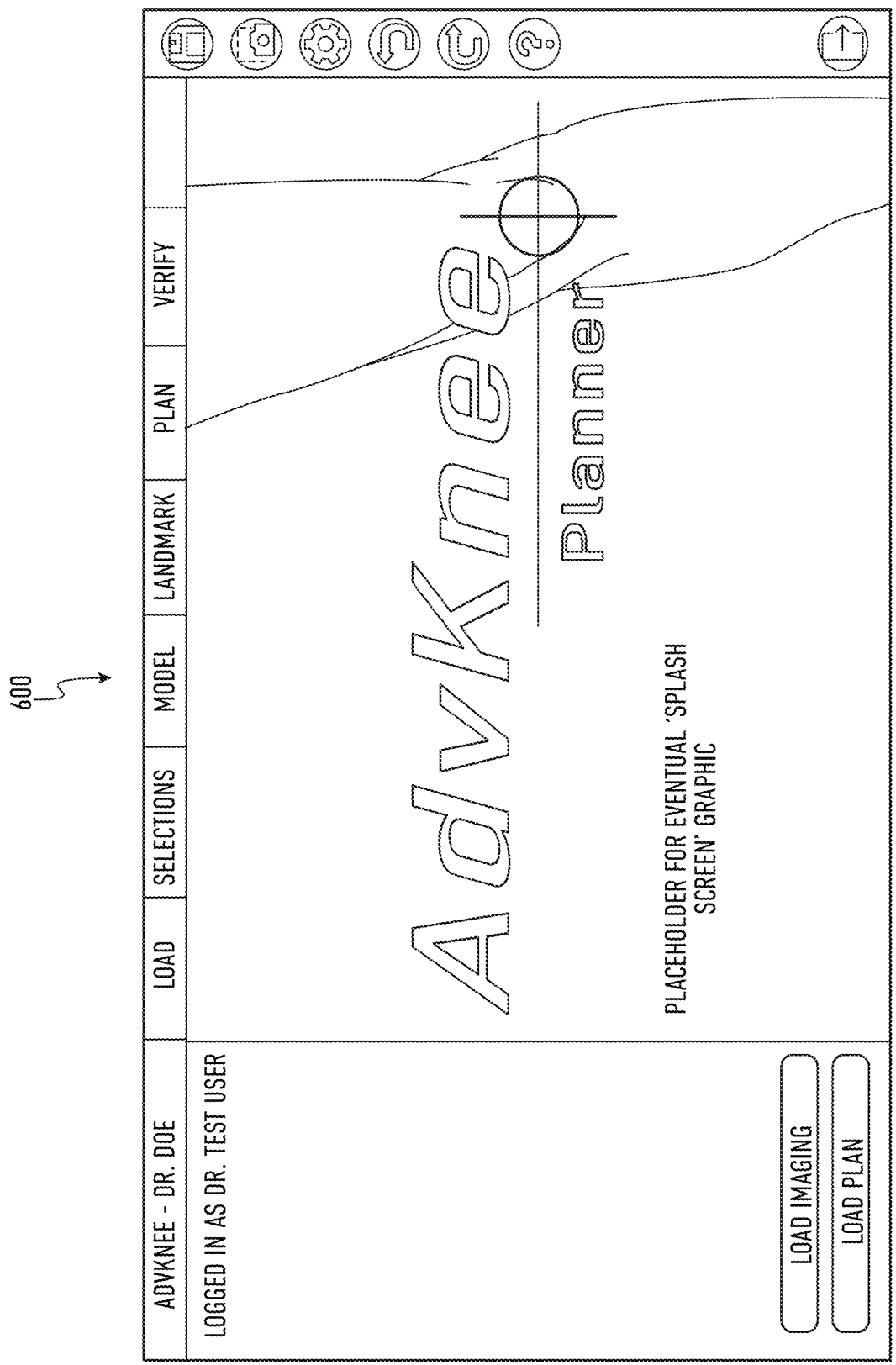
FIG. 6 is a sample user-interface of an application for use with the system of FIG. 1, which facilitates loading of an image to start a new plan for a subject or load an existing plan for the subject.

Referring now also to FIGS. 5-29, a process flow for using the program/application providing the operative functionality of the system 100 is shown. For example, the process flow may be utilized to generate a plan for a surgical procedure for implanting an implant onto an anatomy of interest of a subject. In FIG. 5, an interface screen 500 is shown, which enables the surgeon (or other authorized user) to authenticate into program providing the functionality of the system 100. The program may enable the surgeon to have access to images of anatomy that have been imported into the program, and to plans that have been generated using the program. In certain embodiments, the surgeon may also have the option to share images of the anatomy and plans with other authorized users of the system 100. In FIG. 6, an interface screen 600 is shown, which enables the surgeon to load an image to start a new surgical plan. The interface screen 600 of the program also enables the surgeon to load and/or browse plans that have been previously generated and/or edited. In FIG. 7, an interface screen 700 is shown, which is displayed when the surgeon selects the option to load an image into the program from user interface screen 600. The interface screen 700 displays a browser, which enables the surgeon to import and/or select the image(s) and/or media content associated with the anatomy of the subject, such as images taken by a CT machine, MRI machine, and the like. In certain embodiments, the interface screen 700 may include a preview panel, which allows for the browsing of axial image slices to check the scan quality of the images taken of the anatomy of the subject.

Figure 8:
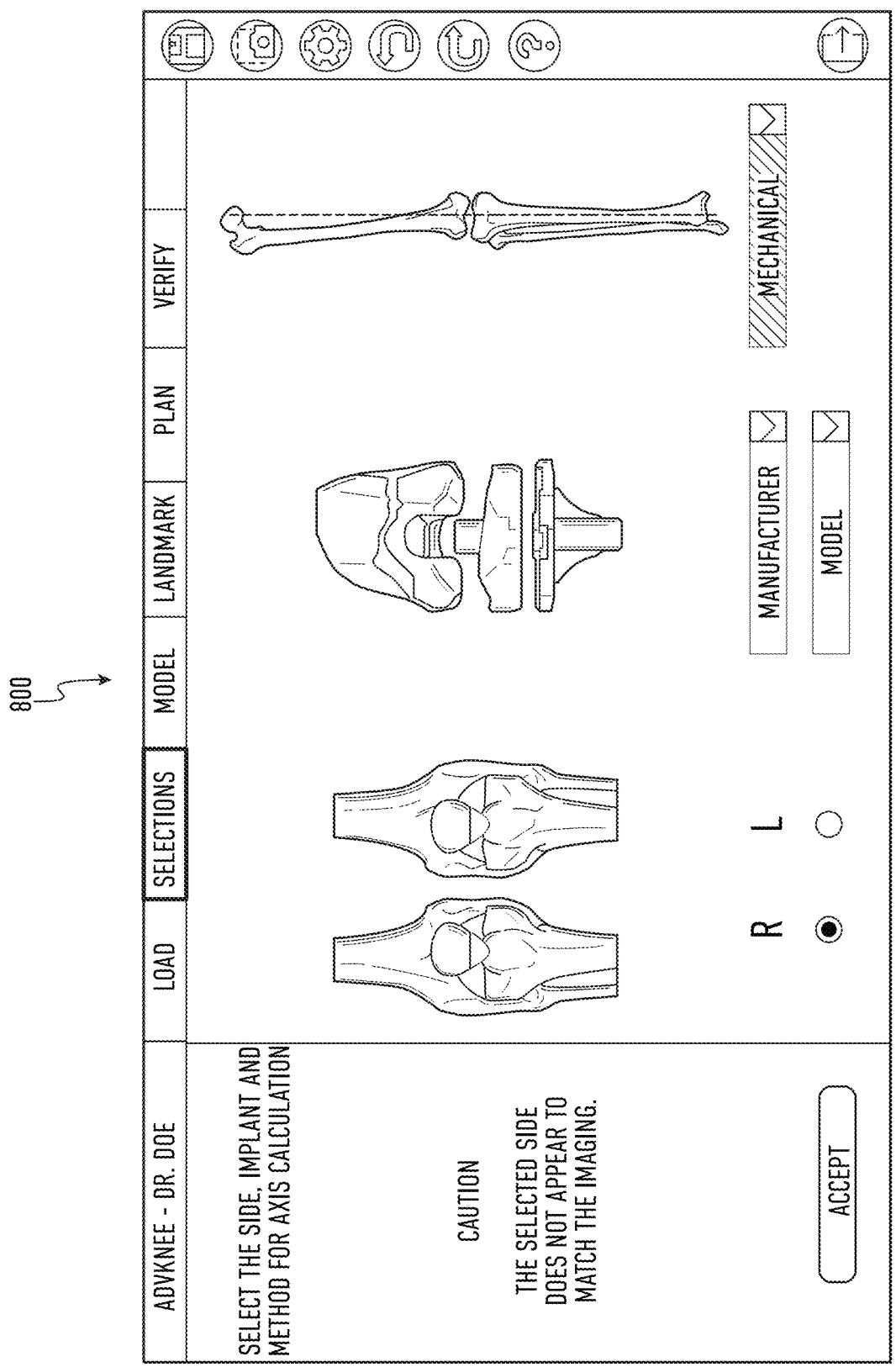
FIG. 8 is a sample user-interface of an application for use with the system of FIG. 1, which facilitates the selection of the type of implant to be utilized for a surgical procedure, which side of the anatomy that the surgical procedure will be performed on, and the surgical method to be utilized for surgical procedure.
Figure 9:
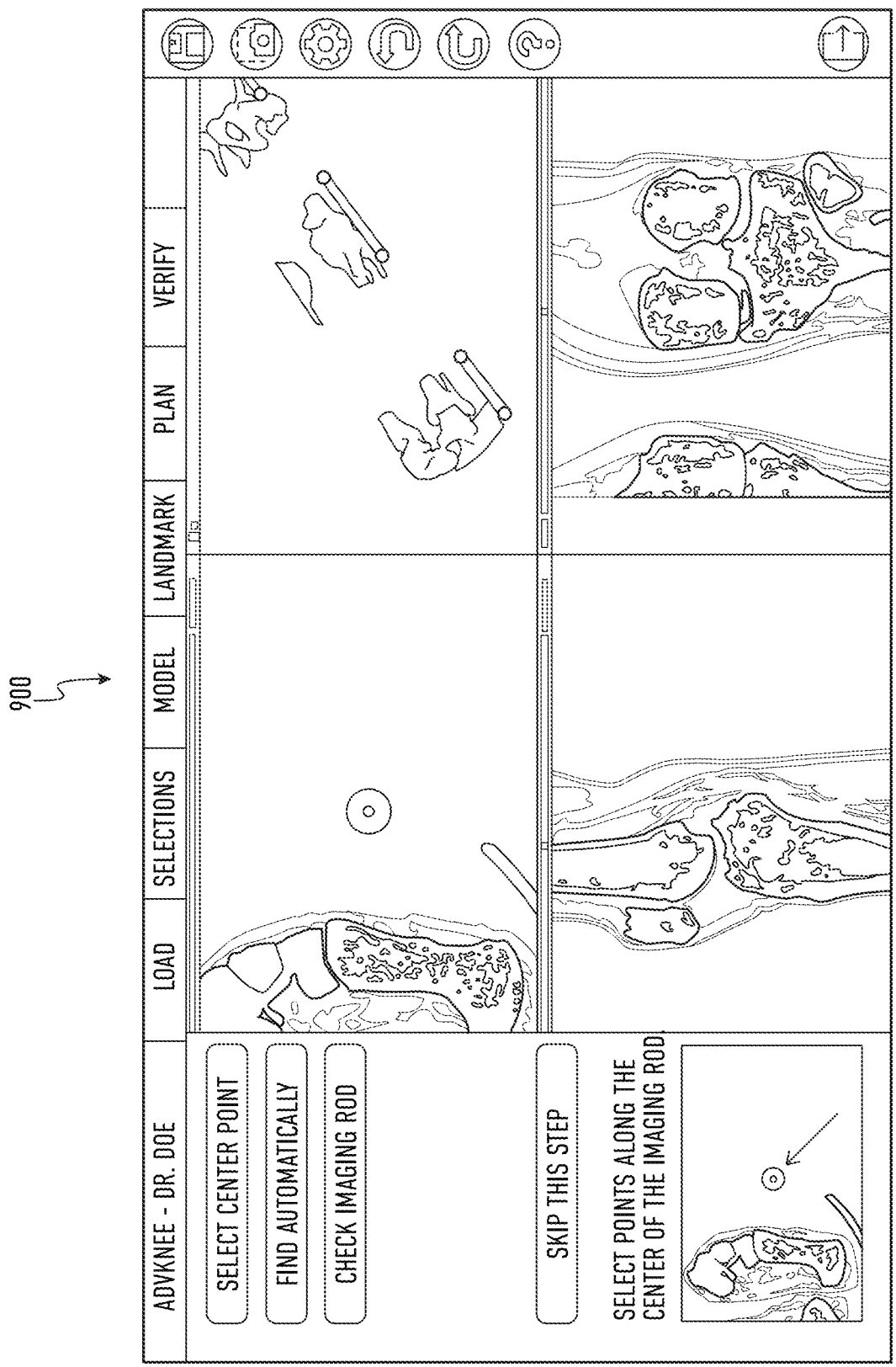
FIG. 9 is a sample user-interface of an application for use with the system of FIG. 1, which facilitates selection of imaging rod points if an imaging rod is utilized with the system of FIG. 1.
Figure 10:
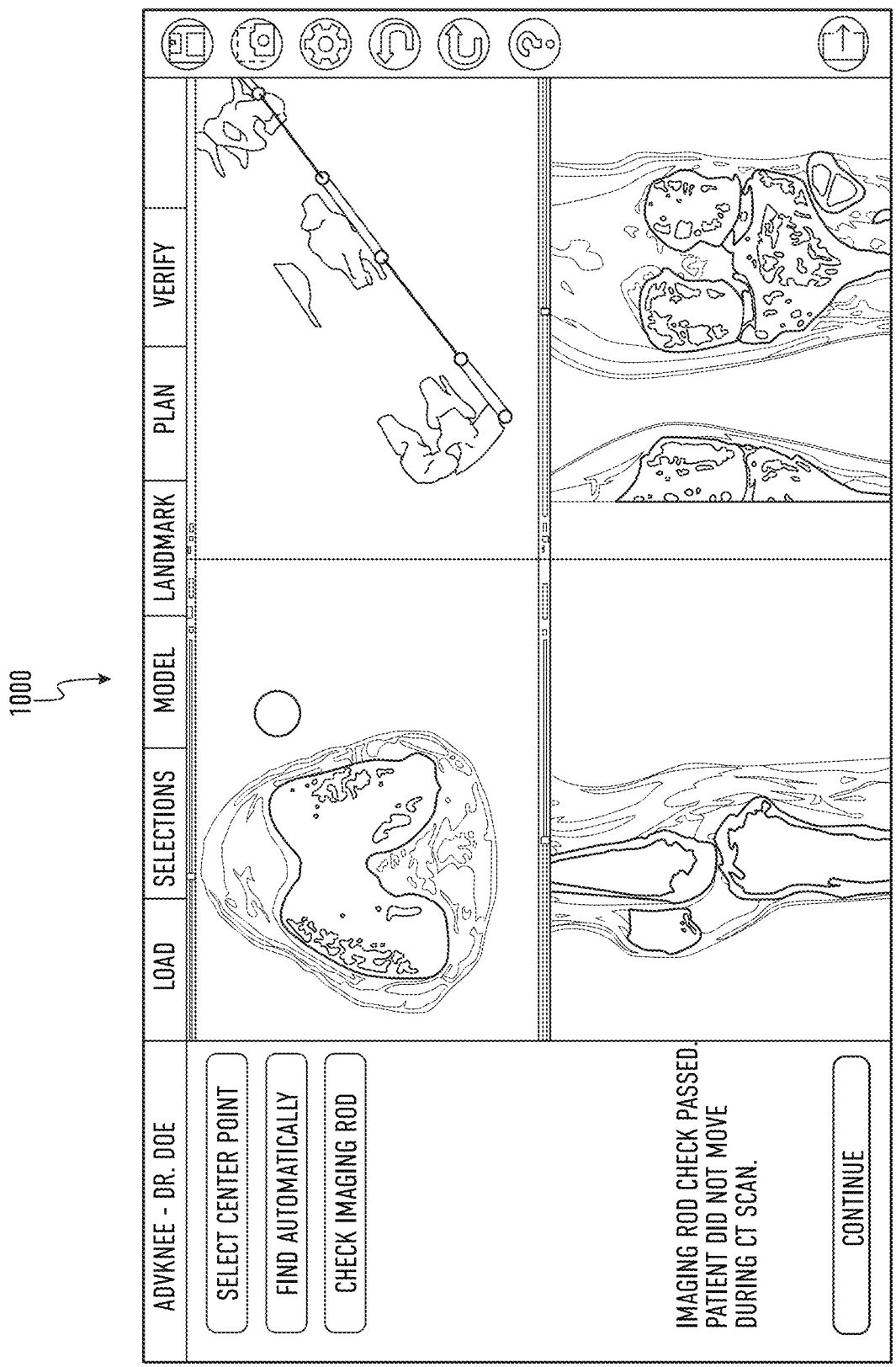
FIG. 10 is a sample user-interface of an application for use with the system of FIG. 1, which facilitates the visualization of an imaging rod after selection of imaging rod points.

Once the surgeon has loaded the image(s) and/or media content of the anatomy of interest into the program, the user interface screen 800 of FIG. 8 of the program may be displayed. The user interface screen 800 may enable the user to select which side the subject and/or anatomy that the surgical procedure will be performed on, the implant type (e.g. manufacturer, model, etc.), and the desired surgical method. In certain embodiments, if the selected side mismatches the side entered by the technician who conducted the imaging of the anatomy, the program may display a warning, as shown in FIG. 8. In certain embodiments, as an option step, the program may be utilized to check imaging rod alignment, as shown interface screen 900 in FIG. 9. In certain embodiments, this step may be bypassed if no imaging rod is utilized. However, if an imaging rod is utilized, imaging rod points may be selected automatically or manually before the check is conducted. In certain embodiments, automatic marking may be utilized if the subject does not have metal implants. After manual or automatic marking of points is conducted using the program, the imaging rod may be visualized, as shown in interface screen 1000 of FIG. 10. The imaging rod may be visualized in a 3D viewer and the surgeon may be warned if any segment deviates from the line, such as in the event that the subject moved during the imaging process.

Figure 11:
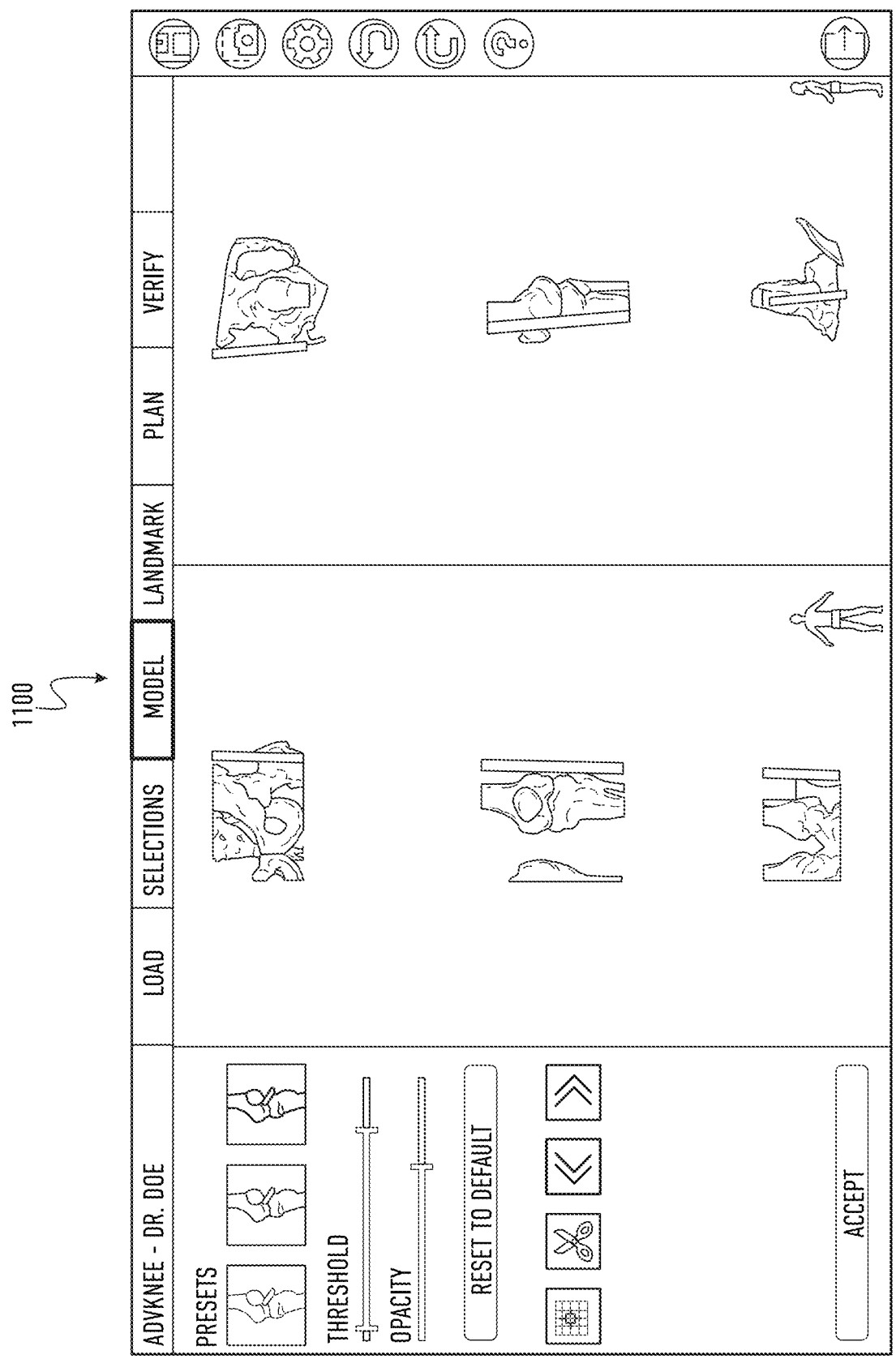
FIG. 11 is a sample user-interface of an application for use with the system of FIG. 1, which facilitates the setting up of volume rendering that may be used for generating a plan for the subject.
Figure 12:
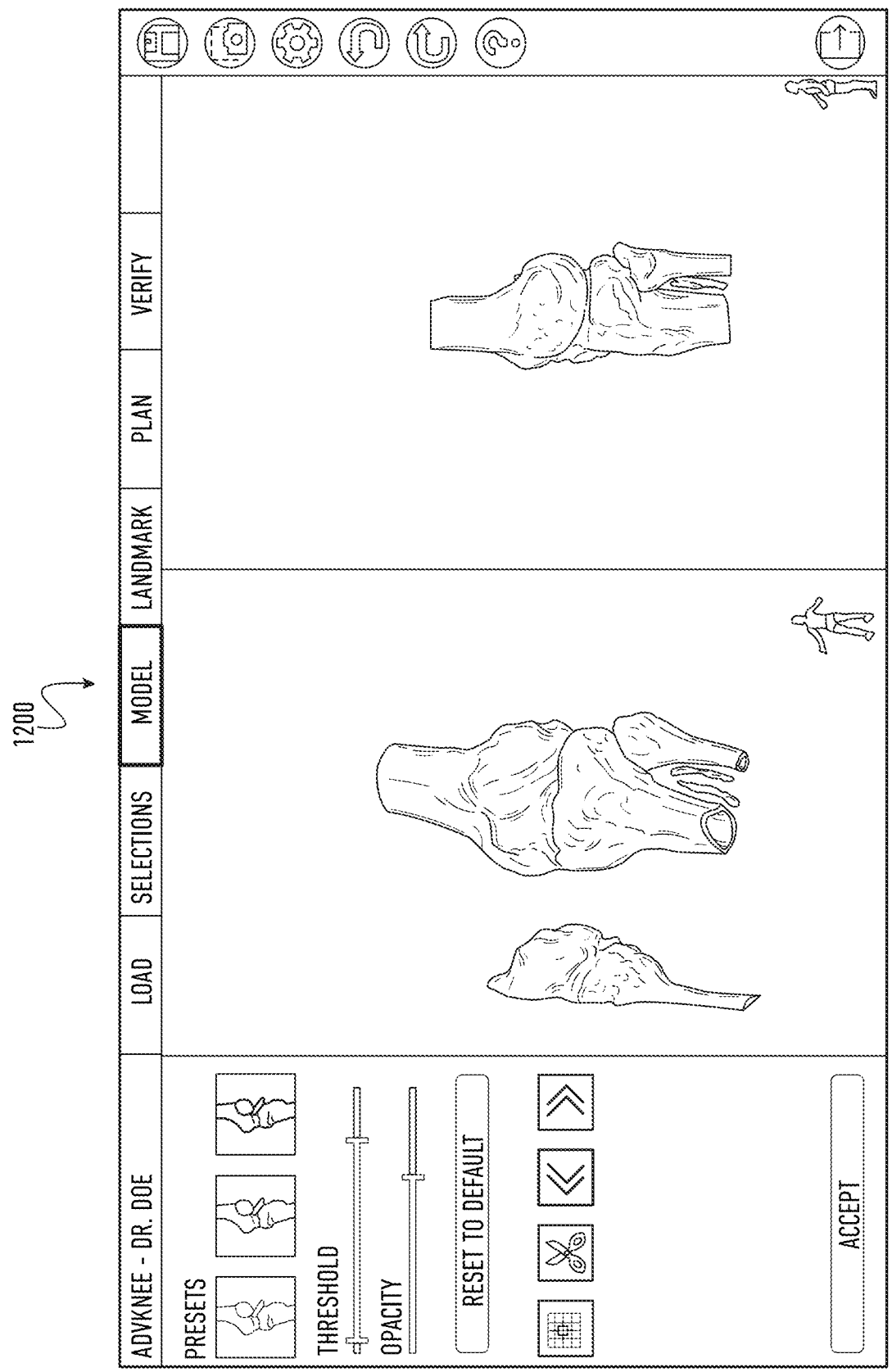
FIG. 12 is a sample user-interface of an application for use with the system of FIG. 1, which facilitates the digital editing of the rendered volume of the anatomy.
Figure 13:
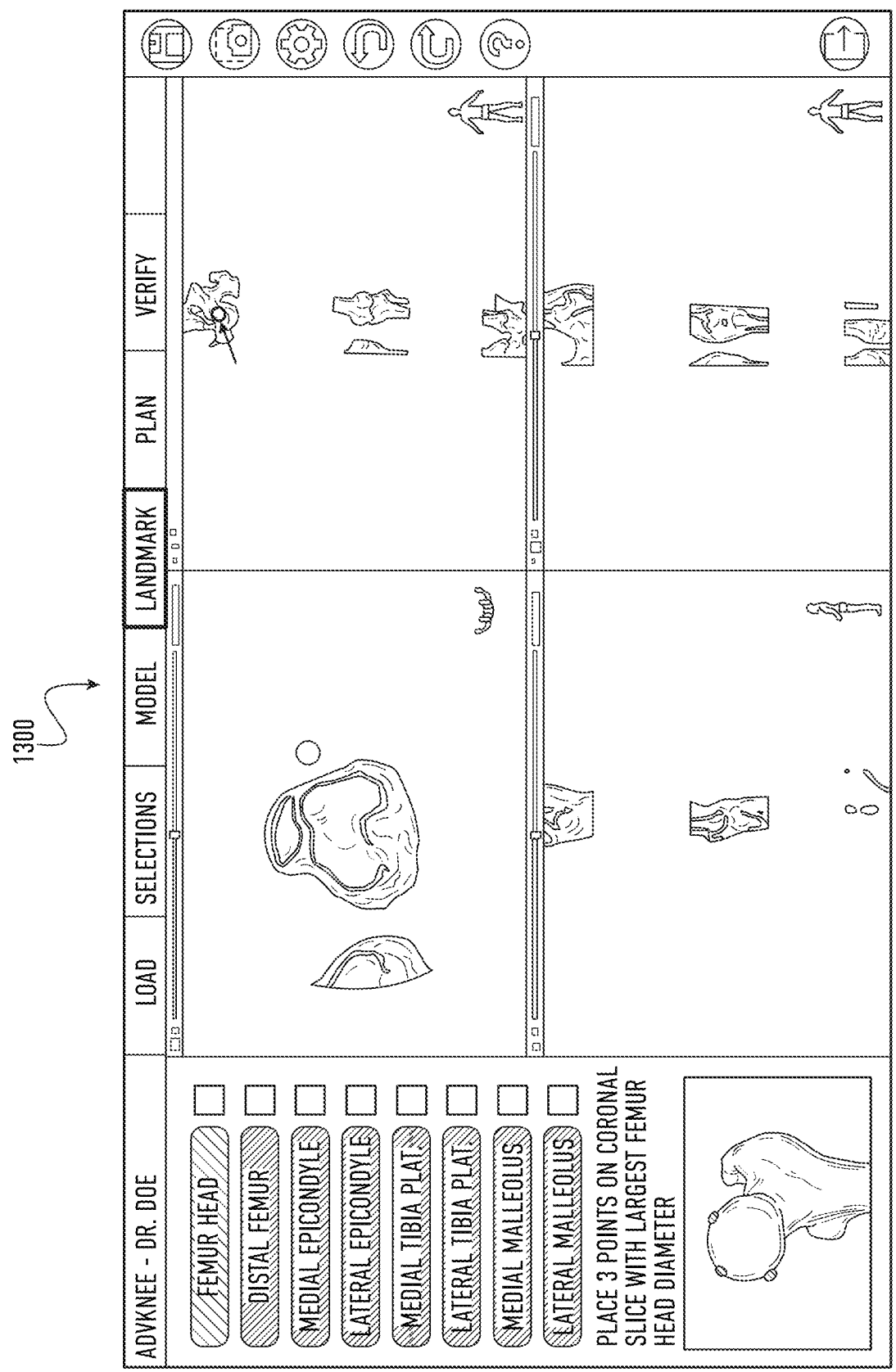
FIG. 13 is a sample user-interface of an application for use with the system of FIG. 1, which facilitates anatomical landmarking.

In FIG. 11, interface screen 1100 enables the surgeon to set up volume visualization for the image of the anatomy (and/or image set and/or media content). For example, the surgeon may adjust the opacity and corresponding threshold of the volume rendering that will be used for generating the plan for the subject. FIG. 12 displays a user interface screen 1200 of the program, which provides tools for editing the rendered volume of the anatomy of interest. For example, tools may include island removal and 3D scissor tools to remove objects from the image volume that are not needed for planning. For example, a patella, imaging rod, and/or contralateral leg may be removed from the rendered volume. FIG. 13 includes a user interface screen 1300, which allows for anatomical landmarking of the volume rendered images. For example, the anatomical landmarking may be performed in a 4-view window layout, which may include three 2D views showing axial, sagittal, and coronal cross-sections of the volume rendered images of the anatomy and a fourth view showing 3D volume rendering of the bones. In certain embodiments, a 3D cursor may be utilized to allow for fast navigation in all views. In certain embodiments, a button press in any of the views may align all other view centers to the anatomical location of the mouse pointer of the mouse (or other input device or finger of the user). Depending on the planning technique and/or implant manufacturer instructions, the list of anatomical landmarks may be updated. In certain embodiments, landmarks may be redefined by clicking on (or selecting) any of the items in the left panel list of the user interface screen 1300. In certain embodiments, optional landmarks may also be present as well. Such optional landmarks may be utilized to increase accuracy. In this case, the landmarking is for the femur head of the anatomy of a subject. The surgeon can utilize a 3D cursor to find the anatomical region shown in the guide picture, as shown in the bottom left of FIG. 13.

Figure 14:
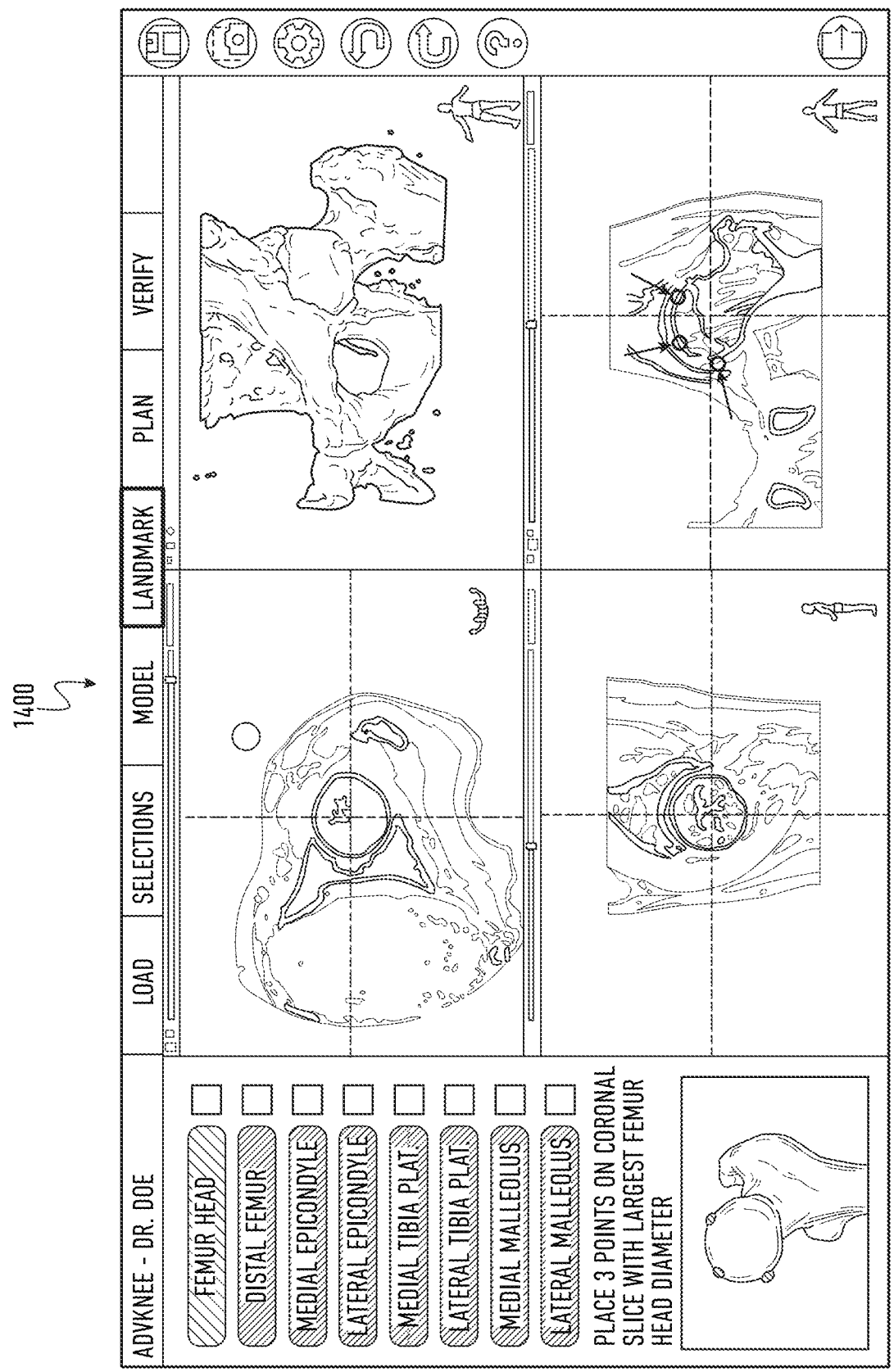
FIG. 14 is a sample user-interface of an application for use with the system of FIG. 1, which facilitates the defining of landmark points for a portion of the anatomy of a subject.
Figure 15:
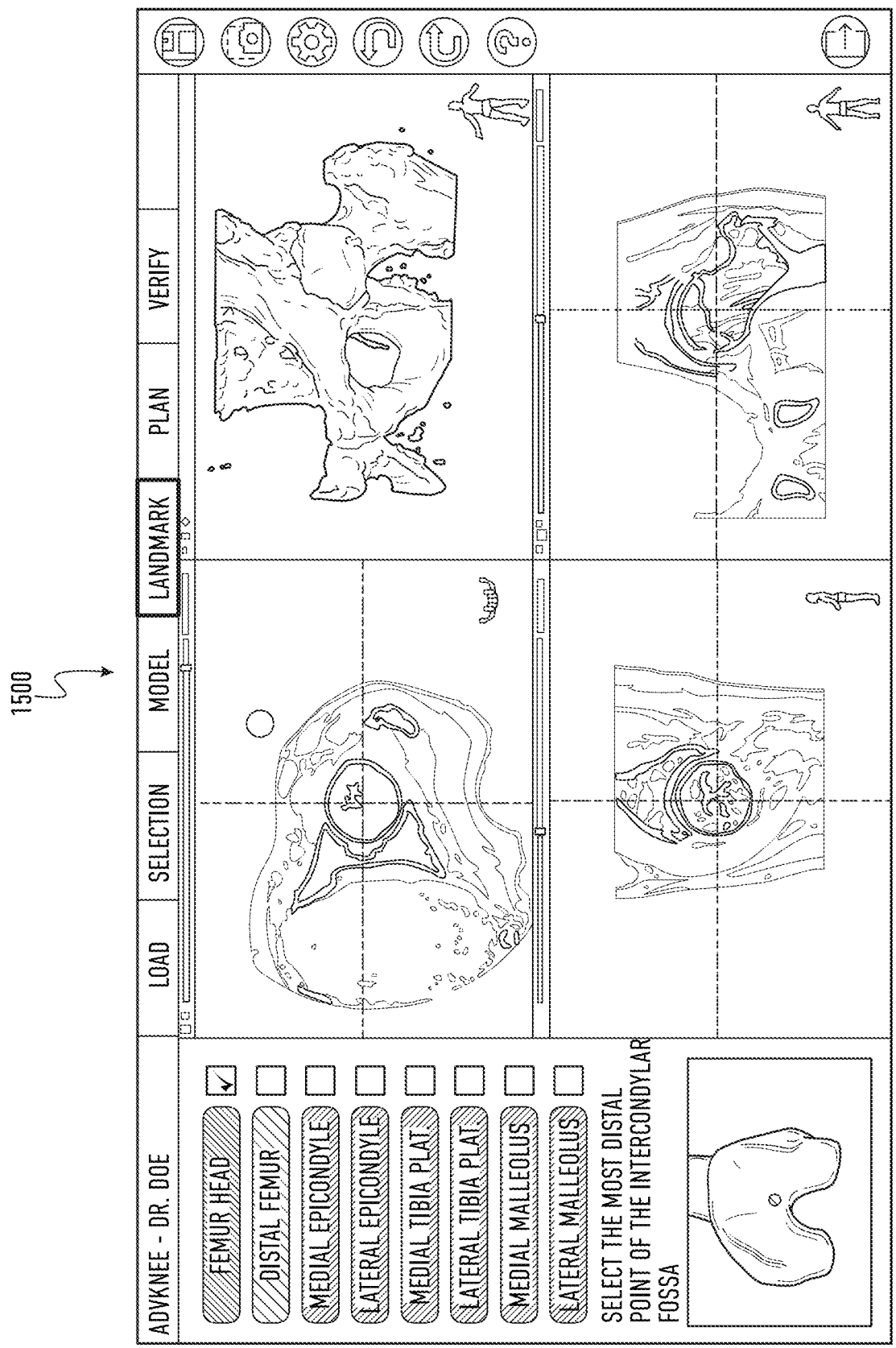
FIG. 15 is a sample user-interface of an application for use with the system of FIG. 1, which facilitates anatomical landmarking for another portion of the anatomy of the subject.
Figure 16:
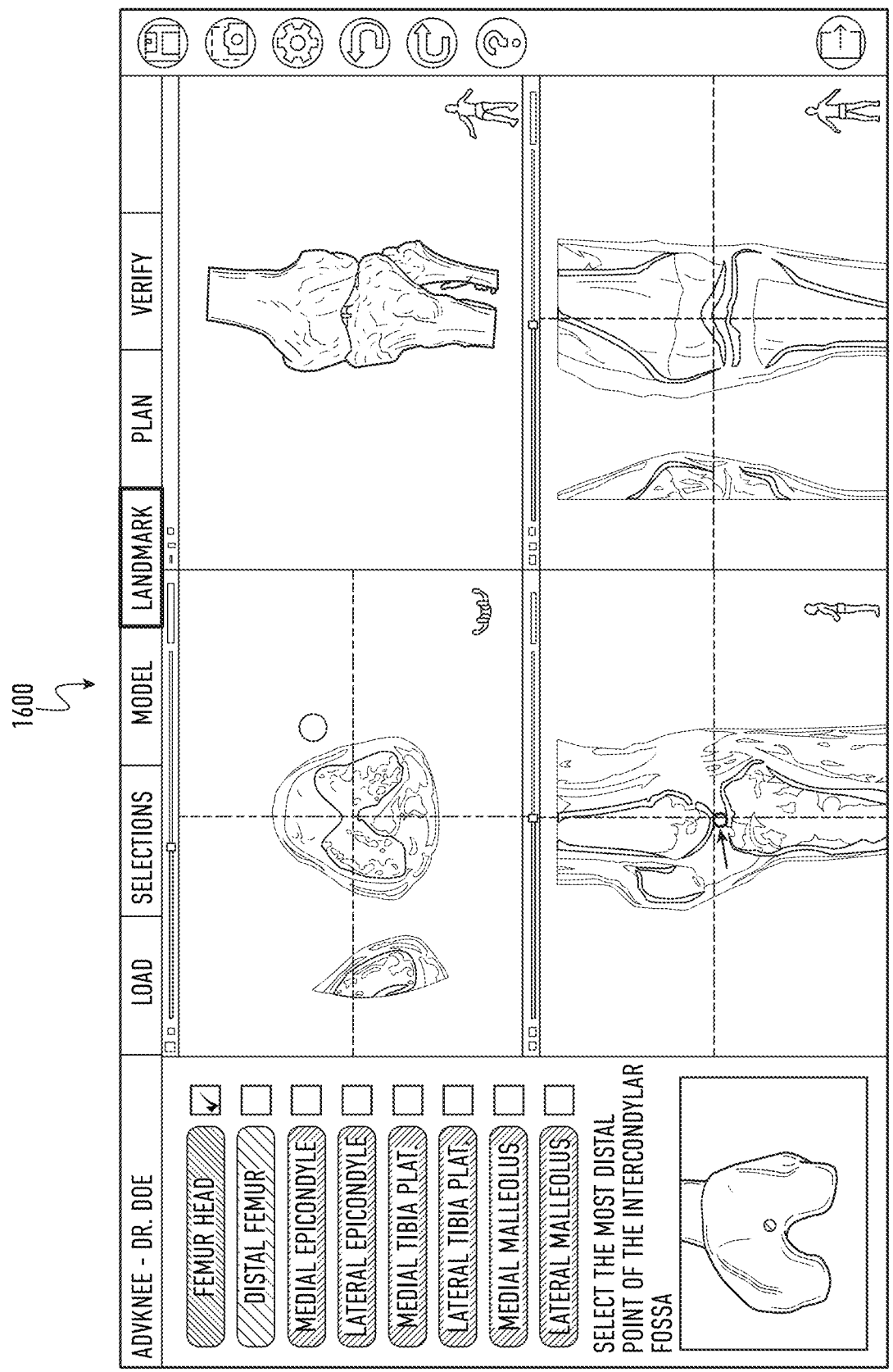
FIG. 16 is a sample user-interface of an application for use with the system of FIG. 1, which facilitates the placement of landmark points for a portion of the anatomy.
Figure 17:
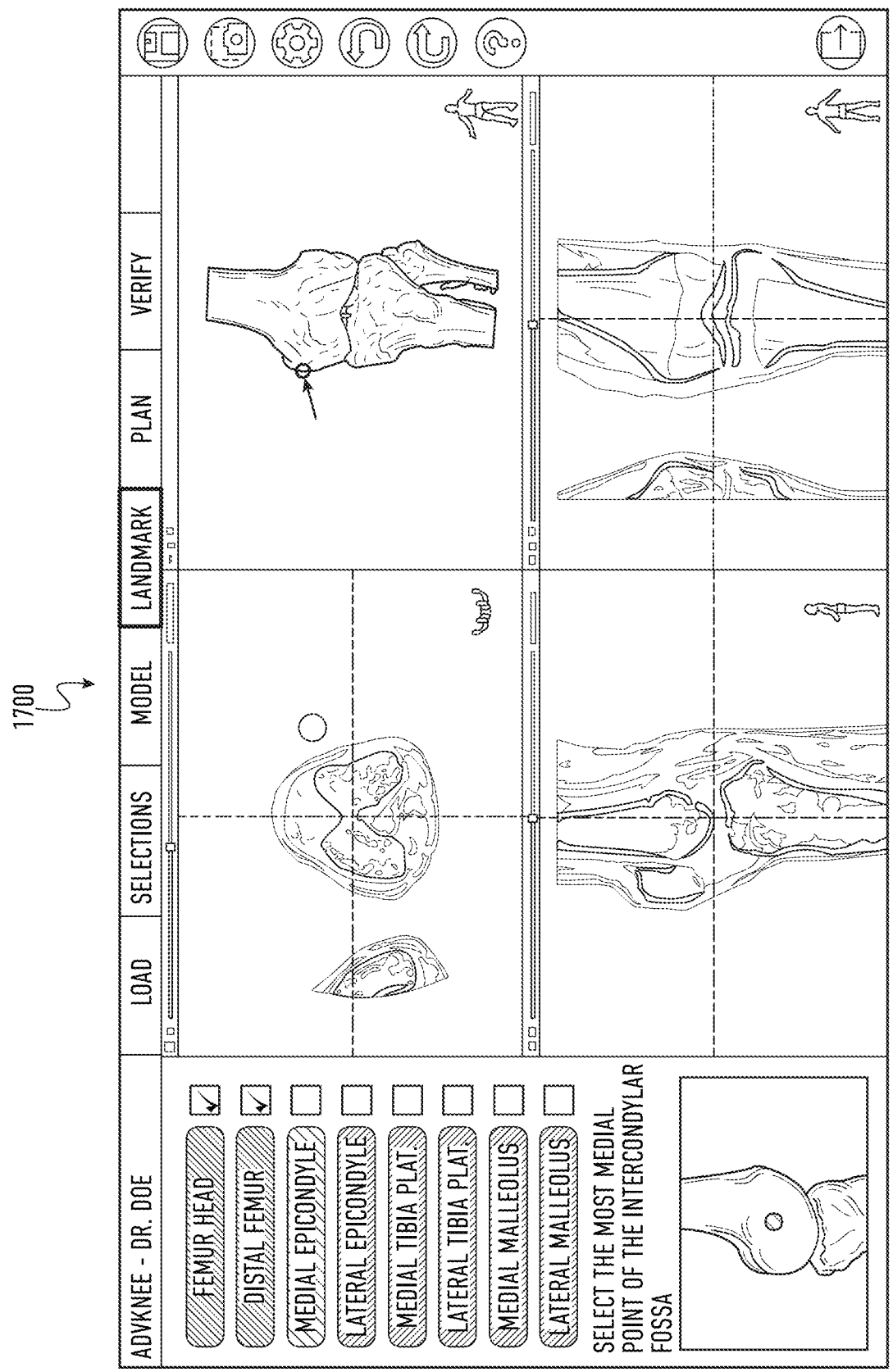
FIG. 17 is a sample user-interface of an application for use with the system of FIG. 1, which facilitates anatomical landmarking for another portion of the anatomy of the subject.
Figure 18:
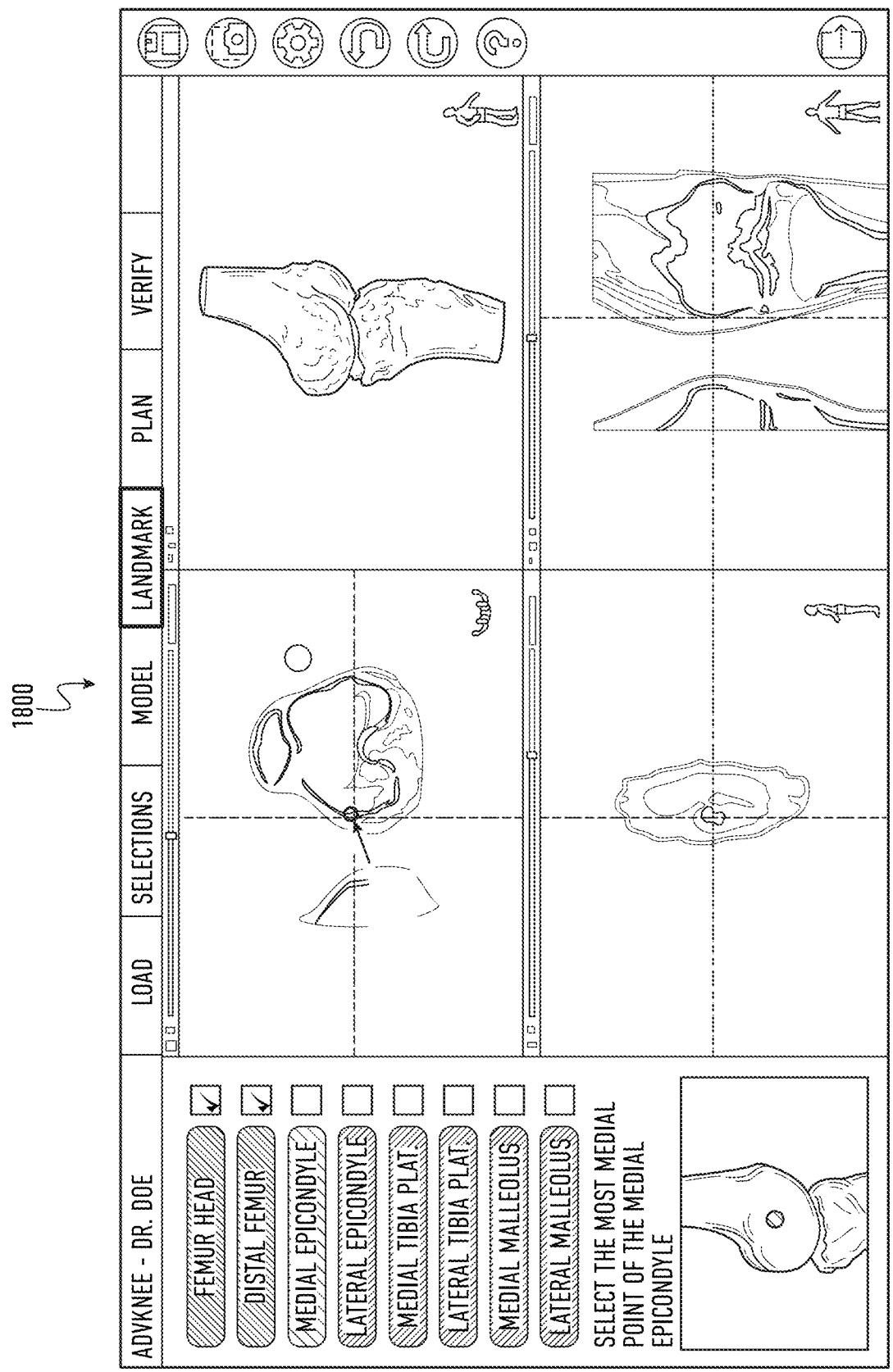
FIG. 18 is a sample user-interface of an application for use with the system of FIG. 1, which facilitates the placement of landmark points for a portion of the anatomy.

In FIG. 14, a user interface screen 1400 for landmarking the femur head is shown. The user interface screen 1400 of the program may enable the surgeon to define landmark points, as shown in FIG. 14. The femur head may be a special landmark, which may be defined as the center of the sphere fitted on three selected landmark points on the femur head. Once the femur head landmark is defined, the guide picture shown in the user interface may be updated to show the next landmark, which in this case may be the distal femur, as shown in interface screen 1500 of FIG. 15. The surgeon may utilize the 3D cursor to find the anatomical region shown the guide picture, such as by zooming out and clicking on the distal femur in any of the viewers shown on interface screen 1500. In FIG. 16, user interface screen 1600 shows how any of the views may be utilized to place a landmark in the most distal point of the intercondylar notch of the anatomy. The program may then allow the surgeon to proceed to the next landmark, as shown in user interface screen 1700 of FIG. 17. In this case, the next landmark may be the medial epicondyle landmark, and the surgeon may utilize a 3D cursor to find the anatomical region shown in the guide picture, such as by zooming out and clicking on the distal femur in any of the viewers shown. User interface screen 1800 of FIG. 18 shows how the surgeon may utilize any of the displayed views to place a landmark point at the medial epicondyle.

Figure 19:
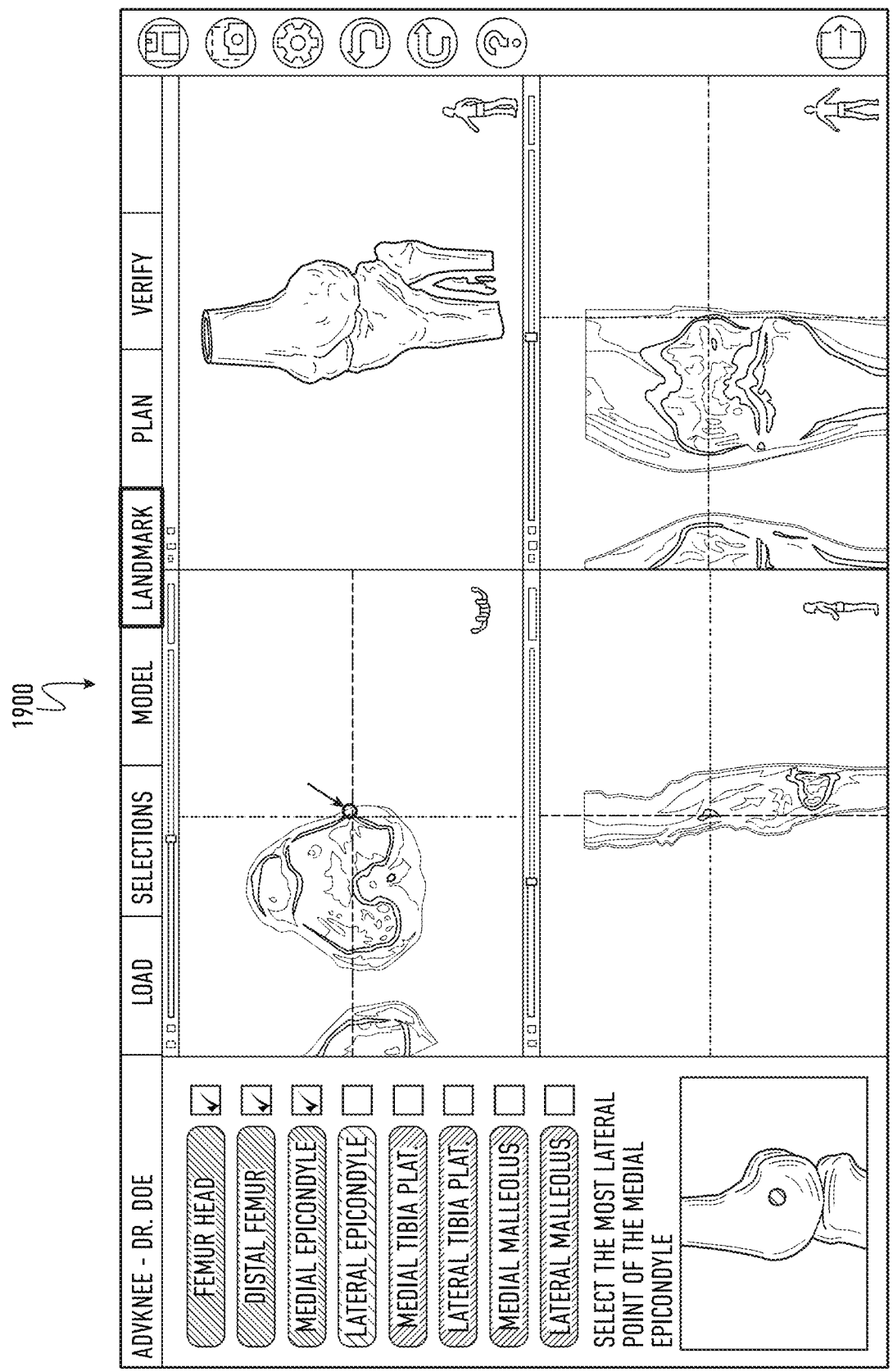
FIG. 19 is a sample user-interface of an application for use with the system of FIG. 1, which facilitates anatomical landmarking for another portion of the anatomy of the subject.
Figure 20:
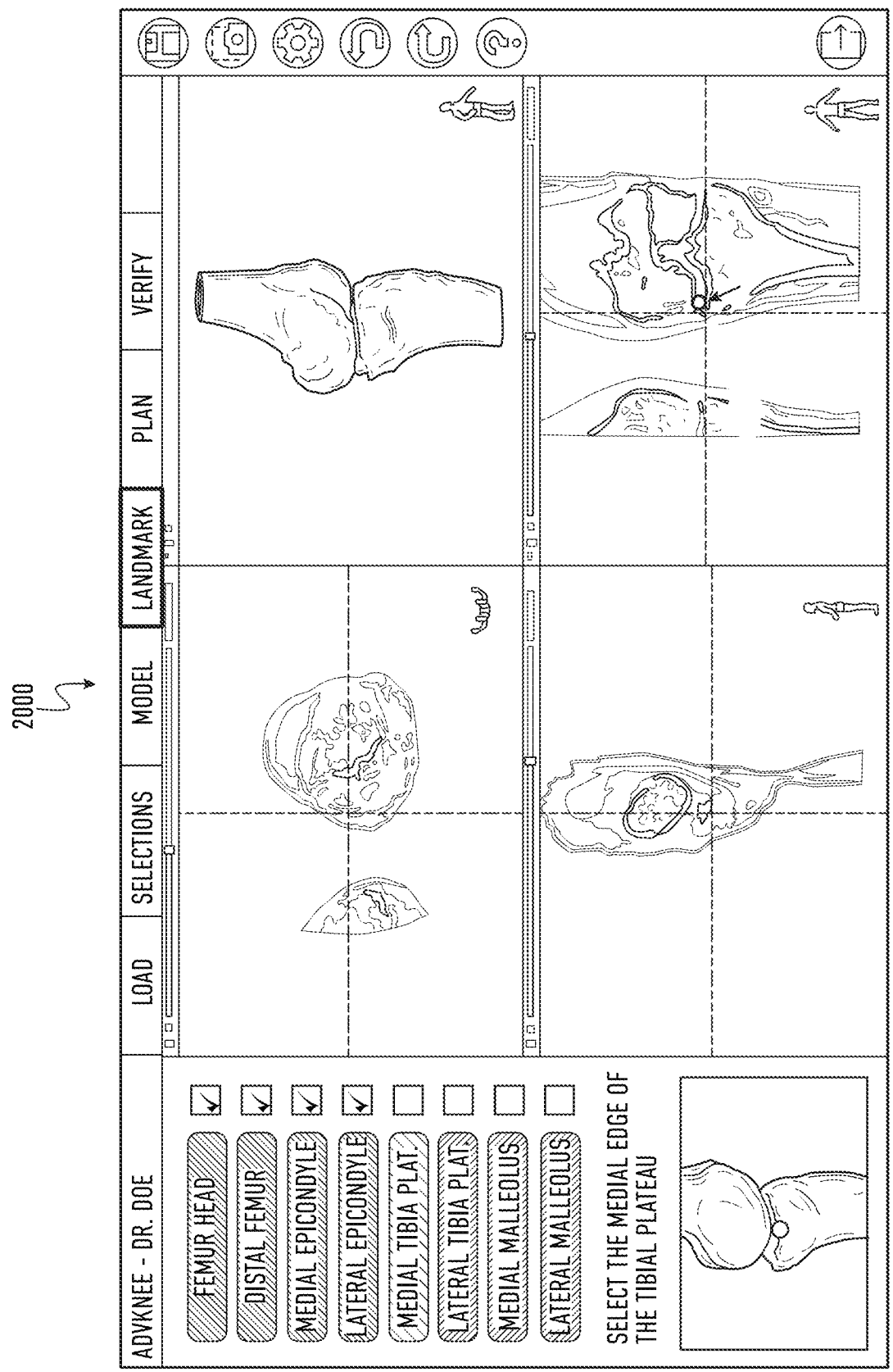
FIG. 20 is a sample user-interface of an application for use with the system of FIG. 1, which facilitates anatomical landmarking for another portion of the anatomy of the subject.
Figure 21:
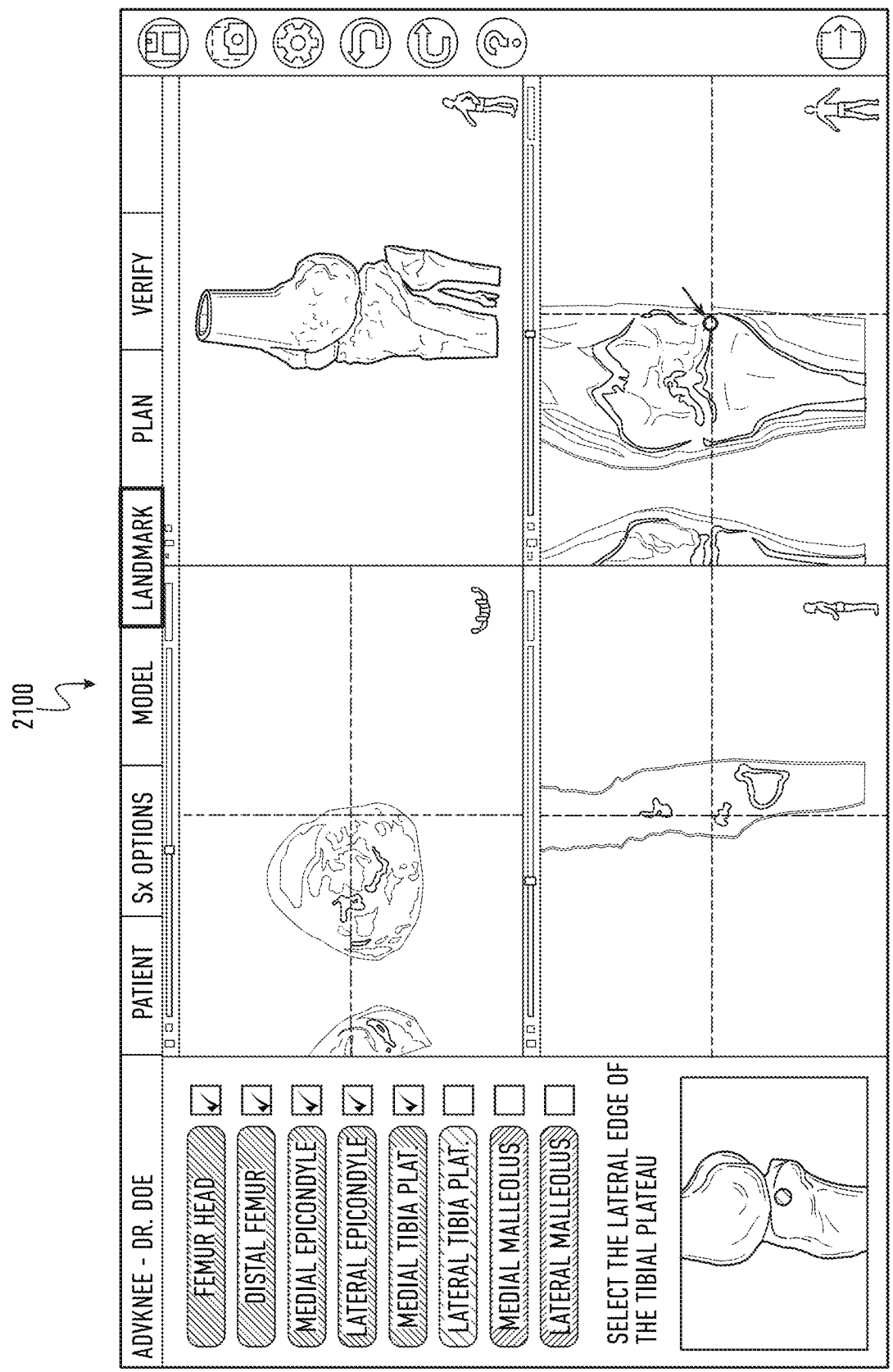
FIG. 21 is a sample user-interface of an application for use with the system of FIG. 1, which facilitates anatomical landmarking for another portion of the anatomy of the subject.
Figure 22:
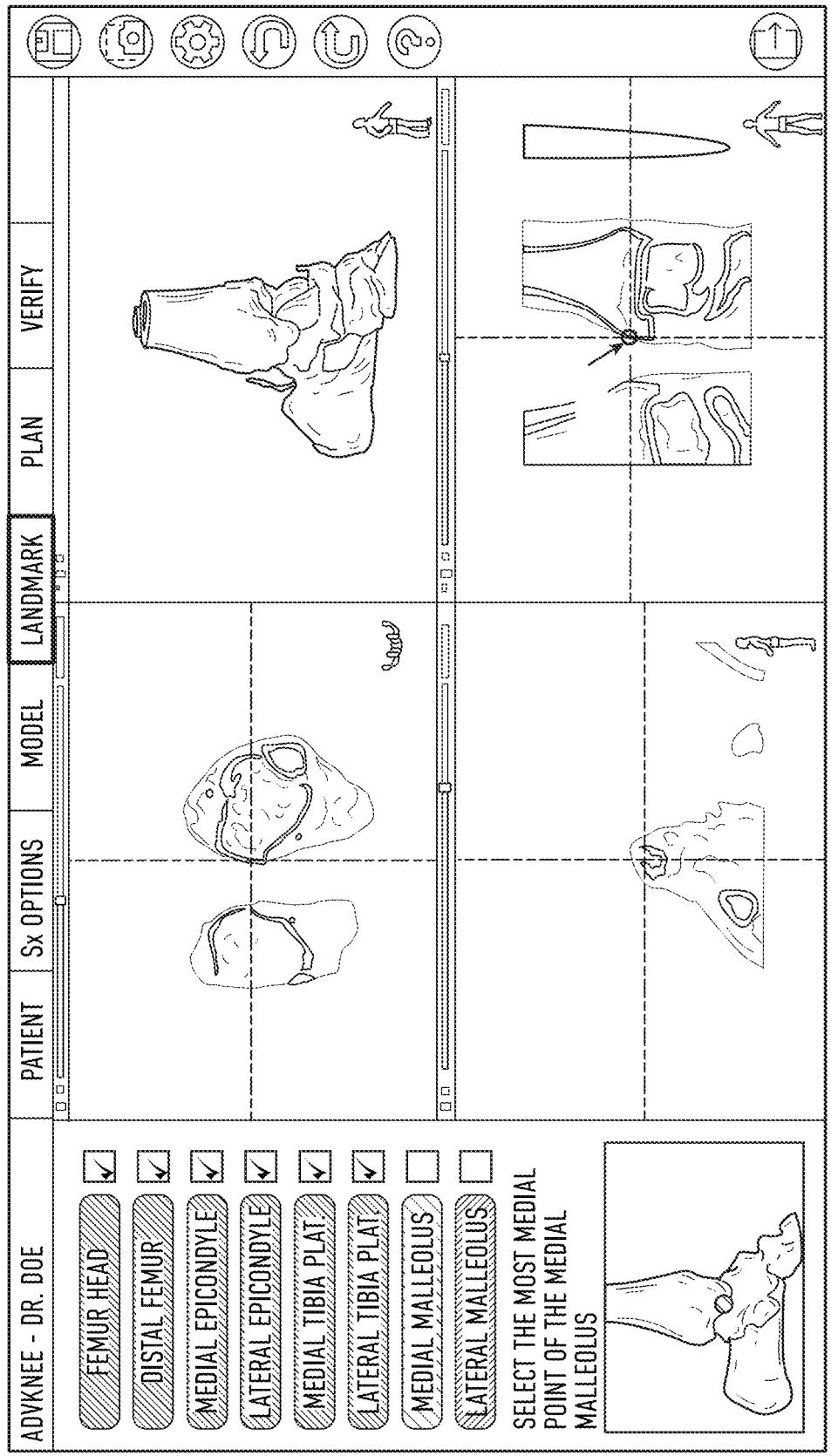
FIG. 22 is a sample user-interface of an application for use with the system of FIG. 1, which facilitates anatomical landmarking for another portion of the anatomy of the subject.
Figure 23:
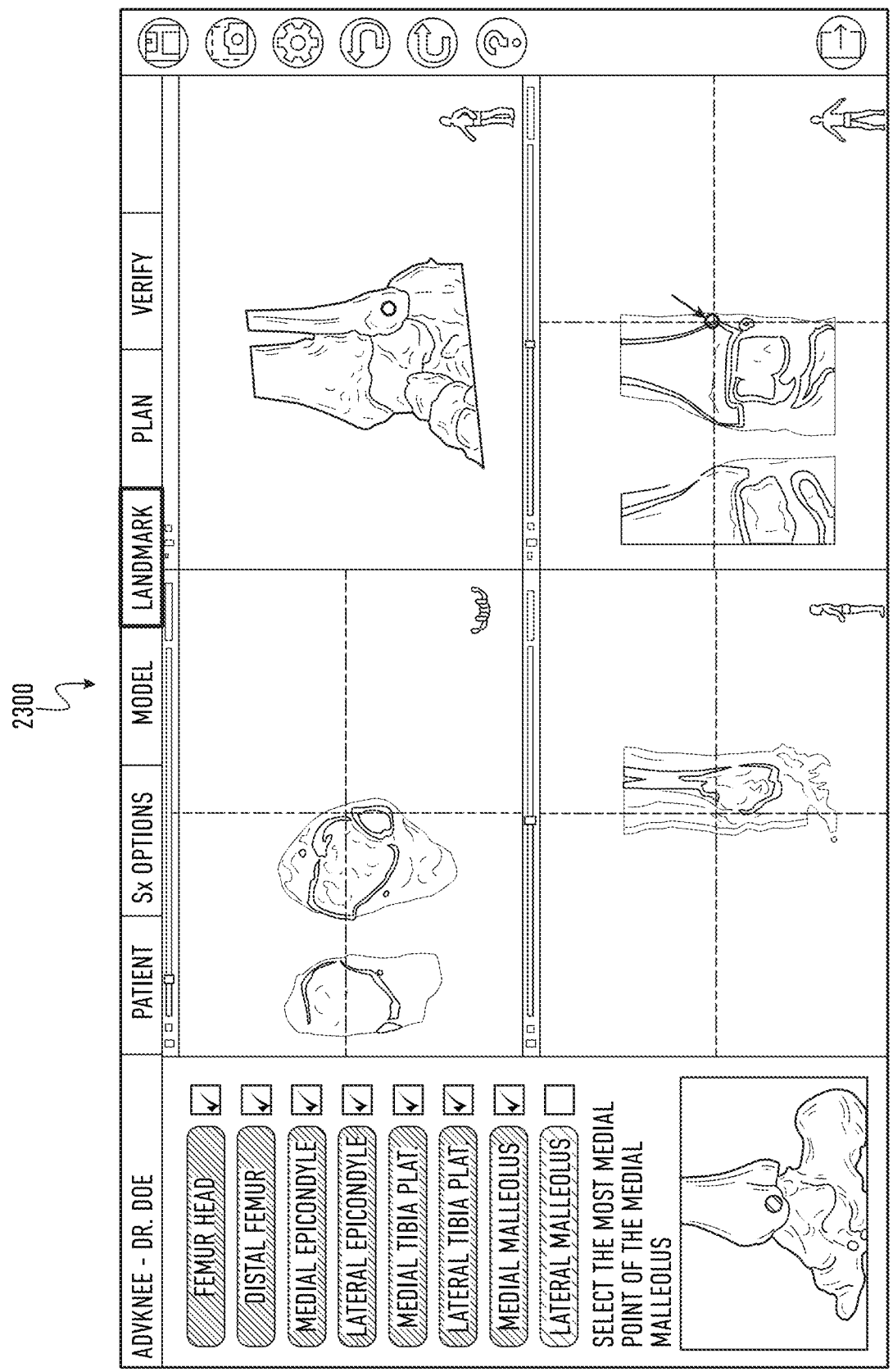
FIG. 23 is a sample user-interface of an application for use with the system of FIG. 1, which facilitates anatomical landmarking for another portion of the anatomy of the subject.
Figure 24:
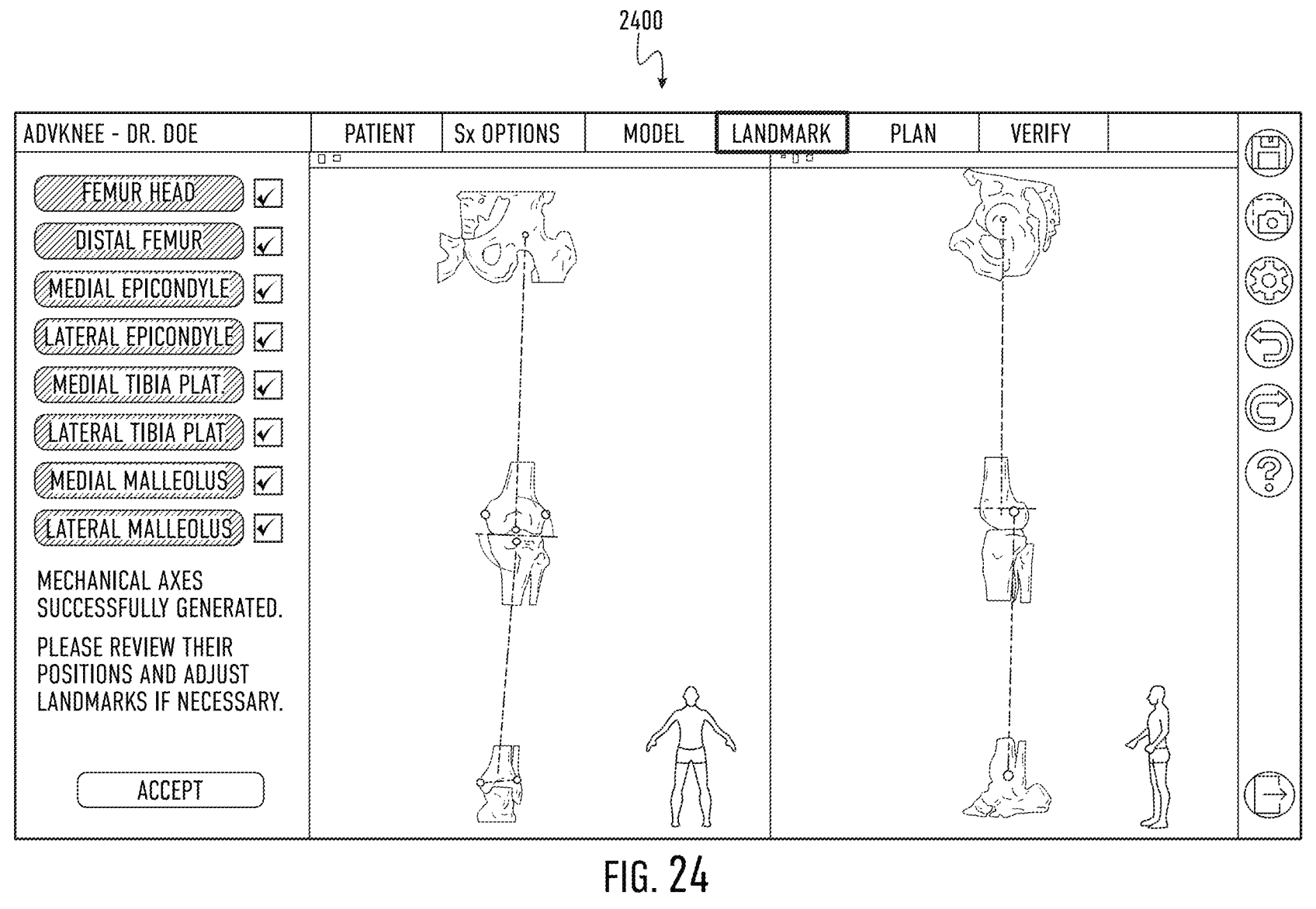

Once the landmark point is defined for the medial epicondyle, the program may proceed to interface screen 1900, as shown in FIG. 19. Interface screen 1900 may be utilized for landmarking the lateral epicondyle. As with the other landmarks, the surgeon may use a 3D cursor to find the anatomical region shown in the guide picture, may use any of the views to define the new anatomical landmark with the click of a mouse (or other input), and may click on any landmark item in the left panel list to redefine any desired landmark. For example, interface screen 2000 of FIG. 20 may be utilized to landmark the medial tibia plateau, interface screen 2100 of FIG. 21 may be utilized to landmark the lateral tibia plateau, interface screen 2200 of FIG. 22 may be utilized to landmark the medial malleolus, the interface screen 2300 of FIG. 23 may be utilized to landmark the lateral malleolus, and so forth. Once all of the landmarks are defined, user interface screen 2400 of FIG. 24 may be displayed to the surgeon for final review of all of the landmarks. In certain embodiments, the alignment of the particular limb (or other anatomy of interest) may be determined from the landmarks. The interface screen 2400 may enable the viewers rendered therein to show an overview of the anatomy with defined axes (e.g. mechanical axis of femur and tibia, epicondylar and malleolar axes). The interface screen 2400 may also enable the surgeon to go back and adjust previously completed landmarks. Once the surgeon is done with landmarking, the surgeon can accept the landmarks and proceed to the implant position planning stage of the planning process.

Figure 25:
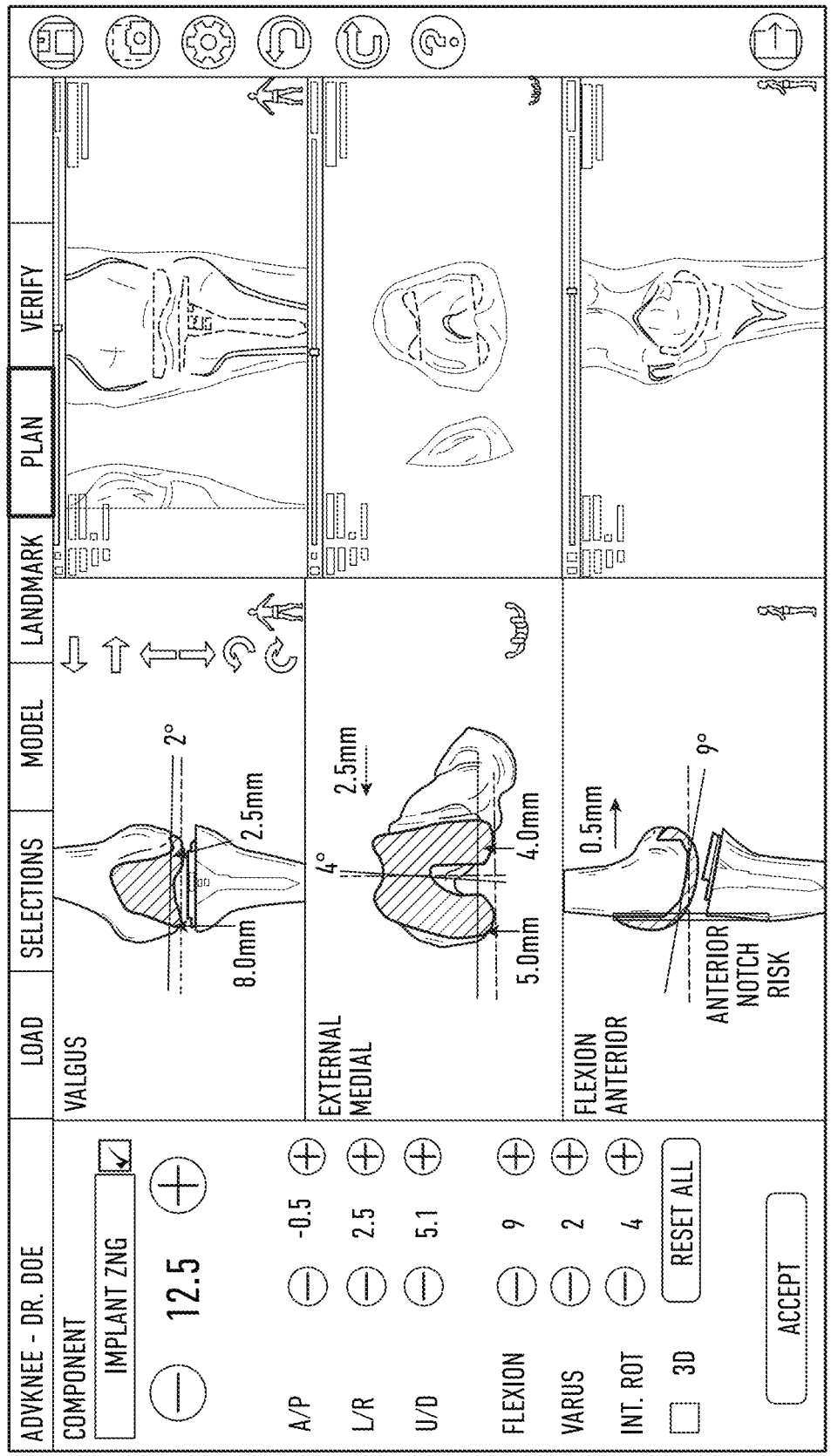
FIG. 25 is a sample user-interface of an application for use with the system of FIG. 1, which facilitates implant planning for a component.
Figure 26:
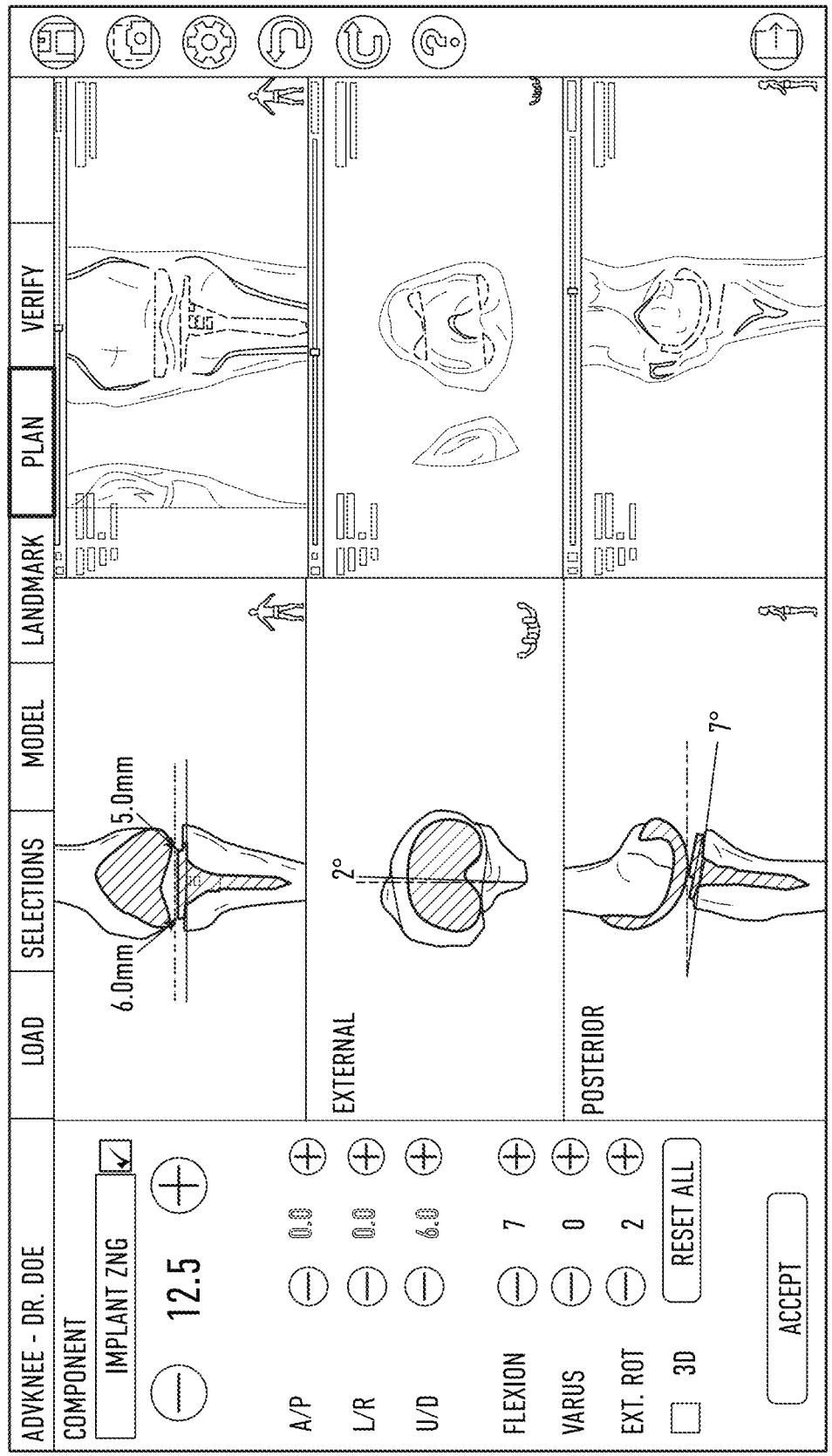
FIG. 26 is a sample user-interface of an application for use with the system of FIG. 1, which facilitates implant planning for another component.
Figure 27:
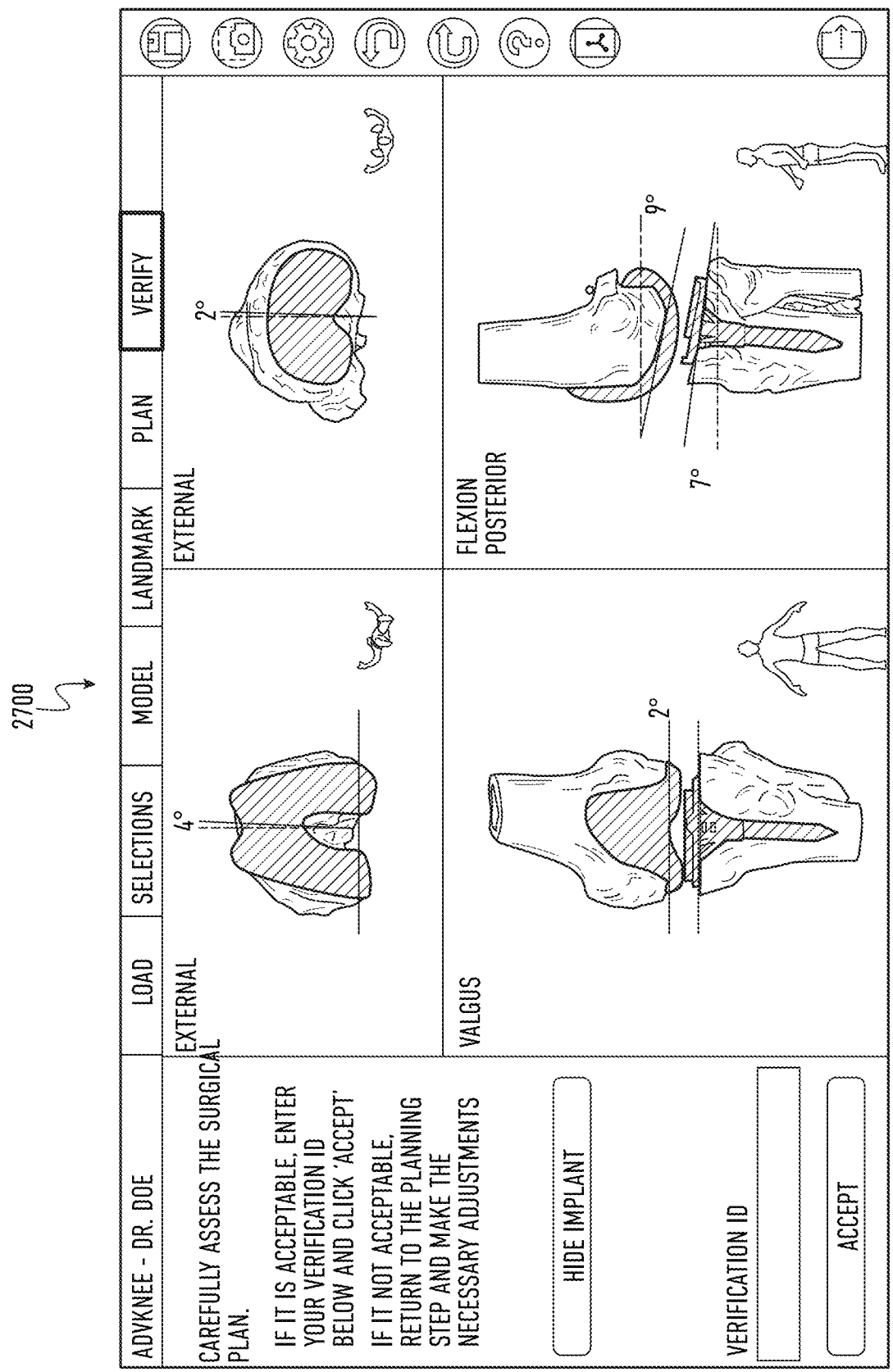
FIG. 27 is a sample user-interface of an application for use with the system of FIG. 1, which facilitates verification and approval of implant positioning.
Figure 28:
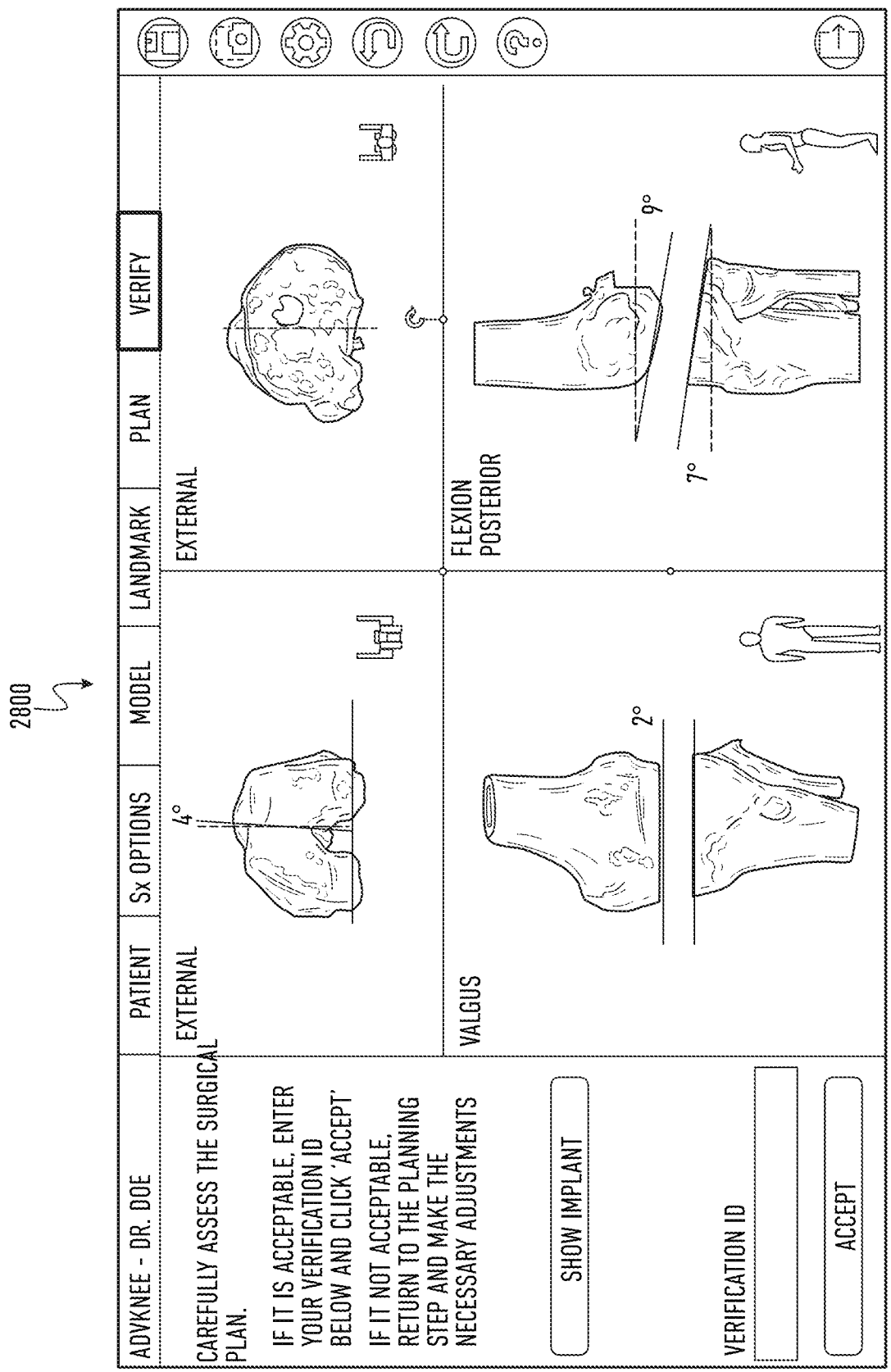
FIG. 28 is a sample user-interface of an application for use with the system of FIG. 1, which provides a view option to hide implants to observe cut lines in relation to the subject's anatomy during the verification and approval of implant positioning.
Figure 29:
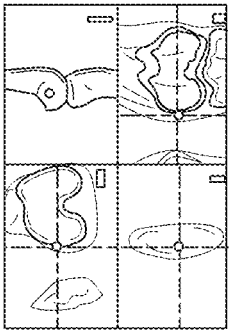
FIG. 29 is a sample user-interface of an application for use with the system of FIG. 1, which provides the ability to initiate new plans or edit existing plans.

At the implant position planning stage, user interface screen 2500 may be rendered, as shown in FIG. 25. By way of example, the femoral component of the implant may be initially positioned based on the defined anatomical landmarks. In certain embodiments, fine tuning of the position may be provided along anatomical axes, as shown in the left panel. In certain embodiments, fine tuning may also be enabled along implant axes, such as in 3D views when the mouse (or other input mechanism) is moved over. In certain embodiments, metrics and warnings may be dynamically shown over the 3D views as the implant position changes in real time. User interface screen 2600 of FIG. 26 shows the tibial component of the implant, which may also be positioned via the program. Once the tibial component is positioned, user interface screen 2700 of FIG. 27 may be rendered and displayed. A summary of the implant position metrics may be displayed in relation to the subject's anatomy. If the surgeon agrees with the positioning in relating to the anatomy, the surgeon may verify and approve the plan accordingly. In certain embodiments, a view option to hide implants may also be provided to enable the surgeon to observe cut lines in relation to the subject anatomy, as shown in user interface screen 2800 of FIG. 28. The surgeon may be provided with the ability to go back to modify any of the planning steps using the tabs at the top of the user interface screens in the FIGS. 5-29. The plan may be accepted by requiring confirmation of user authentication and verified plans may be locked for editing. Once the plan is verified for the surgical implant and procedure, the surgeon may be brought back to the browser screen where either new plans may be initiated, or editing of existing plans may be continued, as is shown in interface screen 2900 of FIG. 29. The surgeon may then proceed with conducting the surgical procedure on the subject using the plan.

Figure 30:
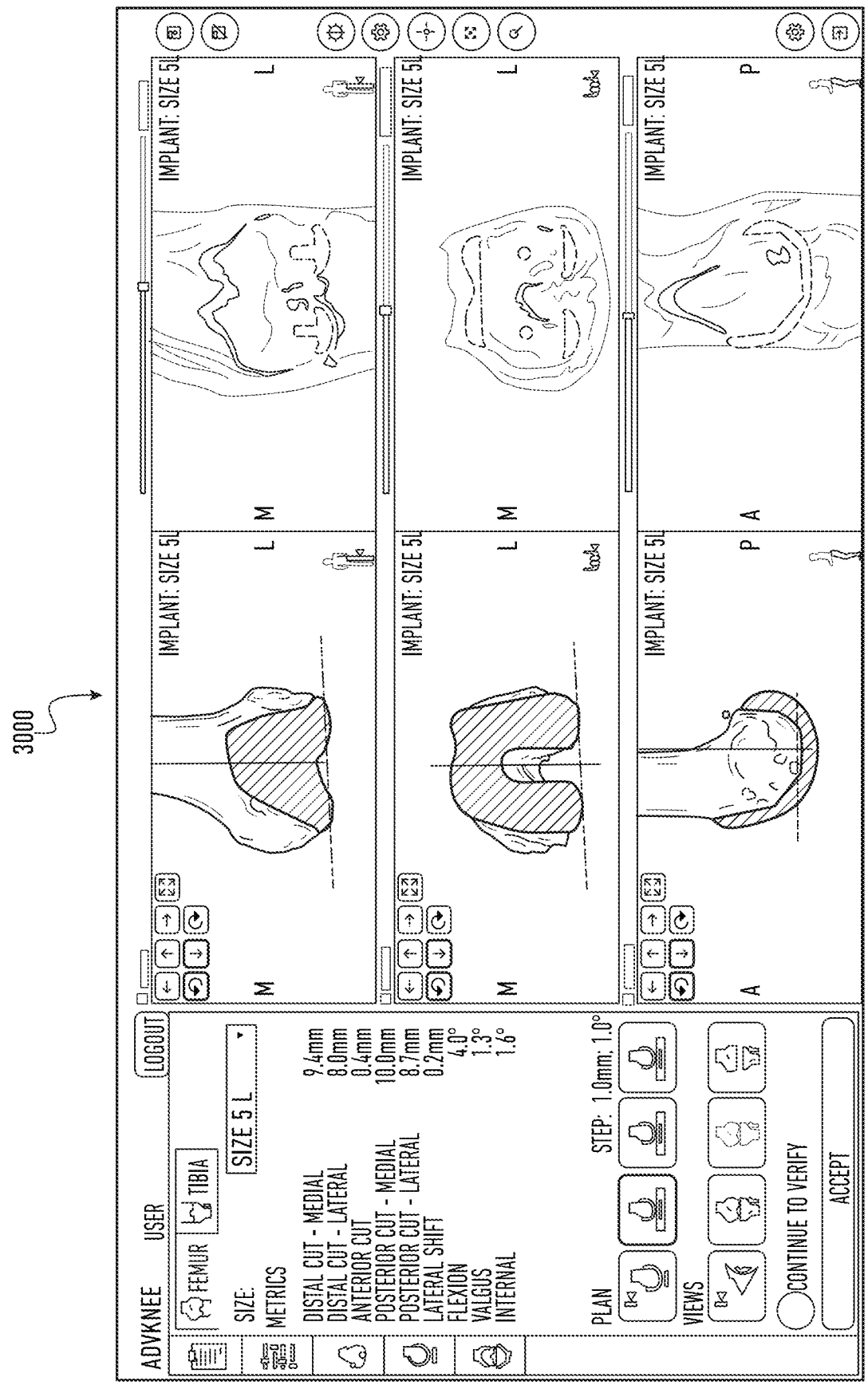
FIG. 30 is a sample user interface for use with the system of FIG. 1 and for facilitating surgical planning and guidance with three-dimensional visualization according to an embodiment of the present disclosure.
Figure 31:
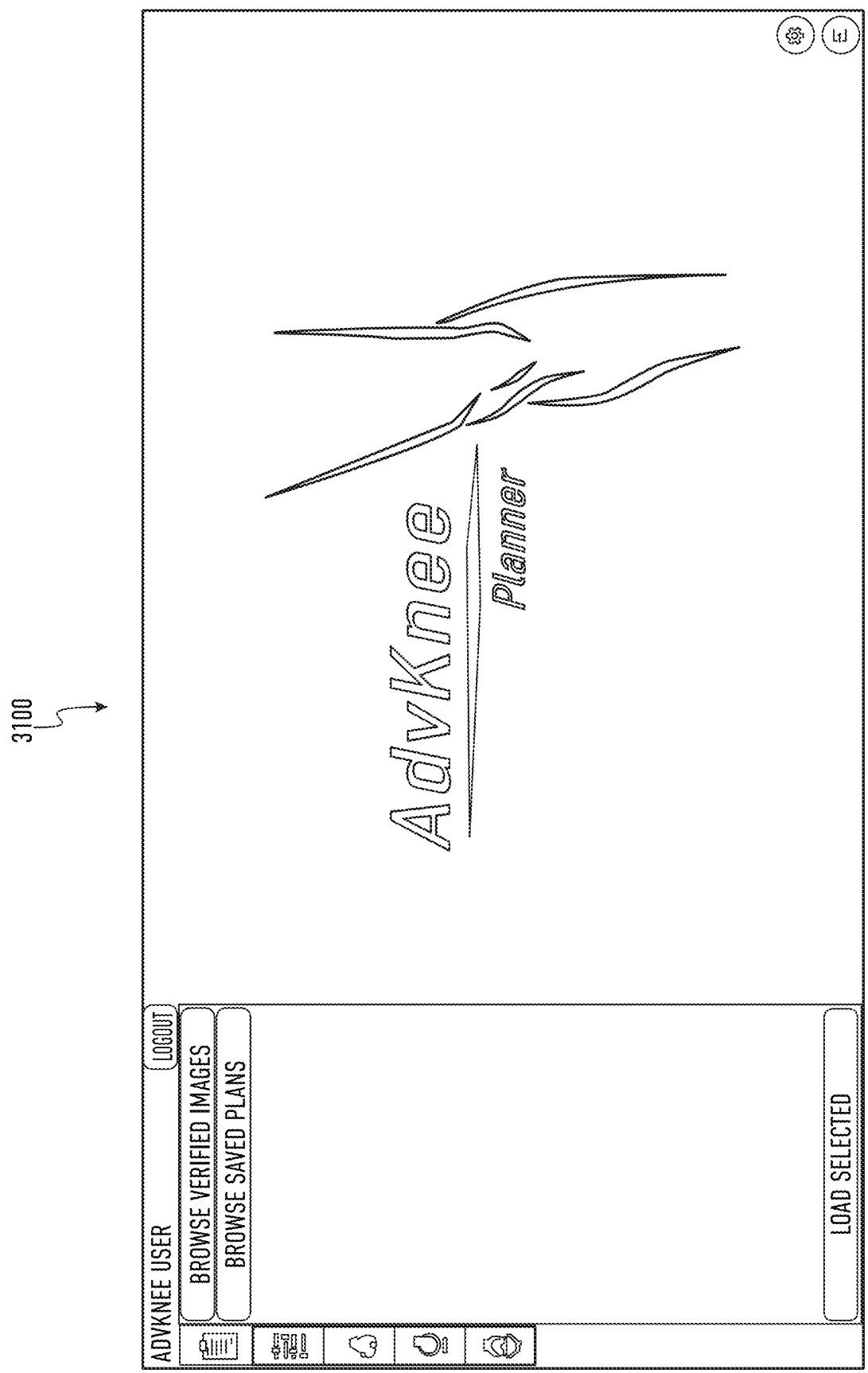
FIG. 31 is a sample user-interface of an application for use with the system of FIG. 1, which enables a user to authenticate into the system and access features and functionality of the system.

Referring now also to FIGS. 30-54, an additional process flow for using the program/application providing the operative functionality of the system 100 is shown. For example, the process flow may be utilized to generate a plan for a surgical procedure, such as for implanting an implant onto an anatomy of interest of a subject. In certain embodiments, the process flow, features, and functionality associated with FIGS. 5-29 may be combined, supplemented, and/or modified based on the process flow, features, and functionality associated with FIGS. 30-54. The process flow may incorporate the use of a digital surgical planner implemented via software, hardware, or a combination of hardware and software. The planning software may utilize volume-rendered image (or other media content) data to generate a more informed and faster planning system to determine the optimal patient-specific placement and size for an implant. In certain embodiments, the system 100 may be extensible to allow for the addition of various types of implant systems. The planning system may include a user interface that may present various types of controls to a user (e.g., a physician) to control the software supporting the functionality of the system 100. For example, FIG. 30 illustrates an exemplary user interface 3000 that may be configured to receive various inputs (e.g., touchscreen inputs, mouse inputs, voice commands, text inputs, commands, etc.) from a user to facilitate the surgical planning and/or other processes described herein. In certain embodiments, user interface 3000 may include task tabs (i.e., steps), as shown on the left side of the user interface 3000. The task tabs may have language independent icons to identify them and may be disabled (e.g., grayed out) until certain prerequisites are satisfied (e.g., a planning step may only be available once landmark identification for a particular anatomy of interest has been completed by the system 100 and/or a user of the system 100). The user interface 3000 may also include task controls, which may appear immediately to the right of the task tabs (i.e., steps) and provide function and information specifics for the current task at hand. The user interface 3000 may also include a workspace area that may occupy a significant portion of the user interface 3000, such as to the right of the task controls. In certain embodiments, the workspace may include information to the user of the planning software, such as, but not limited to, images of the current implant placement, angle information for the implant, distance information with respect to certain areas of interest, any other information, or a combination thereof. The workspace may also include controls for working within the workspace (e.g., such as to modify implant placement, change the implant characteristics, etc.). The user interface screen 3000 may also include system controls (e.g., positioned on the far right of the user interface screen 3000) that may be utilized to set user preferences, save current surgical plans and/or edits, exit the current planning session, and perform a variety of other tasks and/or functions.

Figure 32:
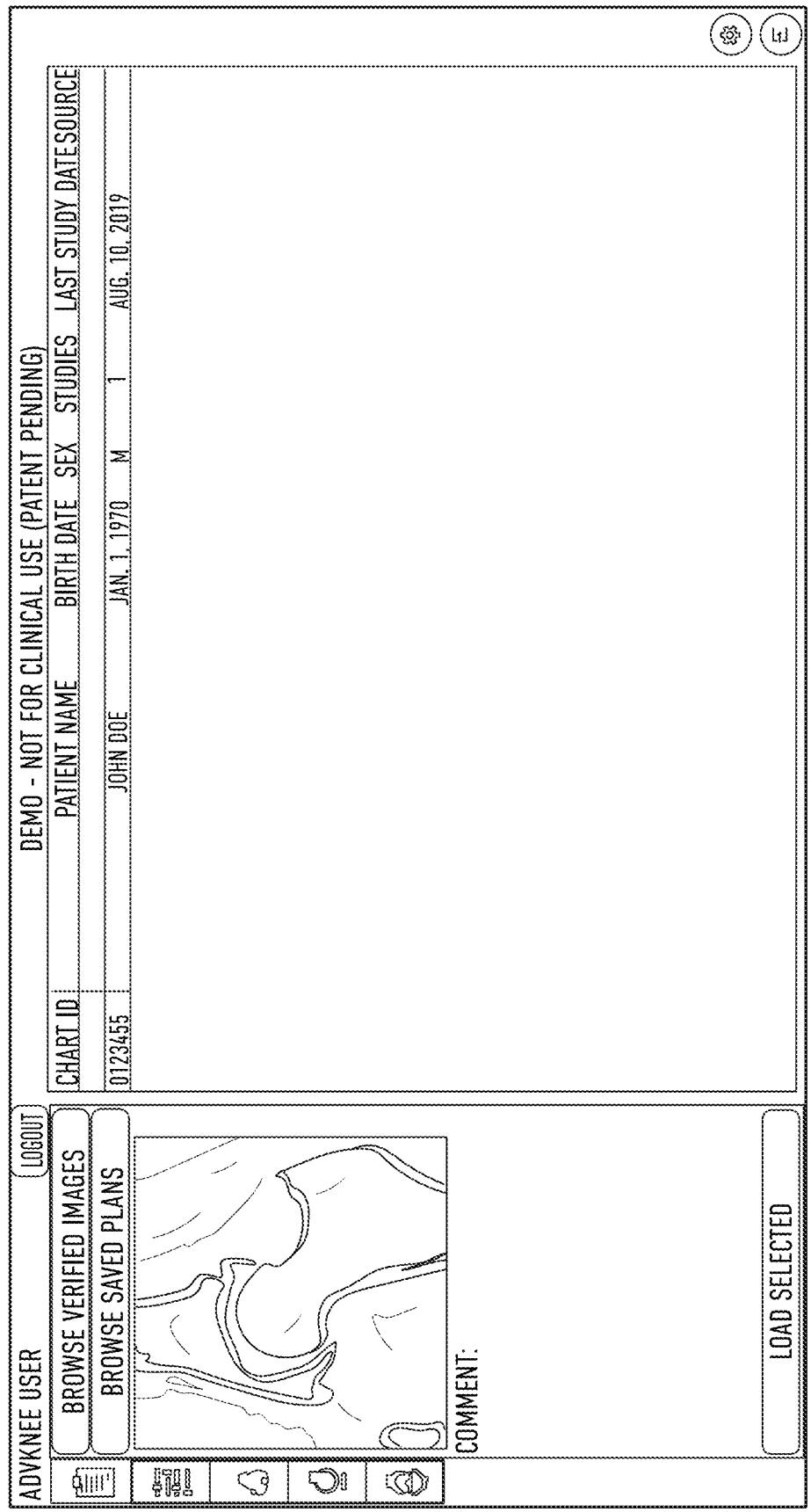
FIG. 32 is a sample user-interface of an application for use with the system of FIG. 1, which enables a user to browse various images stored by or made accessible to the system.
Figure 33:
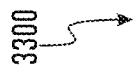
FIG. 33 is a sample user-interface of an application for use with the system of FIG. 1, which enables a user to browse various surgical plans stored by or made accessible to the system.
Figure 34:
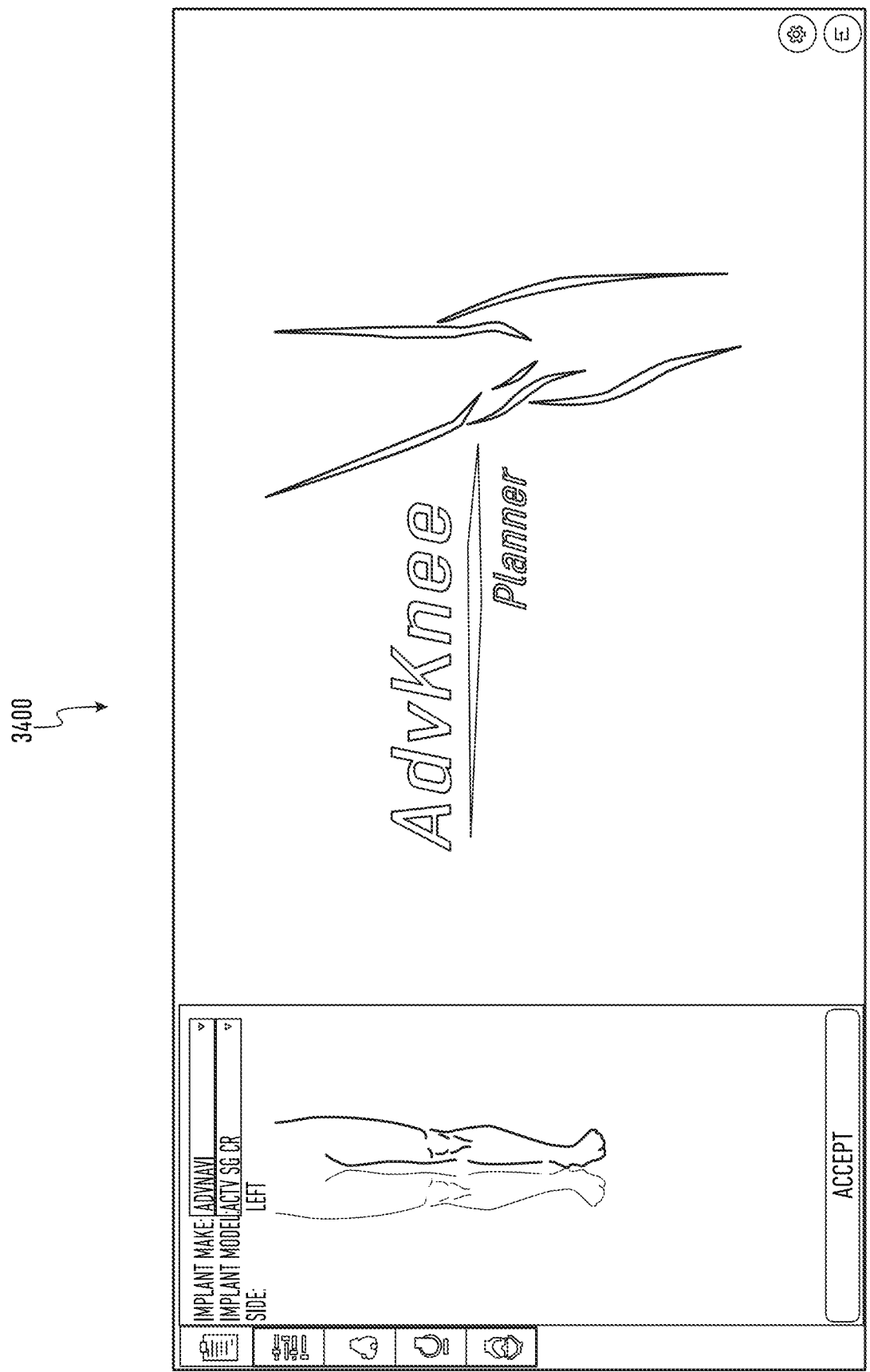
FIG. 34 is a sample user-interface of an application for use with the system of FIG. 1, which enables selection of various options.
Figure 35:
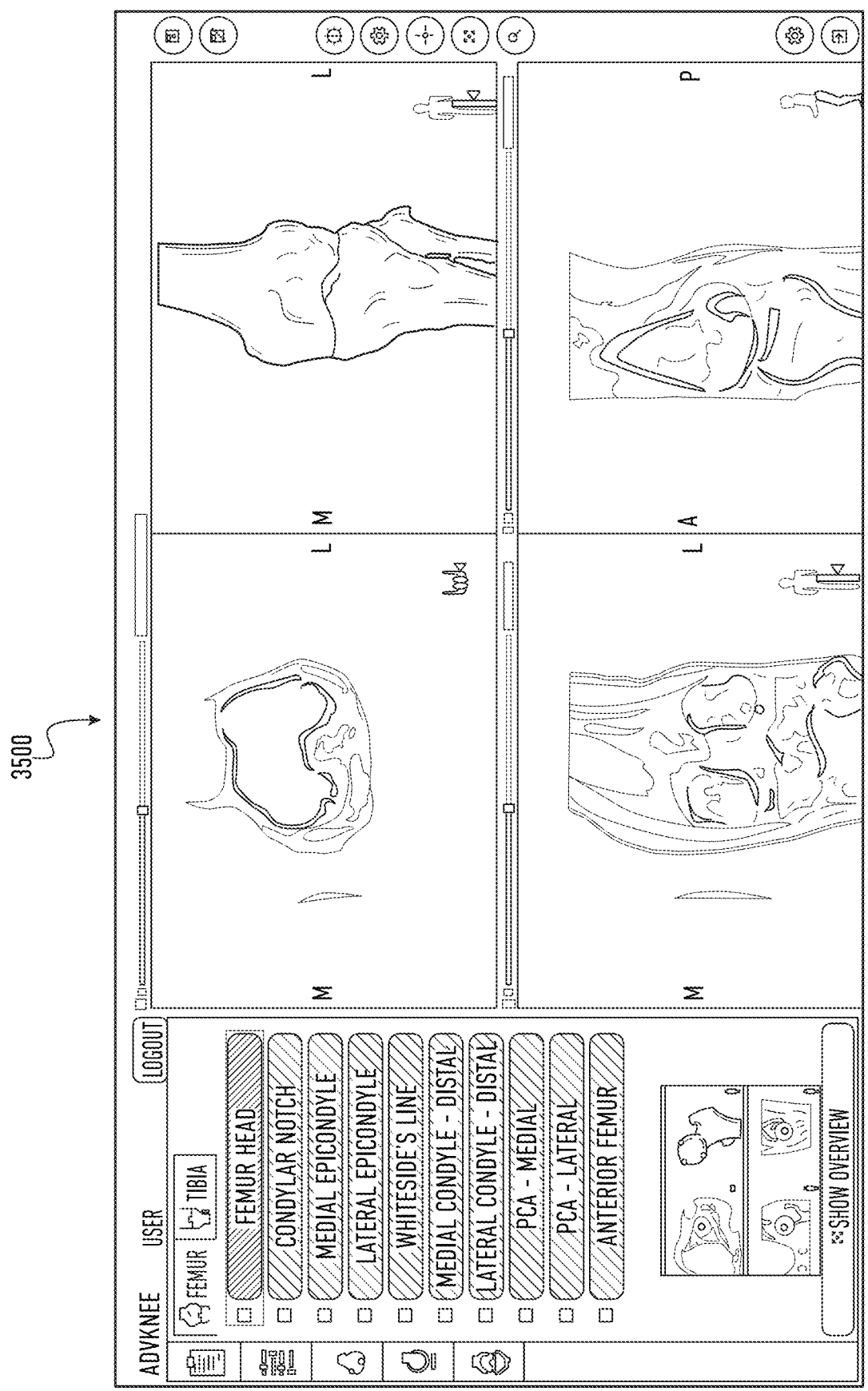
FIG. 35 is a sample user-interface of an application for use with the system of FIG. 1, which facilitates the selection of landmark points for an anatomy of interest.

In certain embodiments, when the application supporting functionality of the system 100 is opened, the user interface 3100 may be presented to a user of the system 100. The user interface 3100 may enable the user to enter login credentials (e.g., username/password combinations, etc.). If the user is unable to authenticate, the system 100 may prevent the user from access the system 100 and/or any features of the system 100. Additionally, the system 100 may prevent the user from accessing patient data. As a result, the application may ensure that only those who are authorized and able to authenticate into the application are given access to patient data and the functionality of the planning functionality of the system 100. In certain embodiments, if the user can login successfully, the application may enable the user to access user-specific preferences that may be utilized to tailor the application functionality to the specific user's preferences. In certain embodiments, once the user is able to authenticate into the application, the system 100 may display user interface screen 3200, as shown in FIG. 32. User interface 3200 may be displayed, such as when the user initiates a new surgical planning session. In certain embodiments, user interface screen 3200 may allow the user to digitally browse through available image data (or other media content). Once an image(s) of interest is located, the user interface may enable the user to preview the image via an image preview pane to aid in selection of the correct imaging set for a particular surgical procedure. In certain embodiments, the image may be selected and may be displayed in a full-size mode outside of the preview pane. In certain embodiments, the system 100 may also enable the user to browse various surgical plans, as shown in user interface screen 3300 of FIG. 33. For example, user interface 3300 may provide the option for the user to browse previously saved surgical plans and select one or more plans. Selected plans may be reviewed further, modified, and/or verified by the user, such as via the application controls of the application. In certain embodiments, the user interface 3300 may display a preview of a saved plan that shows the view that was shown when the plan was originally saved in the application. The application may also enable the user to view and select various different surgical options, such as is shown in the user interface 3400 of FIG. 34. In certain embodiments, the default implant selection options may be based on user-specific preferences specified for the user. In certain embodiments, the default may be adjusted on user interface 3400 to any of the integrated implant systems that may be licensed for use with the system 100 as well. In certain embodiments, the default surgical side may be based on information contained within imaging data of an anatomy of interest. The selection may be changed if desired by the user as well. If the selected operative surgical side (e.g., the side selected by the user) is not consistent with the corresponding imaging data, the system 100 may generate a warning or alert that may be visually rendered on the user interface 3400 and/or audibly outputted via a speaker of the system 100.

In addition to enabling the user to select surgical options, the application may also enable the user to conduct landmarking for an anatomy of interest. For example, user interface 3500 of FIG. 35 may be utilized by a user to conduct the landmarking. In the landmarking task, various aspects of a subject's (e.g., patient) anatomy may be defined. This process may allow for the definition of key points and axes to support the creation of patient-specific metrics for the placement and sizing of a selected implant. Proper landmark definitions ensure accurate metrics and also the determination of the optimal implant position and size for a particular subject. The user interface screen 3500 may enable the user to select a particular landmark name (e.g., femur head as shown in user interface screen 3500). Selecting the landmark name may cause the images in the workspace area of the user interface to snap together for the landmark using an adaptive, smart algorithm based on the knowledge of the anatomy of the subject, the imaging protocol, and previously selected landmarks. In certain embodiments, this process may serve to enhance the speed of the landmarking process for the user. In certain embodiments, a digital mannequin (e.g. avatar) may be displayed on the user interface screen 3500 at the bottom right of each image to indicate the view orientation and to remind the user of the selected operative side of the subject (e.g. the right side of the subject is where the surgery will be performed) and assist the user in interpreting the orientation of the image(s). In certain embodiments, a guide image to aid in landmark selection may be provided below the list of possible landmarks displayed on the user interface screen 3500. The guide image may be updated by selecting a landmark name from the list of selectable landmark names. Selecting the guide image may display a window with more detailed information on how to correctly select the current landmark via the application. In certain embodiments, holding an input button (e.g. shift button) on a keyboard while moving the mouse over the anatomy in the 3D image rendered via the user interface screen 3500 may cause digital crosshairs to be displayed and centered on the mouse cursor and for all three two-dimensional views to be updated to the slice that intersects with the center of the crosshairs. In certain embodiments, a slider may be positioned at the top of each two-dimensional view and may be utilized to scroll through the two-dimensional slices in that view.

Efficiently placing the points for landmarks may follow a process, such as, but not limited to the following: (1) click the landmark button on the user interface screen 3500 to enable the placement of the landmark of interest; (2) use Shift (or other desired key) while hovering and moving over an image to align all views, repeating on images until the crosshairs in each view match where the landmark point should be placed; (3) click an image at the desired location to place the landmark point; and (4) repeat steps (2) and (3) for each point of a multi-point landmark. Once a landmark has been created via the application, it may be locked for editing, unless it is the currently selected landmark. In order to move the currently selected landmark, the user may select the visually rendered circular handle (or one of the circular handles of a multi-point landmark) and drag it to a new location. In certain embodiments, clicking on a landmark handle may update the other views to show the slice within which the handle exists.

Figure 36:
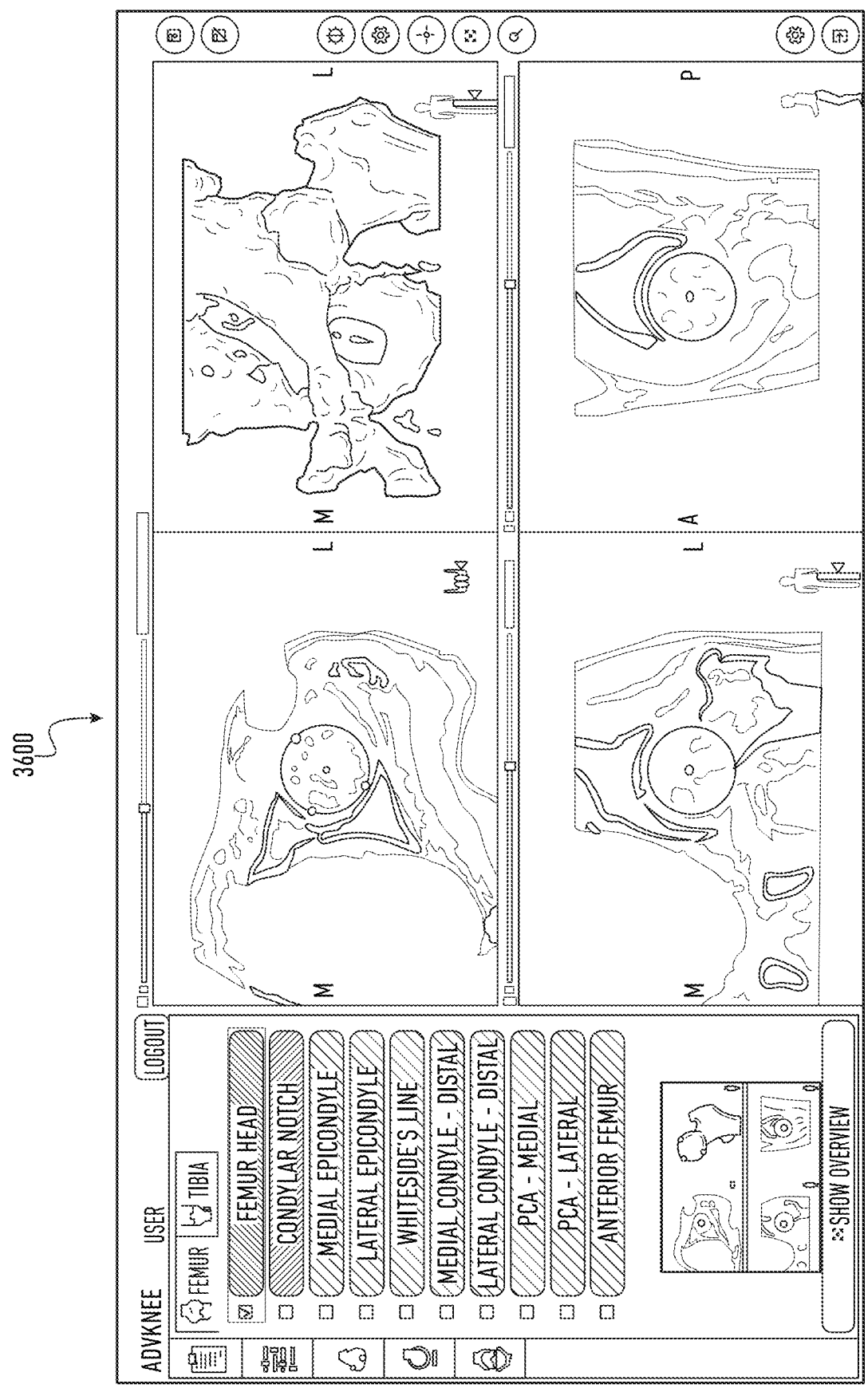
FIG. 36 is a sample user-interface of an application for use with the system of FIG. 1, which facilitates femoral landmarking using a femur head.
Figure 37:
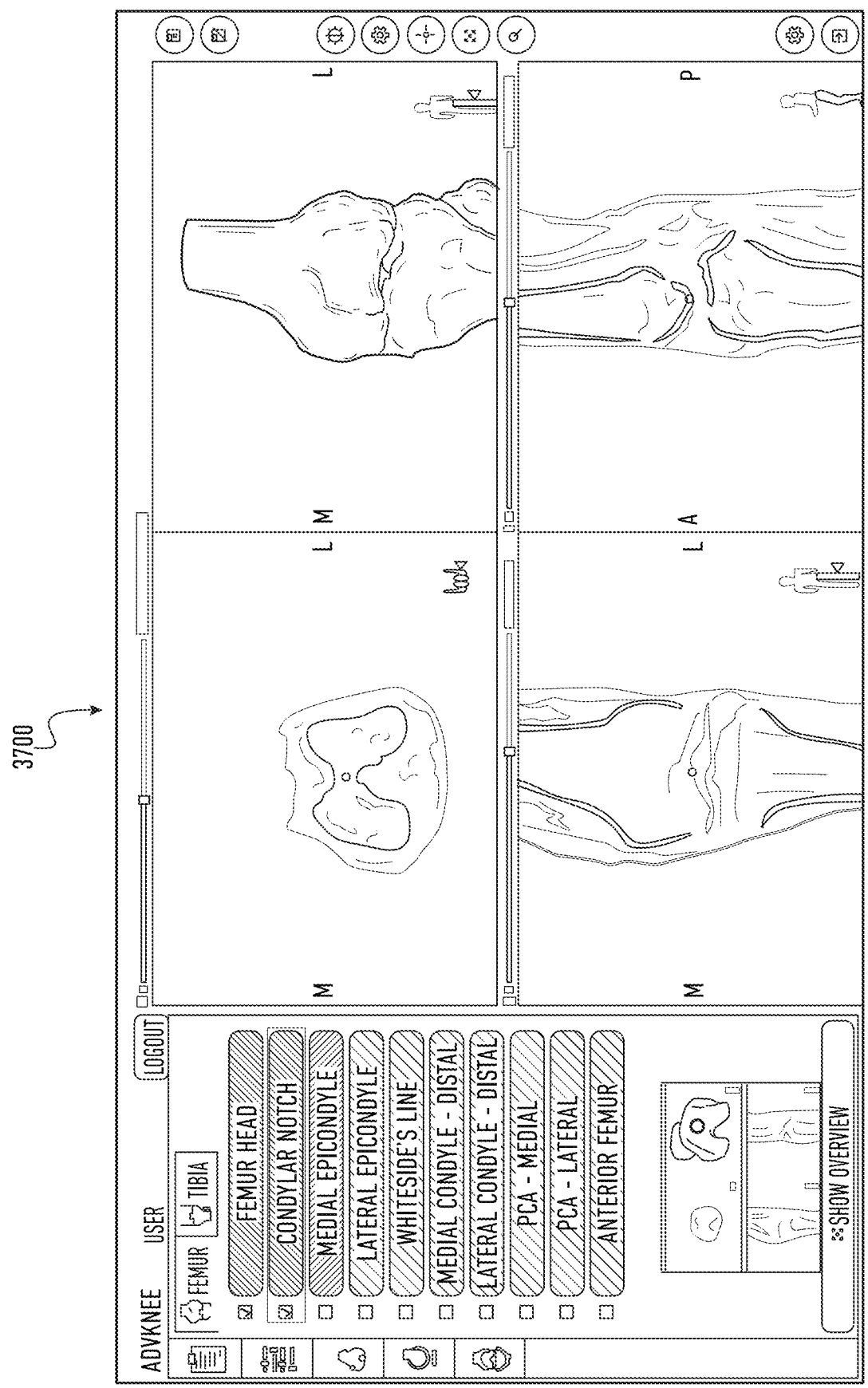
FIG. 37 is a sample user-interface of an application for use with the system of FIG. 1, which facilitates femoral landmarking using a condylar notch.
Figure 38:
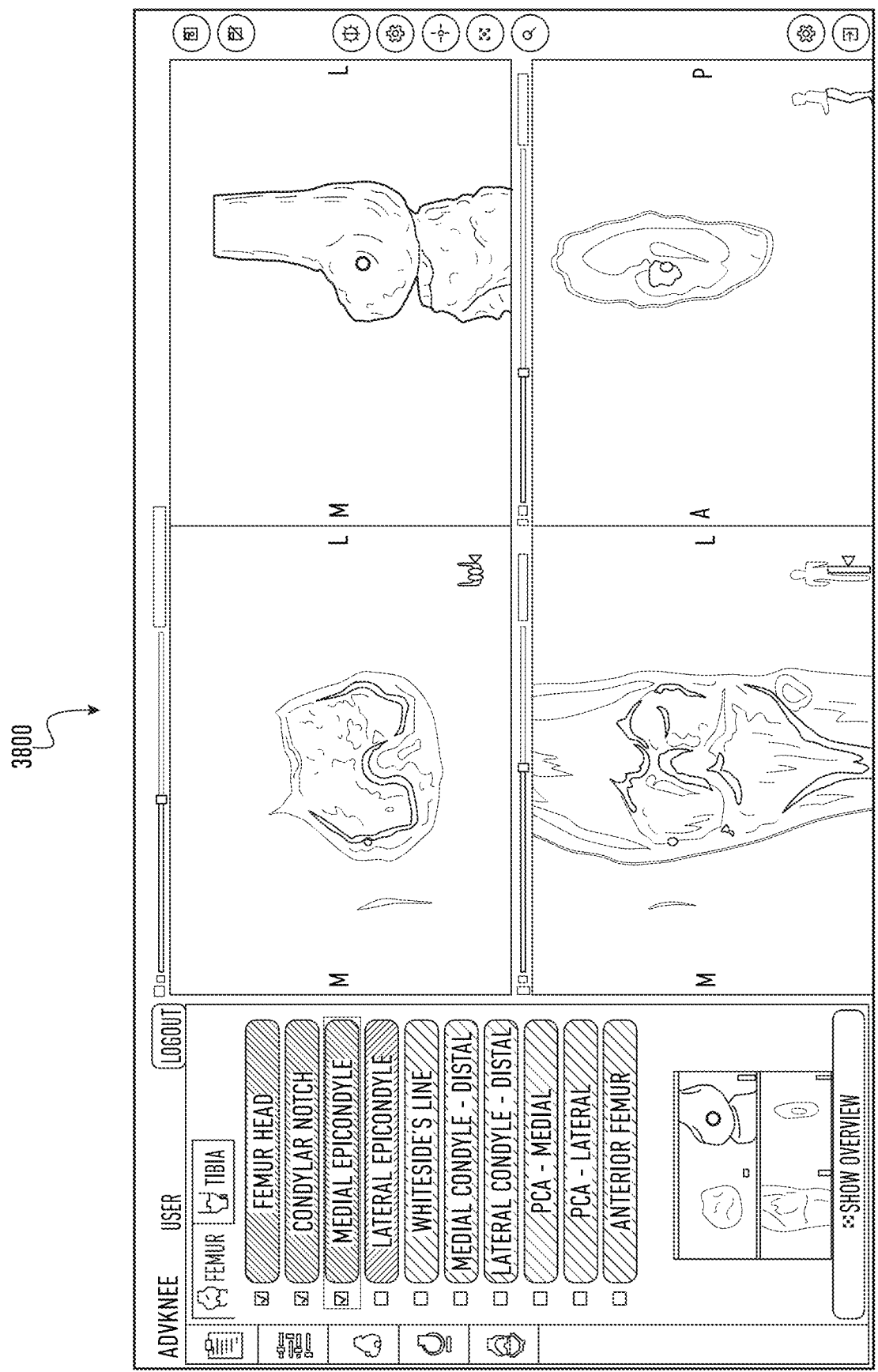
FIG. 38 is a sample user-interface of an application for use with the system of FIG. 1, which facilitates femoral landmarking using epicondyles.
Figure 39:
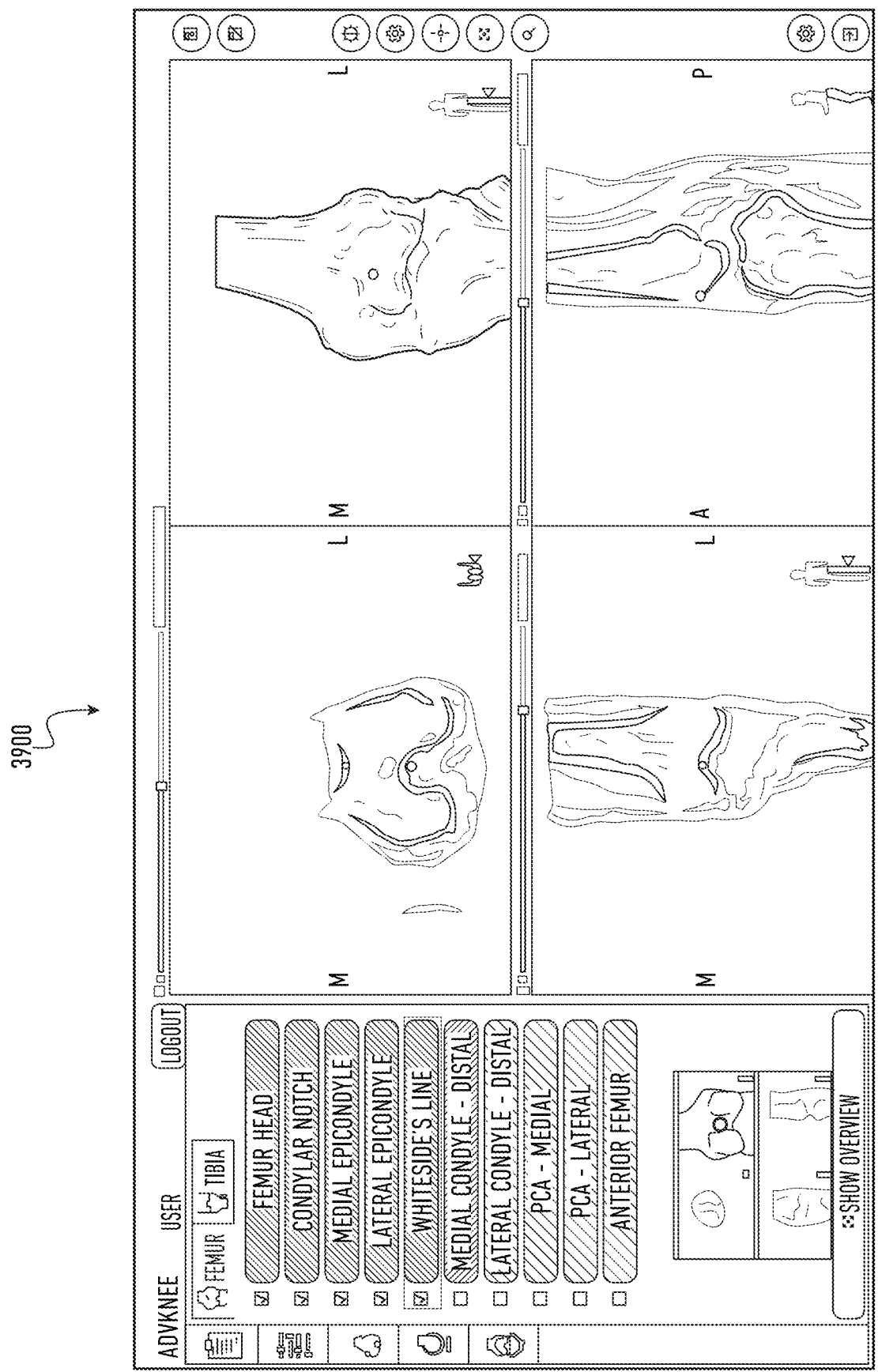
FIG. 39 is a sample user-interface of an application for use with the system of FIG. 1, which facilitates femoral landmarking using Whiteside's Line.
Figure 40:
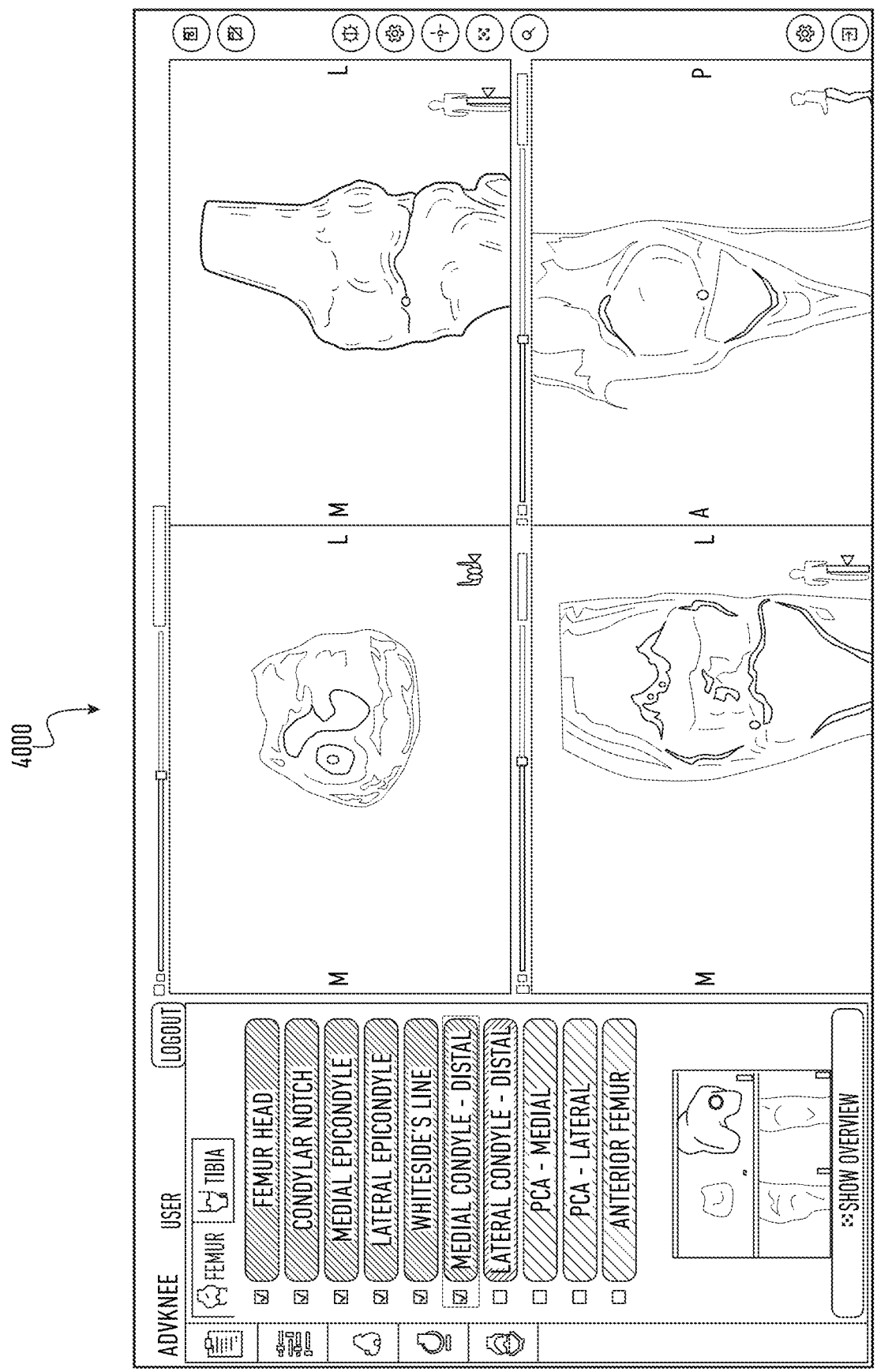
FIG. 40 is a sample user-interface of an application for use with the system of FIG. 1, which facilitates femoral landmarking using distal condyles.
Figure 41:
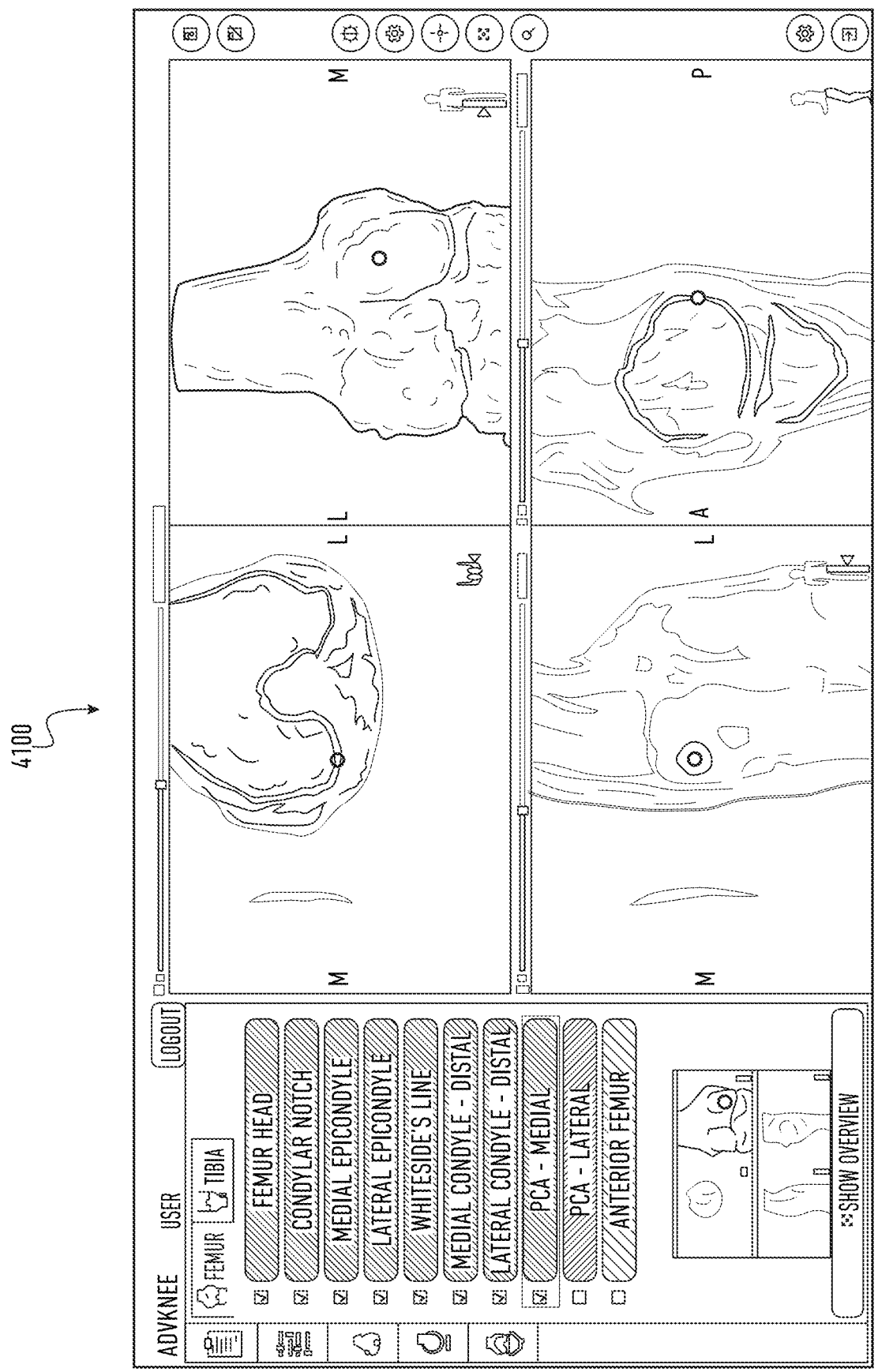
FIG. 41 is a sample user-interface of an application for use with the system of FIG. 1, which facilitates femoral landmarking using posterior condylar axis points.
Figure 42:
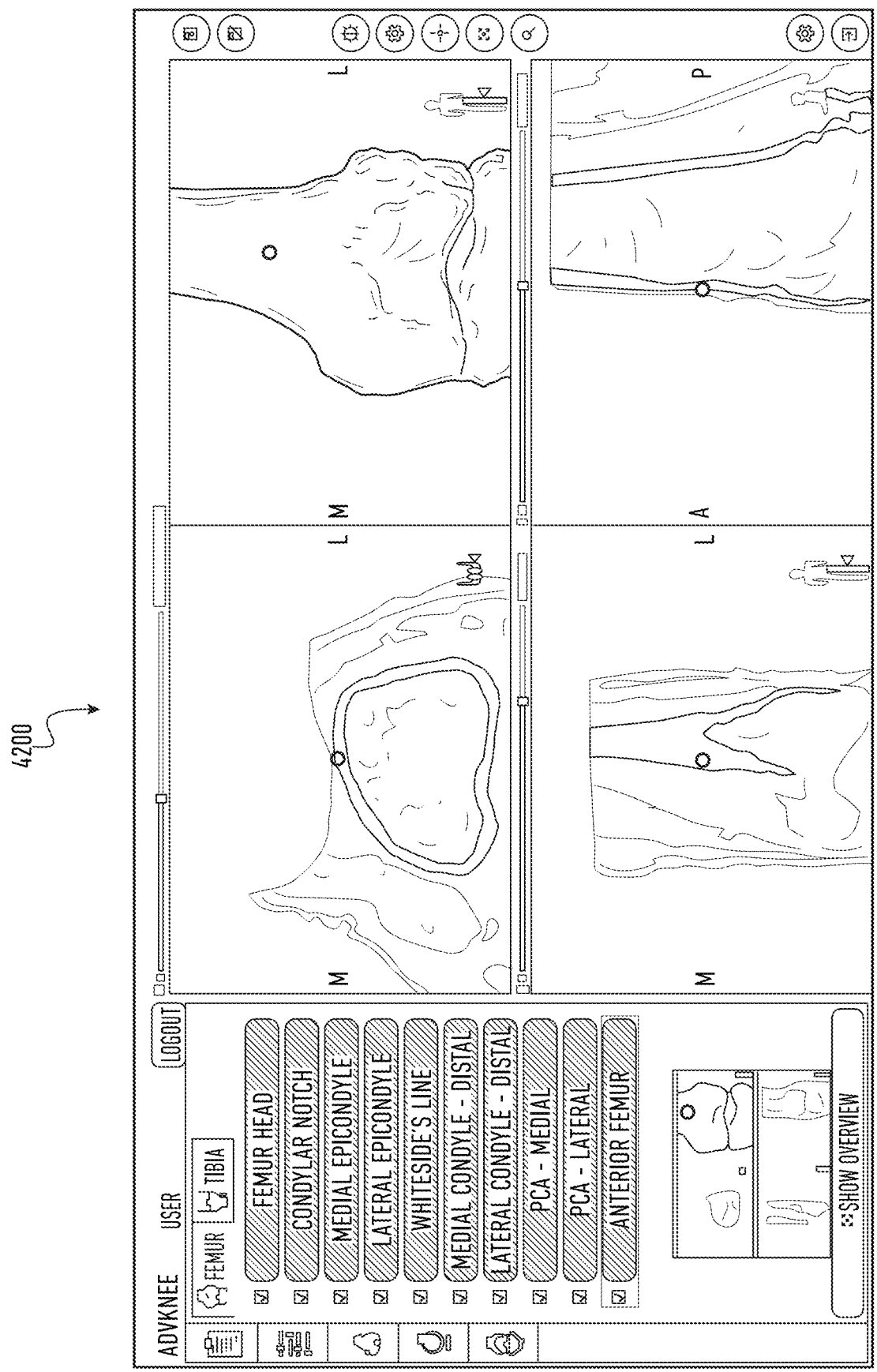
FIG. 42 is a sample user-interface of an application for use with the system of FIG. 1, which facilitates femoral landmarking using an anterior femur.

Referring now also to FIGS. 36-42, user interfaces 3600-4200 for facilitating femoral landmarking using the system 100 are illustrated. In FIG. 36, user interface screen 3600 depicts a femur head of a subject. The femur head center may be important to determining the mechanical axis of the femur. The center of the femur head may be defined by describing a sphere that encompasses the head. The center of the sphere may represent the center of the femur head. In certain embodiments, the user interface screen 3600 may enable the user to select multiple points (e.g., three points) on the edge of the femur head in one of the two-dimensional image slices. The center may be calculated and displayed via the user interface screen 3600. The user may then click on a dot representing the center and other views may be updated to show this same point. In certain embodiments, if necessary, the user may click and drag the center dot in the images until the outer circle fits the femur head in all three views. In FIG. 37, user interface screen 3700 illustrates the condylar notch which, along with the center of the femoral head, may be utilized to determine the mechanical axis of the femur. The user interface screen 3700 may enable the user to select the point that is most superior in the intercondylar notch. User interface screen 3800 of FIG. 38 illustrates the epicondylar points that define the epicondylar axis. The epicondylar points may be most easily selected on the three-dimensional image, and, for each epicondyle, the user may click the landmark button and select the corresponding medial or lateral point in the image. User interface screen 3900 of FIG. 39 depicts Whiteside's Line, which defines the anteroposterior axis of the femur. The user may scroll the axial two-dimensional view such that the view shows a deep anterior trochlear groove. The user may then place the anterior point at the deepest spot of the anterior groove. The user may then place the posterior point such that it (or the line shown) may intersect the deepest point of the posterior trochlear groove. User interface screen 4000 of FIG. 40 illustrates the distal condyle points that may be used to calculate distal resection for a subject. The distal condyle points may be most easily selected in the axial two-dimensional view. In certain embodiments, for each condyle, the user may scroll the axial view to show the most distal aspect of the condyle and then select it to place the landmark at that location. User interface screen 4100 of FIG. 41 illustrates the posterior condylar axis. Posterior condyle points may be utilized to determine the amount of posterior resection and the posterior condylar axis. For each condyle, the user may select the point that is most posterior. The selection may be most easily performed on the coronal two-dimensional view. User interface screen 4200 of FIG. 42 illustrates the anterior femur, which may be utilized to determine the default size of the femoral component and to also calculate possible notching. In certain embodiments, both the three-dimensional view and the sagittal two-dimensional view may be useful in picking this point. The user may select a point that is on the hard-cortical surface of the anterior femoral shaft along the mechanical axis. In certain embodiments, it may be ensured that the point is above the articular surface and above where the condyles curve onto the anterior shaft.

Figure 43:
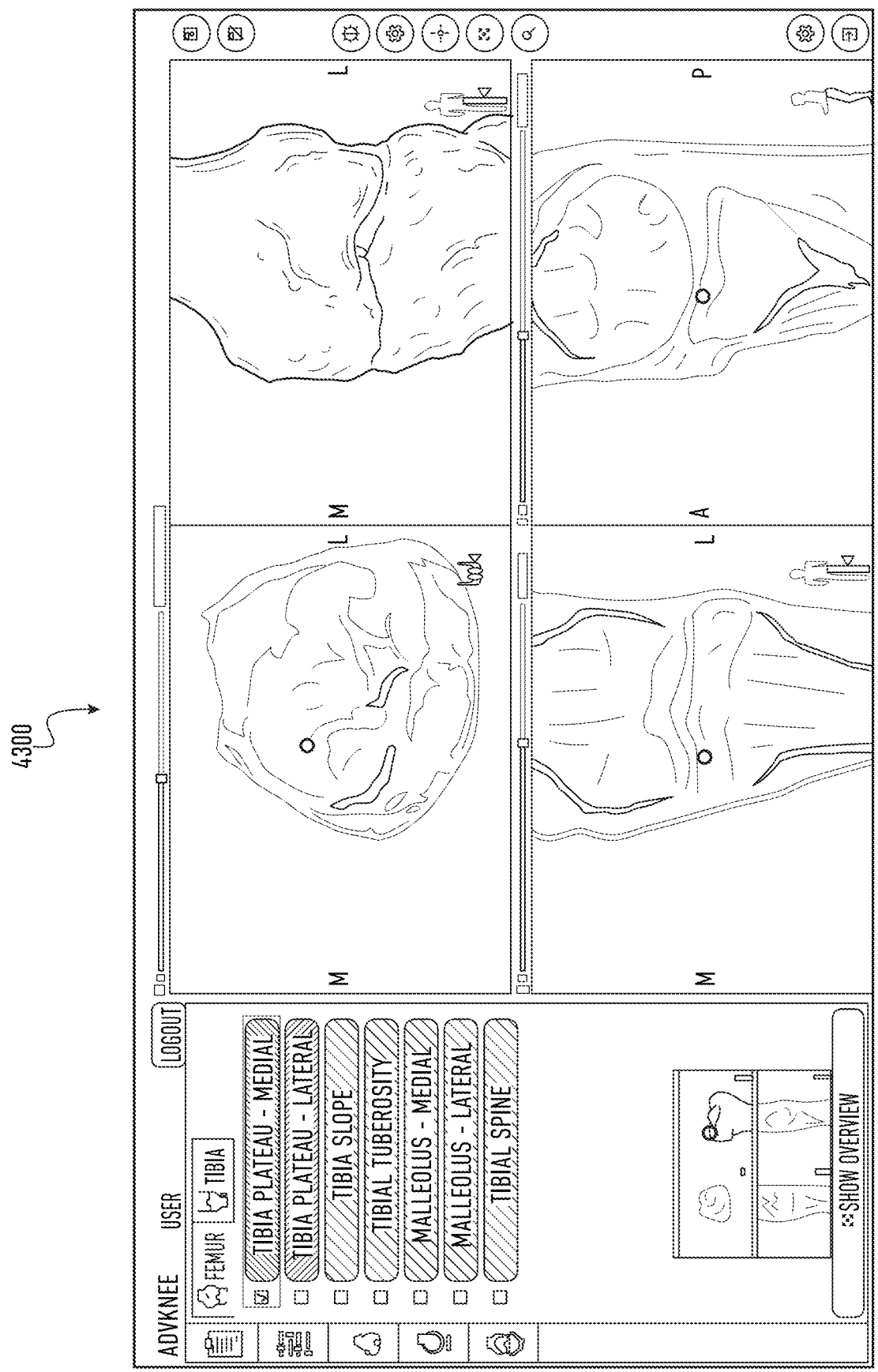
FIG. 43 is a sample user-interface of an application for use with the system of FIG. 1, which facilitates tibial landmarking using tibia plateaus.
Figure 44:
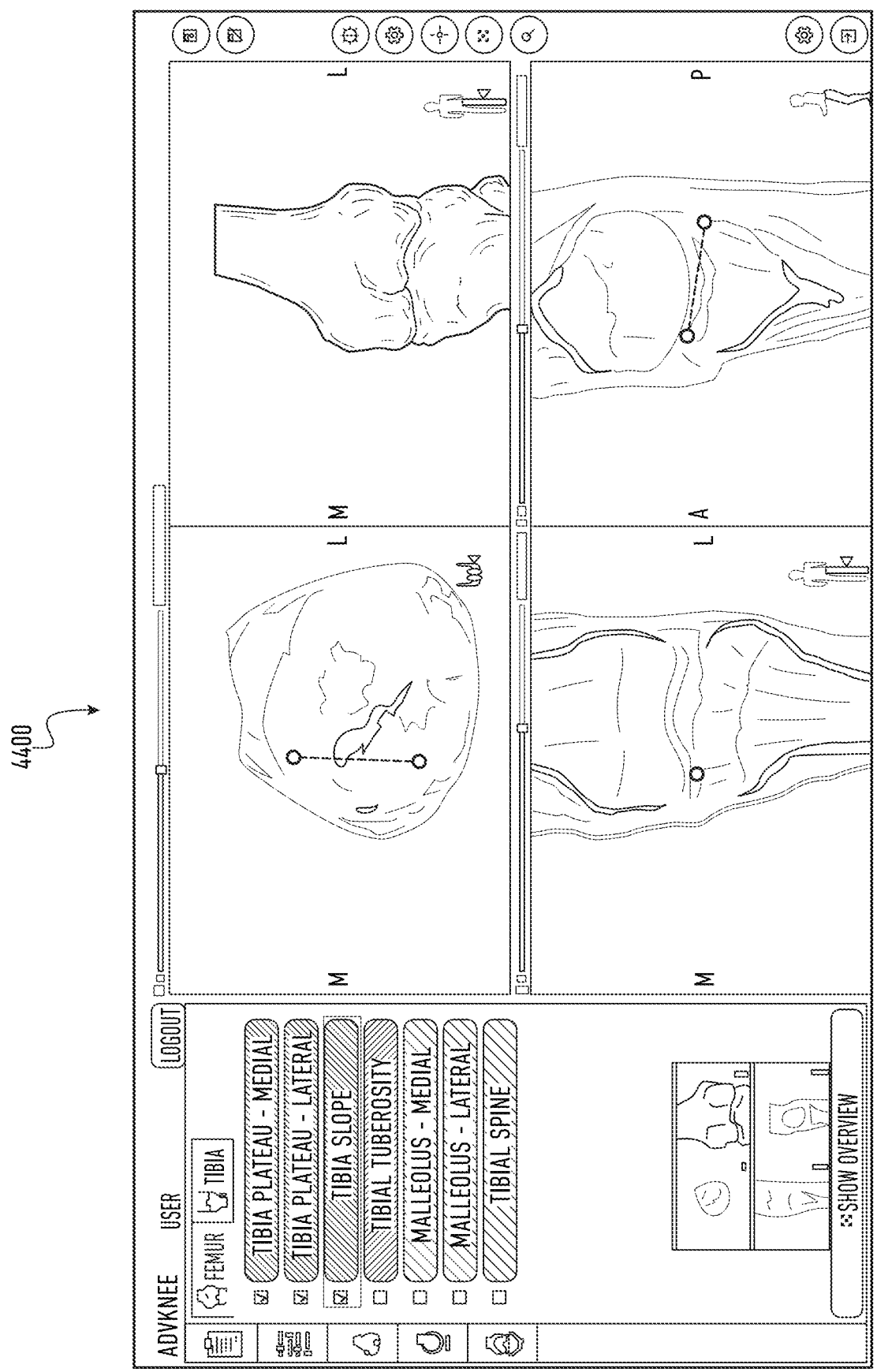
FIG. 44 is a sample user-interface of an application for use with the system of FIG. 1, which facilitates tibial landmarking using a tibia slope.
Figure 45:
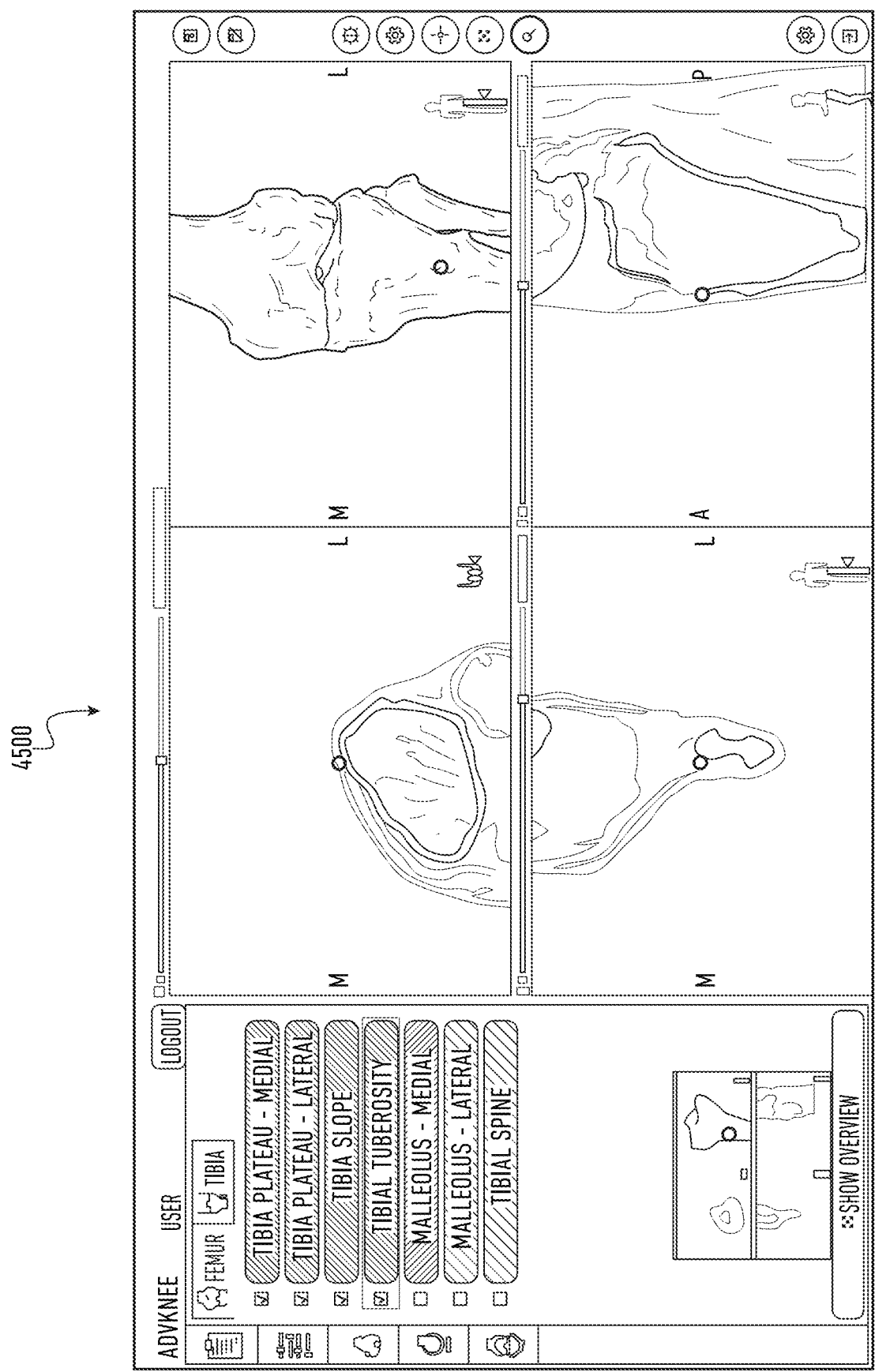
FIG. 45 is a sample user-interface of an application for use with the system of FIG. 1, which facilitates tibial landmarking using tuberosity.
Figure 46:
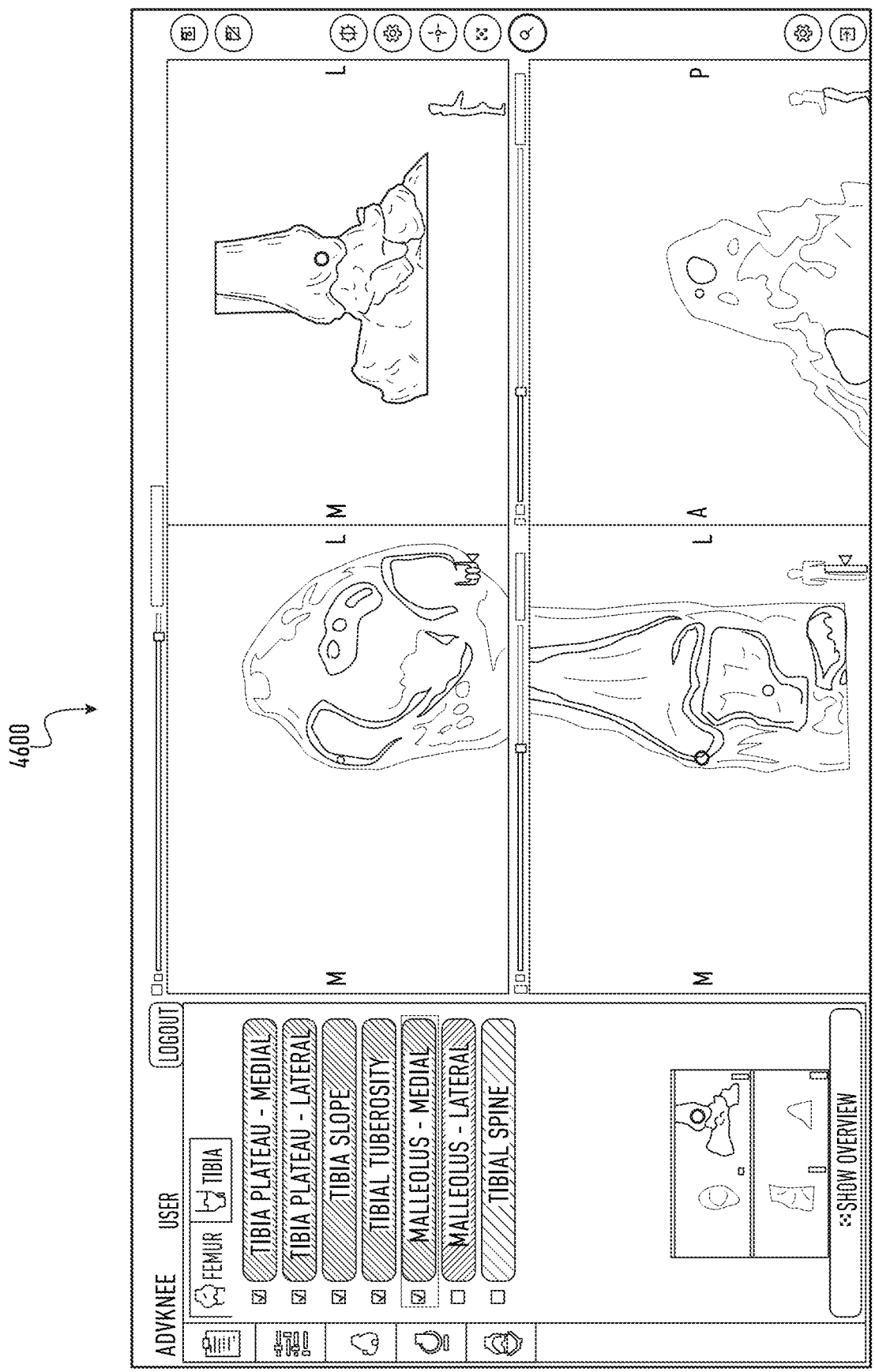
FIG. 46 is a sample user-interface of an application for use with the system of FIG. 1, which facilitates tibial landmarking using malleoli.
Figure 47:
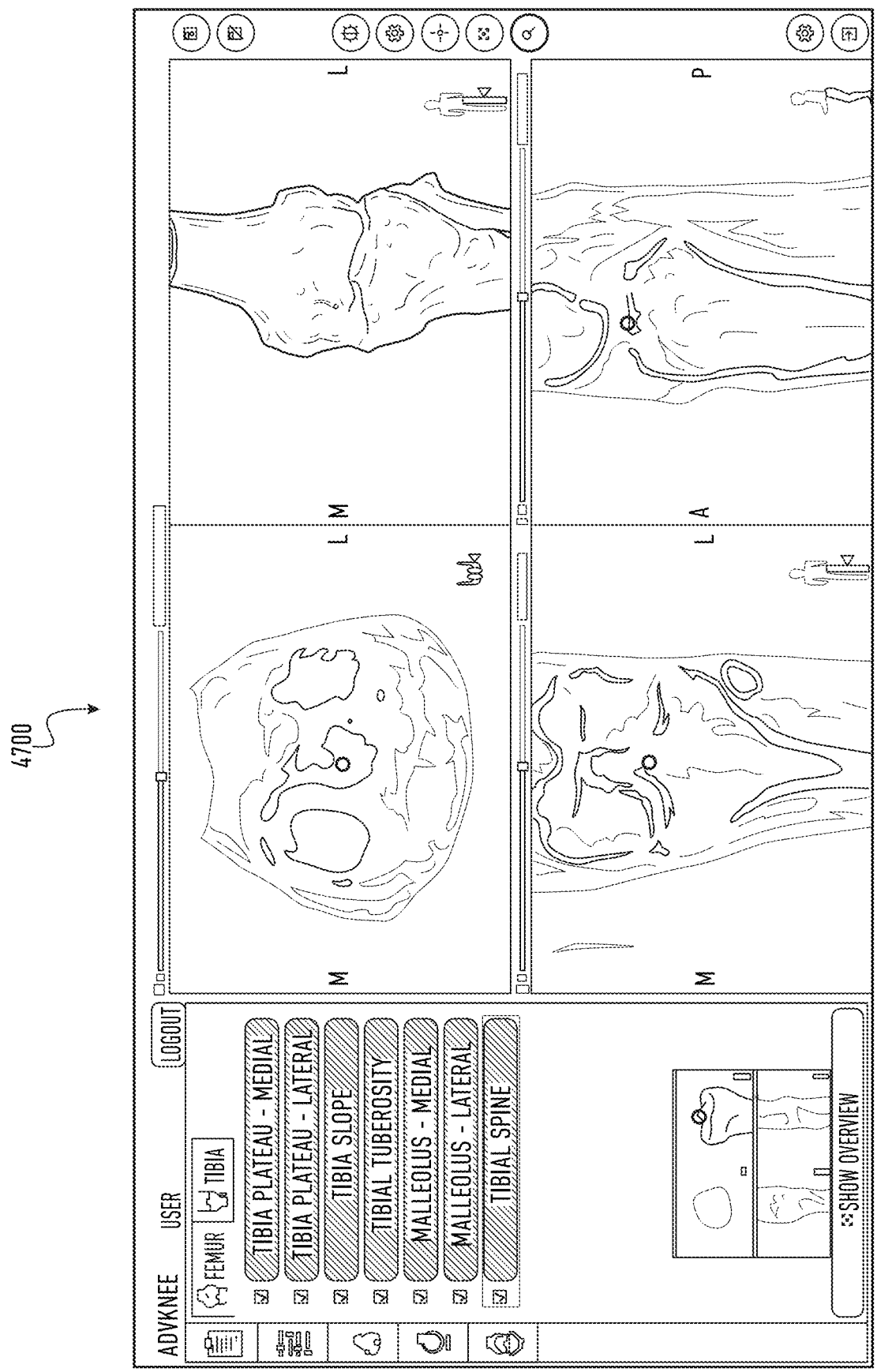
FIG. 47 is a sample user-interface of an application for use with the system of FIG. 1, which facilitates tibial landmarking using a tibial spine.

Referring now also to FIGS. 43-47, user interfaces 4300-4700 for facilitating tibial landmarking using the system 100 are illustrated. In FIG. 43, user interface 4300 illustrates tibial plateaus. In certain embodiments, medial and lateral tibial plateau landmarks may be utilized to calculate the resection depth. The axial and coronal two-dimensional views may be the most useful in selecting the tibial plateau points. For each of the medial and lateral plateaus, the lowest point may be selected. User interface 4400 of FIG. 44 illustrates the tibia slope. The tibial slope may define the pre-operative slope and may be utilized to assist in the default placement of the tibial component of an implant. In certain embodiments, the sagittal two-dimensional image may be most useful in defining the tibial slope. The user may scroll and/or synchronize the sagittal two-dimensional view such that it intersects the middle of the medial plateau. The user may then select the anterior point of the slope on the rim of the anterior plateau and select the posterior point of the slope on the rim of the posterior plateau. User interface 4500 of FIG. 45 illustrates tuberosity. The tuberosity point may be utilized by the system 100 to calculate the anterior/posterior direction of the tibia. The point on the tuberosity may be most easily selected by the user on the three-dimensional image. The user may select (e.g., click) the tibial tuberosity landmark button and select a point on the medial side of the upper third of the tibial tubercle. User interface screen 4600 of FIG. 46 illustrates malleoli that may be utilized in determining the mechanical axis of the tibia. The medial and lateral malleoli may be most easily selected using the three-dimensional view, for example. For each malleolus, the user may click on the landmark button and select the corresponding medial or lateral point in the image. User interface 4700 of FIG. 47 illustrates the tibial spine. The tibial spine may be used, along with the malleoli, to determine the mechanical axis of the tibia, for example. In certain embodiments, the malleoli may be collected by the system 100 before the tuberosity is collected. In certain embodiments, all two-dimensional views may assist in selecting the tibial spine point. In the coronal view, the point may be in the groove of the tibial spine, slightly medial. In the axial view, the point may be just posterior to the ACL insertion, slightly medial. In the sagittal view, the line representing the tibial mechanical axis may be parallel to the posterior cortex.

Figure 48:
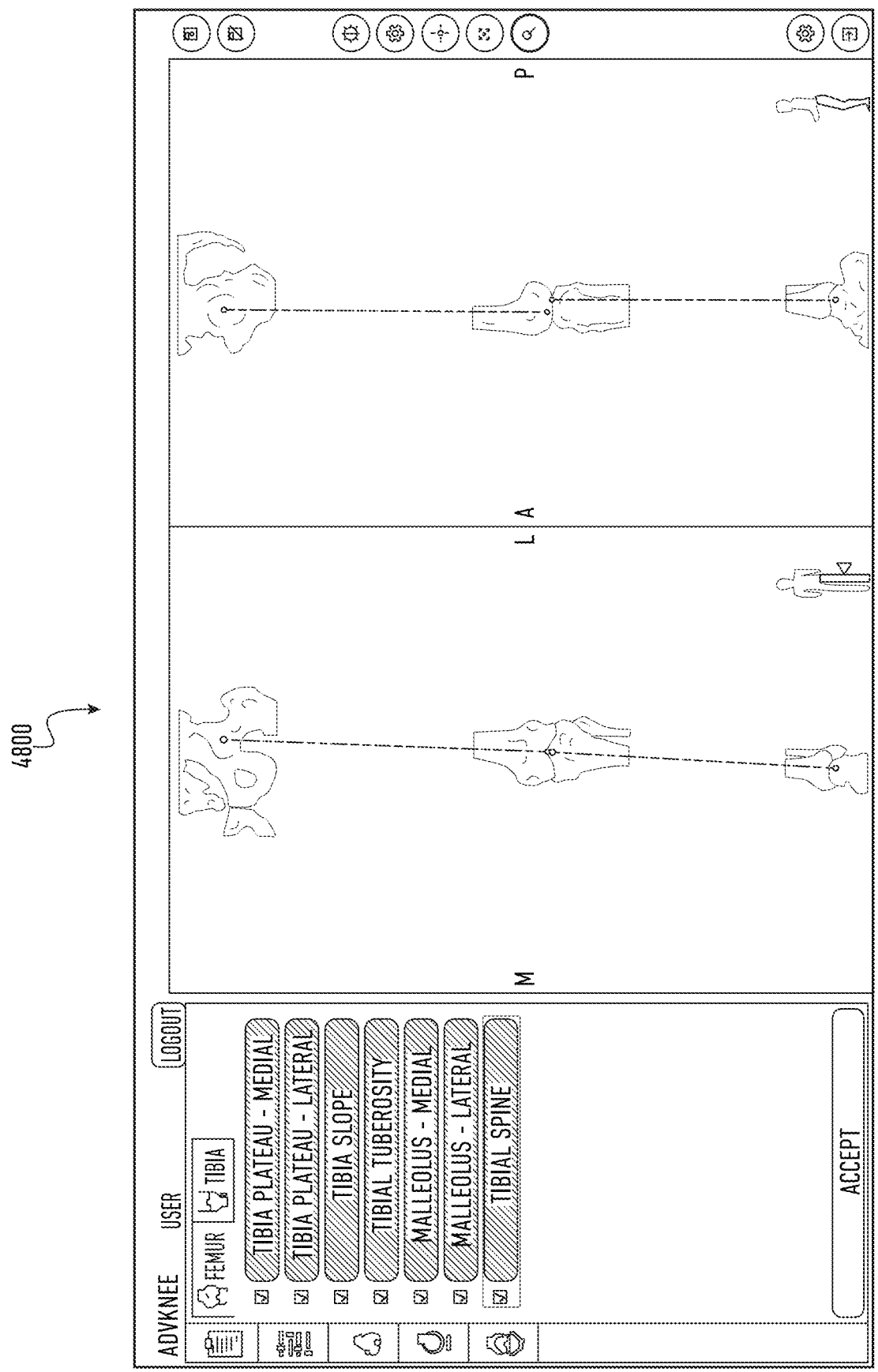
FIG. 48 is a sample user-interface of an application for use with the system of FIG. 1, which provides a limb alignment overview once anatomical landmarks are defined.
Figure 49:
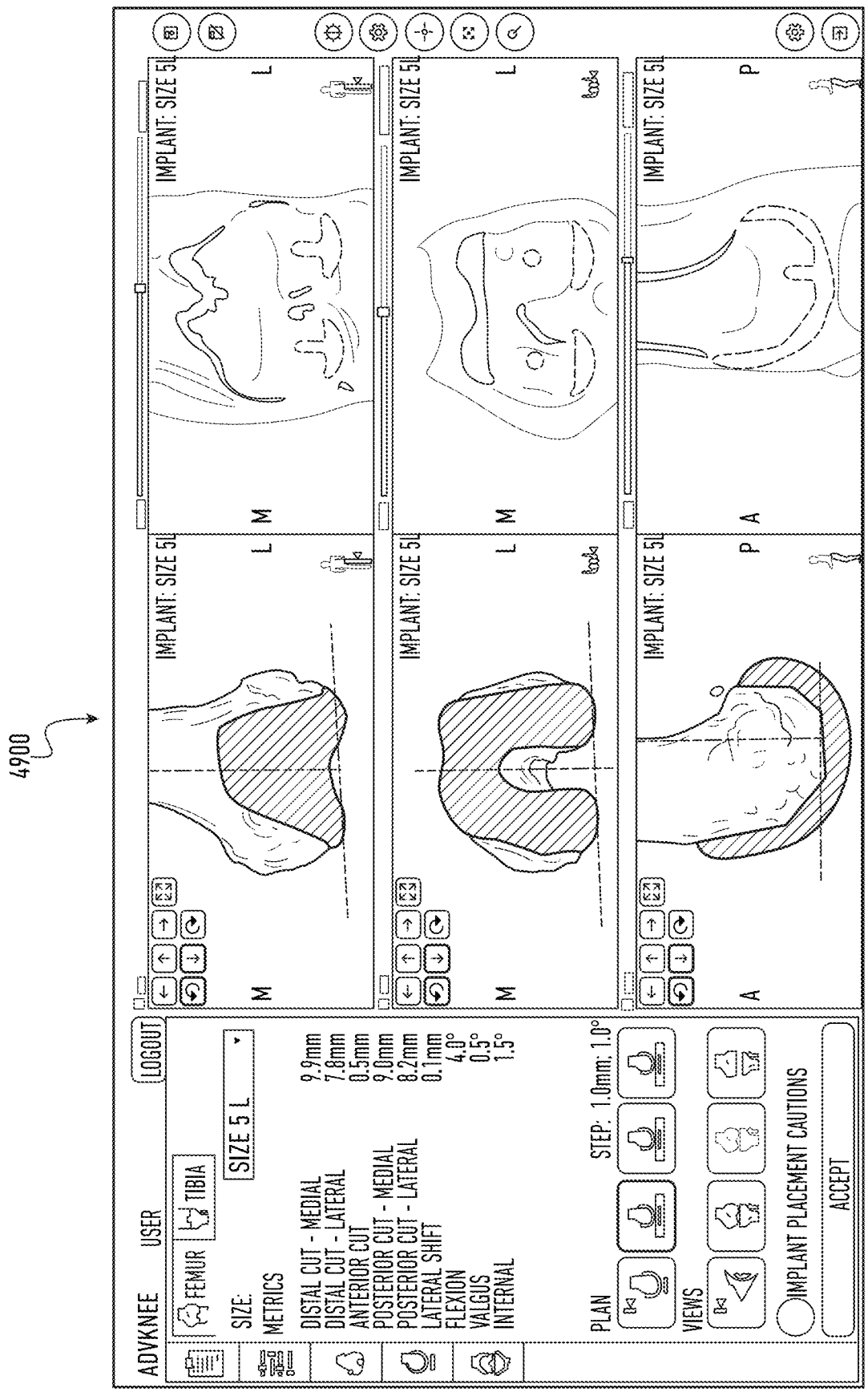
FIG. 49 is a sample user-interface of an application for use with the system of FIG. 1, which facilitates surgical planning.
Figure 50:
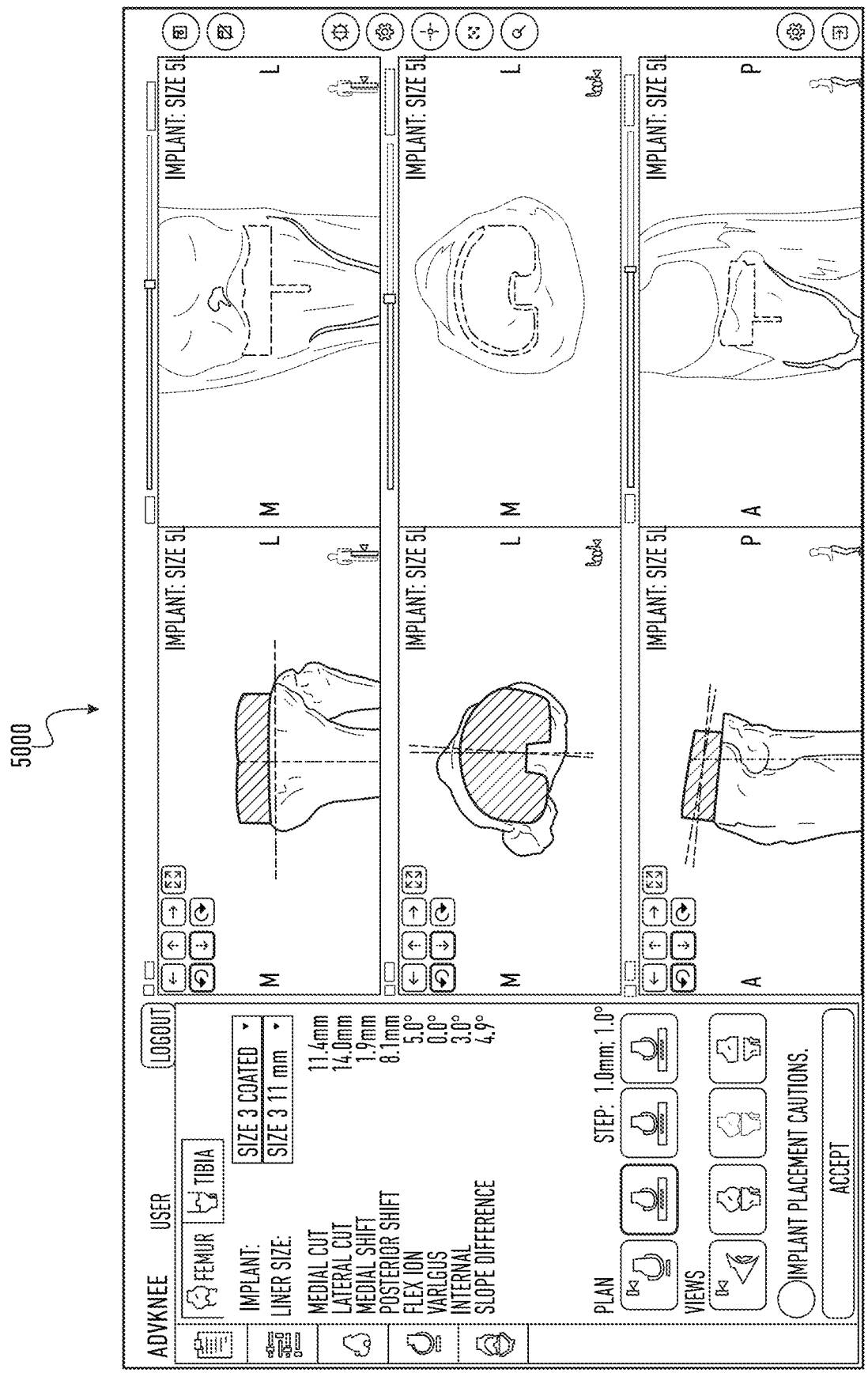
FIG. 50 is a sample user-interface of an application for use with the system of FIG. 1, which facilitates selection of implant positioning for an implant.

Referring now also to FIG. 48, user interface screen 4800 enables the user to view a limb alignment overview for the anatomy of interest of the subject. In certain embodiments, once all landmarks have been defined, the "Show overview" button of the application may be enabled. The user may click the button to go to the limb alignment overview and review the limb axes created from the defined landmarks. This view also enables the user to see the coronal and sagittal alignment of the limb and verify the alignment before clicking the "Accept" button to move on the surgical planning step in the process. Referring now also to FIGS. 49-52, user interfaces for facilitating planning for a surgical procedure are shown. Based on the landmarking conducted, the femoral and tibial components selected in the surgical options step may be placed in default positions. The default placements may depend on the requirements dictated by the implant manufacturer and may be fine-tuned by the user to accommodate patient-specific needs, current best-practices, and surgeon preferences. In FIGS. 49-50, user interfaces 4900 and 5000 facilitate positioning of the implant. The user may utilize the controls rendered in the upper left region of the user interfaces 4900 and 5000 to reposition the implant. As the implant is moved, the metrics that are overlaid on the corresponding images, as well as the tabular metrics, may be updated to reflect the new position. For example, the metrics may be color-coded to show the blue/white as being a metric that is within the surgical specification for the implant, purple may indicate that the metric is approaching the limit of what the manufacturer of the implant recommends, and red may indicate that the metric is outside the expected limits for the implant. The straight arrow controls may be utilized to translate the component in the anatomical directions that correspond to the image's default perspective. For example, the right arrow in the three-dimensional coronal view may move the components to the left in anatomical coordinates (because the coronal view may be from the front of the subject). When the view is in its default perspective, this is also to the right in the image. If the image is rotated, the right arrow may still move the component to the anatomical right, which may no longer be to the right in the image. A control may be provided to reset the implant position. For example, the implant position may be restored to a default position at any time by clicking the "Reset position" button in the control panel. In certain embodiments, controls for adjustments precision may be provided. For example, the "Adjustment precision" buttons may control the amount of translation and rotation that occurs when using the "Positioning" buttons. In certain embodiments, three levels of precision may be provided: (1) Course—1 mm and 1 degree; (2) Medium—0.5 mm and 0.5 degree; and (3) Fine—0.1 mm and 0.1 degree. In certain embodiments, the active precision button may have a yellow (or other color) border and the background may be slightly darker.

Figure 51:
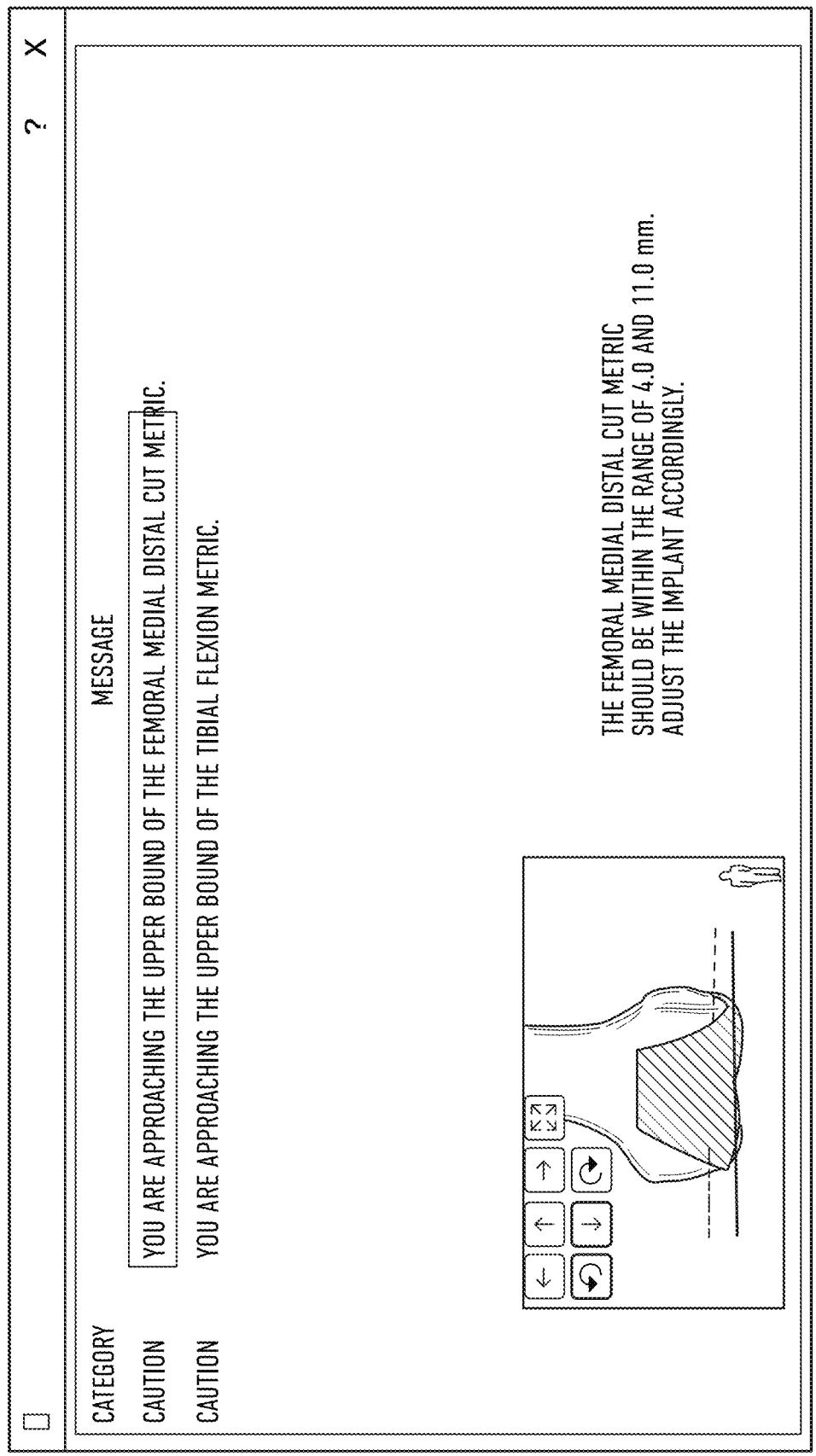
FIG. 51 is a sample user-interface of an application for use with the system of FIG. 1, which provides implant positioning hints and alerts.

In certain embodiments, positioning hints may be provided via the application. For example, FIG. 51 illustrates user interface 5100, which may be utilized to provide such hints. In certain embodiments, if any metrics associated with the surgical plan are in a caution or warning state, the application may provide hints on how to adjust the implant position. Rendered warning icons may be selected by the user to display a dialog listing all the warnings and cautions and associated hints for rectifying such warnings. Such hints may indicate how to adjust the implant position to remove the warning or caution. In certain embodiments, the main portion of the planning step of the surgical planning process may be taken up using six image views including three three-dimensional views and three two-dimensional views. The views may be manipulated to better inspect the implant placement. In certain embodiments, the application may enable manipulation of the three-dimensional views, such as by providing a rotate control. For example, the user may hold a left click with a mouse on any three-dimensional view and drag the image to freely rotate it. The user may also be provided by a zoom control, such as by either (1) pressing and holding the right mouse button and then moving the mouse up or down to zoom out or in; or (2) roll the mouse wheel of the mouse up/down to zoom out or in respectively. In certain embodiments, a move control may also be provided, which may involve pressing and holding the mouse wheel and then dragging to move the image in the direction of the drag. With regard to the two-dimensional views, a zoom control may be provided, which may involve pressing and holding the right mouse button and then moving the mouse up or down to zoom out or in. Similarly, a move control may be provided, which may include pressing and holding the mouse wheel, and dragging to move the image in the direction of the drag. A scroll control may also be provided, which may include either (1) holding the mouse cursor over the image to scroll through, then rotate the mouse wheel up or down; or (2) use the color-coded scroll bar at the top of each two-dimensional image to scroll through the images. In certain embodiments, the six image views may be reset to a default perspective by clicking the "Reset position" button on the task control panel of a user interface of the application. In certain embodiments, individual views may be reset to a default perspective by clicking on a reset icon next to the view label for the particular view.

Figure 52:
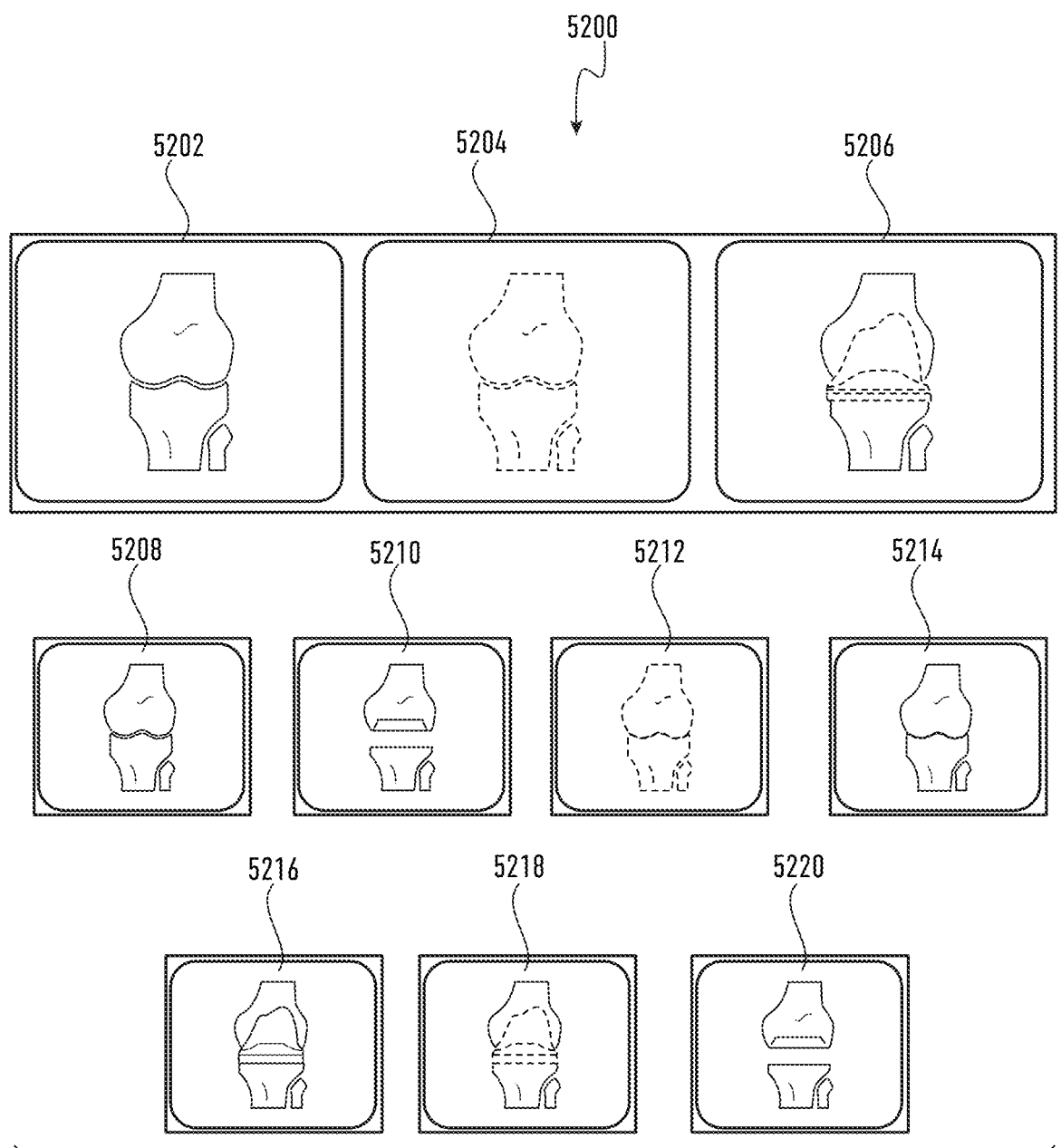
FIG. 52 features an assortment of various controls for adjusting the view of bone cuts and implants.

Referring now also to FIG. 52, a portion of a user interface screen 5200 featuring exemplary controls 5202, 5204, 5206, 5208, 5210, 5212, 5214, 5216, 5218, and 5220 are shown. Bone cuts and implants may be controlled using the view button ribbon including controls 5202, 5204, 5206. Controls 5208 and/or 5210 may be two-state buttons for showing or hiding the bone cuts. Controls 5212 and/or 5214 may be two-state buttons for making the bone rendering transparent or opaque. Controls 5216, 5218, and/or 5220 may be tri-state buttons for making the implant opaque, transparent, or hidden respectively. Notably, at anytime during the planning process, the plan itself can be saved via the application. This may be to pause and resume the planning task later or may be utilized to save different options for implant placement. When entering the planning step after completion of the landmarking step, the femoral planning step described above may be displayed by default. The femoral implant size and position may be selected by default depending on the landmarks that were defined in the landmarking step. In certain embodiments, the user may then use a size-selection dropdown menu and the planning controls to place the femoral component according to the manufacturer recommendations, best practices, and patient-specific needs. When finished placing the femoral component, the user may click on the tibia tab at the top of the control panel to move on to the planning of the tibial component placement and poly thickness. The tibial planning step may have a dropdown menu to select the size for the tibial component and a separate drop down menu to select the thickness of the poly to use. The user may use a size selection drop down menu and planning controls to place the tibial component according to the manufacturer recommendations, best practices, and/or patient-specific needs. When the user is satisfied with the placement of the implant, the user may click on the "Accept" button to move to the "Verify plan" step of the process. The plan may then be saved for later review and verification by the operation surgeon.

Figure 53:
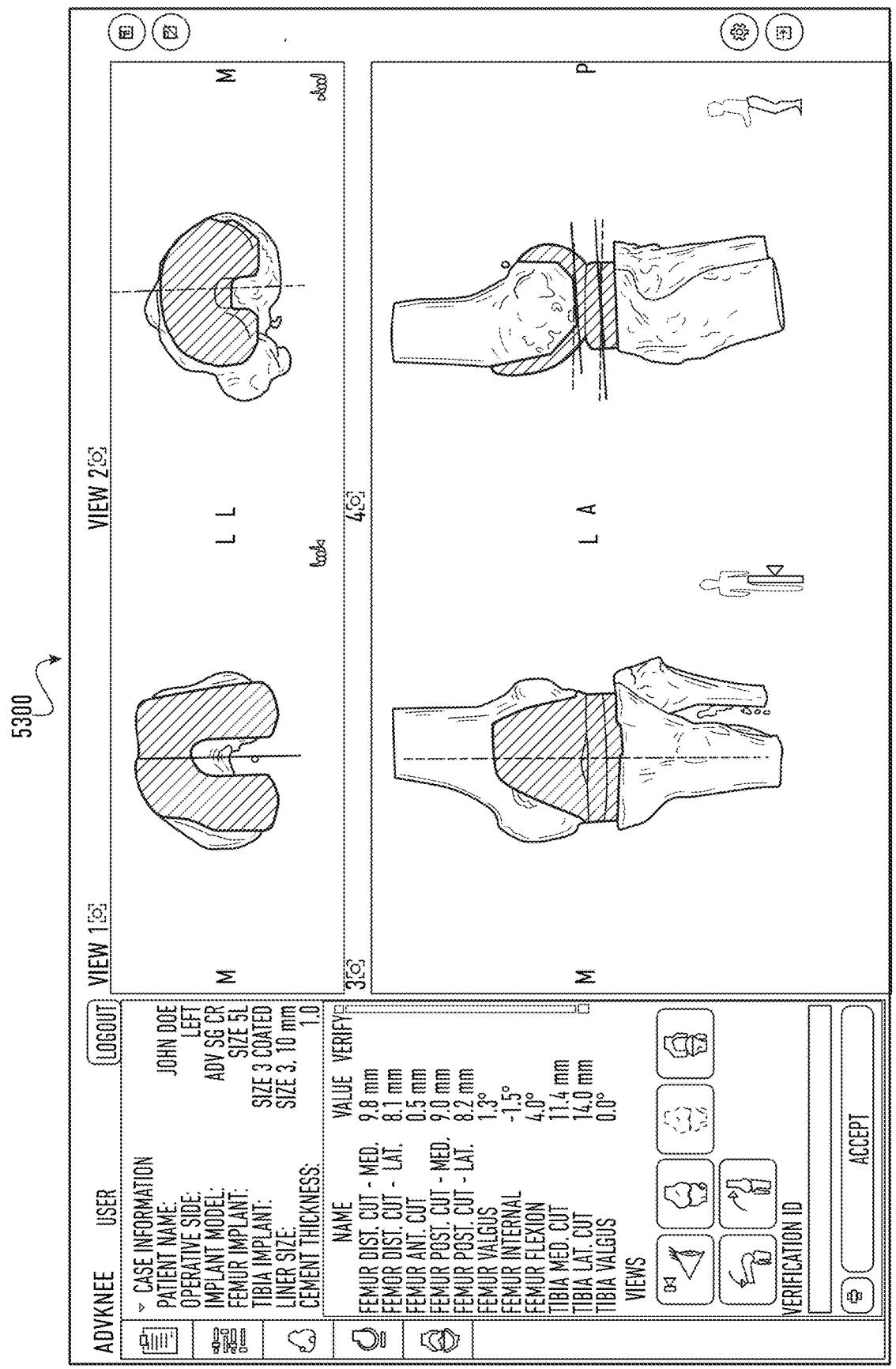
FIG. 53 is a sample user-interface of an application for use with the system of FIG. 1, which facilitates verification the planned implant placement for an implant to be implanted onto a subject.

Referring now also to FIG. 53, a user interface 5300 is shown, which facilitates the surgical plan verification portion of the process. The verify step may allow the operating surgeon to review and approve the planned implant placement. The verification step may provide three-dimensional views in a 4-up layout with key metrics overlaying the images. A complete list of all metrics may be found to the left of the images in tabular form. A summary of the plan may be printed for record keeping or for sharing purposes. The operating surgeon may use his or her assigned verification identifier to approve the plan and prepare it for use with a surgical navigation and/or robotic system. In certain embodiments, a portion of the user interface 5300 may consist of four three-dimensional views of the planned implant position with key metrics overlayed on the images. The images may be interacted within in the same manner and using the same or similar techniques as with the three-dimensional images in the planning step of the process. In certain embodiments, the user may click on the "Flexion" or "Extension" button of the user interface 5300 to view the implant in the corresponding orientations. This may be useful for the user to view changes in the gap between the two positions. The relative size of the two upper views and the two lower views may be changed by dragging the horizontal sizing control in the center of the four three-dimensional views up or down. In certain embodiments, the printing report control may be utilized to print records or for potentially sharing the surgical plan or a summary of the plan. The "Print" button may open the system print dialog. In addition to printing a paper summary, the system 100 may use the print dialog to send the summary to a PDF file for electronic filing or sharing as well. Once the surgical plan is reviewed, the operating surgeon may enter his or her personal verification identifier and accept the plan for use in navigation or robotic-assisted intervention. In there are outstanding cautions and/or warnings, then each of these may need to be accepted by the operating surgeon, such as by checking the digital box next to the metric in a caution or warning state before verification of the plan is enabled by the system 100.

Referring now also to FIG. 54, a portion of a user interface screen 5400 is shown, which features various controls for use with the system 100, such as during the surgical plan generation phase of the process. Such controls may include, but are not limited to, a save control (e.g. save the current plan and overwrite the previous plan), a save as control (e.g. saves the current plan to a new file), a windowing control (e.g. allows using the mouse to adjust contrast and brightness), an auto windowing control (e.g. automatically choses a contrast and brightness for images), a slice intersection control (e.g. shows orthogonal images as color-coordinated slice intersections), a sync slices control (e.g. synchronizes two-dimensional image views if the mouse is moved while the left button is pressed), a zoom with mouse wheel control (e.g. the mouse wheel will zoom two-dimensional images (normally the mouse will scroll two-dimensional images)), a preferences control (e.g. opens dialog for application and surgeon preferences), and an exit control (e.g. exits the application and prompts saving of the surgical plan if changes to the plan have been made).

Notably, as shown in FIG. 1, the system 100 may perform any of the operative functions disclosed herein by utilizing the processing capabilities of server 160, the storage capacity of the database 155, or any other component of the system 100 to perform the operative functions disclosed herein. The server 160 may include one or more processors 162 that may be configured to process any of the various functions of the system 100. The processors 162 may be software, hardware, or a combination of hardware and software. Additionally, the server 160 may also include a memory 161, which stores instructions that the processors 162 may execute to perform various operations of the system 100. For example, the server 160 may assist in processing loads handled by the various devices in the system 100, such as, but not limited to, obtaining images (or other media content) of an anatomy of interest of a subject (e.g. second user 110), rendering enhanced versions of the images via volume rendering; generating plans for implanting an implant onto the anatomy of interest; enabling implant positioning to be conducted for the plan; enabling selection of implant positions for the implant; conducting registration processes to match the anatomy of interest with the information contained in the enhanced version of the image of the anatomy of interest; re-attempting and/or refining registration processes; facilitating performance of a surgical procedure for implanting the implant onto the anatomy of interest of the subject; and performing any other suitable operations conducted in the system 100 or otherwise. In one embodiment, multiple servers 160 may be utilized to process the functions of the system 100. The server 160 and other devices in the system 100, may utilize the database 155 for storing data about the devices in the system 100 or any other information that is associated with the system 100. In one embodiment, multiple databases 155 may be utilized to store data in the system 100.

Although FIGS. 1-56 illustrates specific example configurations of the various components of the system 100, the system 100 may include any configuration of the components, which may include using a greater or lesser number of the components. For example, the system 100 is illustratively shown as including a first user device 102, a second user device 111, a communications network 135, a server 140, a server 145, a server 150, a server 160, and a database 155. However, the system 100 may include multiple first user devices 102, multiple second user devices 111, multiple communications networks 135, multiple servers 140, multiple servers 145, multiple servers 150, multiple servers 160, multiple databases 155, or any number of any of the other components inside or outside the system 100. Notably, any number of subcomponents (e.g. processors, memories, interfaces, etc.) of the components may be utilized as well. Furthermore, in certain embodiments, substantial portions of the functionality and operations of the system 100 may be performed by other networks and systems that may be connected to system 100.

Figure 55:
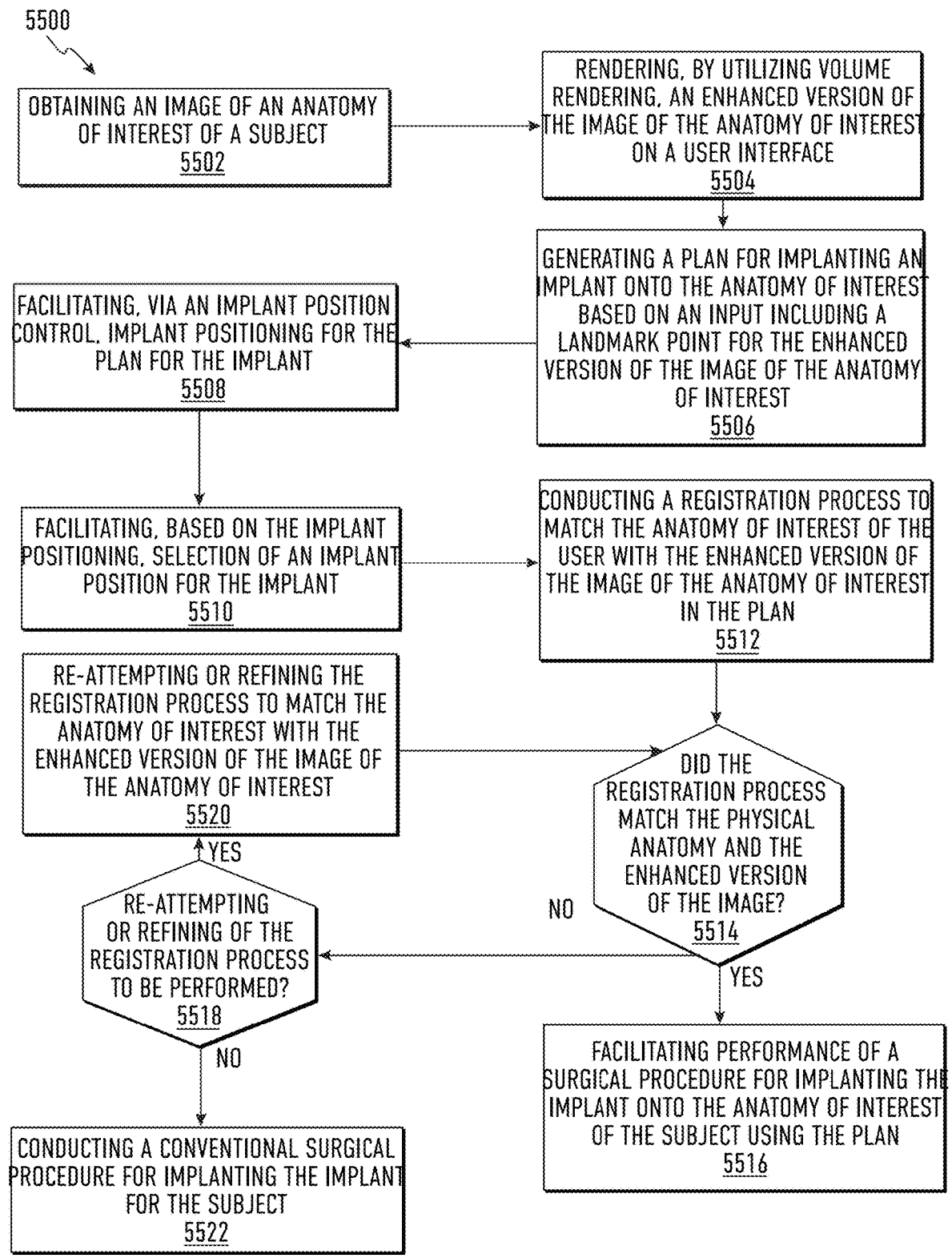
FIG. 55 is a flow diagram illustrating a sample method for providing surgical planning and guidance with three-dimensional visualization according to an embodiment of the present disclosure.

Notably, the system 100 may execute and/or conduct the functionality as described in the method(s) that follow. As shown in FIG. 55, an exemplary method 5500 for providing surgical planning and guidance with three-dimensional visualization is schematically illustrated. The method 5500 and/or functionality and features supporting the method 5500 may be conducted via an application of the system 100, devices of the system 100, processes of the system 100, any component of the system 100, or a combination thereof. The method 3000 may include steps for enhancing imagery and/or other content taken of a subject's anatomy (e.g. second user 110) to facilitate more effective, efficient, and successful performance of surgical procedures. At step 5502, the method 5500 may include obtaining one or more images (and/or media content) of an anatomy of interest of a subject, such as second user 110. The anatomy of interest may be any part of the body of the subject. For example, the anatomy of interest may be a knee, a leg, a thigh, a pelvis, a rib cage, a back, a shoulder, a neck, a head, a foot, a toe, any type of anatomy, or a combination thereof. For the purposes of this method 5500, the anatomy of interest may be a knee of the subject that requires an implant. The images and/or media content of the anatomy of interest (e.g. the subject's knee) may be taken by a CT device, an MRI machine, an X-ray device, a camera, a sensor, any type of imaging device, any type of media device, or combination thereof. The images and/or media content may include two-dimensional (2D) content, 3D content, video content, audio content, augmented reality content, virtual reality content, any type of image content, any type of media content, or a combination thereof. In certain embodiments, the obtaining of the image (and/or media content) may be performed and/or facilitated by the first user 101, the second user 110 and/or by utilizing the first user device 102, the second user device 111, the server 140, the server 145, the server 150, the server 160, the communications network 135, any combination thereof, or by utilizing any other appropriate program, network, system, or device.

Once the images (and/or media content) of the anatomy of interest are obtained, the method 5500 may proceed to step 5504. At step 5504, the method 5500 may include rendering, by utilizing volume rendering, an enhanced version of the image(s) (and/or media content) of the anatomy of interest on a user interface. In certain embodiments, the volume rendering may be any suitable type of volume rendering technique including, but not limited to, volume rendering techniques as described in "Principles of visualization in radiation oncology. Oncology." 2020; 98(6):83-93. Schlachter M, Preim B, Baler K, Raidou RG. In certain embodiments, the volume rendering may include utilizing techniques used to display two-dimensional (2D) projections of 3D images sets of the anatomy of interest. In certain embodiments, the rendering of the enhanced version of the image by utilizing volume rendering may be performed and/or facilitated by the first user 101, the second user 110 and/or by utilizing the first user device 102, the second user device 111, the server 140, the server 145, the server 150, the server 160, the communications network 135, any combination thereof, or by utilizing any other appropriate program, network, system, or device. At step 5506, the method 5500 may include generating a plan for implanting an implant onto the anatomy of interest based on one or more inputs, such as an input including a landmark point for the enhanced version of the image (and/or media content) of the anatomy of interest. In certain embodiments, the landmark point(s) may be utilized to facilitate measurement of distances and angles between the anatomy and the implant to be implanted onto the anatomy. In certain embodiments, the implant itself may be customized in shape and/or size based on the landmark point(s) in the image(s). In certain embodiments, the inputs may also include the implant type of the implant to be implanted, the type of approach to be utilized for implantation, information associated with the sides of the anatomy and/or implant itself, bone density information, bone size information, bone surface information, information associated with the subject, any other information, any other type of input, or a combination thereof. In certain embodiments, the generating of the plan may be performed and/or facilitated by the first user 101, the second user 110 and/or by utilizing the first user device 102, the second user device 111, the server 140, the server 145, the server 150, the server 160, the communications network 135, any combination thereof, or by utilizing any other appropriate program, network, system, or device.

At step 5508, the method 5500 may include facilitating, via one or more implant position controls, implant positioning for the plan for the implant. In certain embodiments, the implant position controls for positioning the implant may be visually rendered such that the implant position controls are rendered in proximity to the subject interface views where the volume rendering of the subject's bones are displayed. The surgeon (and/or device and/or program) may utilize the implant position controls to adjust the position of the implant with respect to the anatomy of interest for the plan. Each time the position of the implant is adjusted by a surgeon (or device), the system and methods may update the corresponding bone cuts of the anatomy of the subject and visualize the updated bone cuts in real-time using volume rendering. In certain embodiments, the position of the implant may be adjusted by using finger inputs via a touchscreen user interface of the first and/or second user devices 102, 111, using an electronic mouse, using a keyboard, using speech commands, using any type of input technology, or a combination thereof. In certain embodiments, the system and methods may calculate measurements related to the implant pose each time the implant positions are adjusted. The measurements related to the implant pose may be blended and displayed with volume rendering to assist the surgeon (or device) during selection of the optimal implant positions for the implant. In certain embodiments, implant positioning may be performed and/or facilitated by the first user 101, the second user 110 and/or by utilizing the first user device 102, the second user device 111, the server 140, the server 145, the server 150, the server 160, the communications network 135, any combination thereof, or by utilizing any other appropriate program, network, system, or device.

At step 5510, the method 5500 may include facilitating, based on the implant positioning, selection of an implant position(s) for the implant, such as with respect to the anatomy of the subject. In certain embodiments, the implant position(s) may be positions that correspond and/or correlate with optimal implant position(s) that are indicative of a higher surgical outcome success rate than other implant positions. The implant position(s) may be selected via a user interface of a program displayed on a device, such as first and/or second user devices 102, 111. In certain embodiments, the selection of the implant position(s) may be performed and/or facilitated by the first user 101, the second user 110 and/or by utilizing the first user device 102, the second user device 111, the server 140, the server 145, the server 150, the server 160, the communications network 135, any combination thereof, or by utilizing any other appropriate program, network, system, or device. Once the desired implant positions are selected, the method 5500 may save the implant positions relative to the accepted landmark point(s) in the plan for the subject. In certain embodiments, steps 5508 and 5510 may be combined together into a single step. At step 5512, the method 5500 may include conducting a registration process to match the anatomy of interest of the subject with the enhanced version of the image (or image set and/or media content) of the anatomy of interest in the plan. During the registration process, the system 100 may determine the actual position(s) of the subject's anatomy (bones), such as, for example, when the subject is surgically opened up and the anatomy of interest is exposed. In certain embodiments, portions of the subject's anatomy may be localized using tracked pointers, surface scanner devices, and/or other technologies and/or methodologies. Once the information is collected of the subject's actual bone position(s), a registration algorithm of the system 100 may match the data from the actual position(s) with the corresponding bone information from the enhanced version of the image (or image set and/or media content) so as to establish the spatial relationship(s) between the subject's anatomy and the information contained in the enhanced version of the image(s). In certain embodiments, the registration algorithm of the system 100 may match the anatomy of interest with the enhanced version of the image (or image set and/or media content) by matching a coordinate reference between the anatomy and the enhanced version of the image, matching one or more anatomical landmark points between the anatomy and the enhanced version of the image, or a combination thereof. Notably, in certain embodiments, the method 5500 conducts the registration process without requiring bone contouring and/or the use of a digital surface model, which often involve time-consuming and/or labor-intensive processes to accomplish. In certain embodiments, the registration process may be performed and/or facilitated by the first user 101, the second user 110 and/or by utilizing the first user device 102, the second user device 111, the server 140, the server 145, the server 150, the server 160, the communications network 135, any combination thereof, or by utilizing any other appropriate program, network, system, or device.

At step 5514, the method 5500 may include determining whether the registration process matched the physical anatomy of the subject with the information in the enhanced version of the image(s) (and/or image set and/or media content). If the registration process successfully matches the physical anatomy of the subject with the information associated with the anatomy contained in enhanced version of the image(s) in the plan, the method 5500 may proceed to step 5516. At step 5516, the method 5500 may include facilitating performance of a surgical procedure for implanting the implant onto the anatomy of interest of the subject using the plan. For example, the system 100 may, with the surgeon, utilize the plan to enable the surgeon to perform the implant surgery on the subject. In certain embodiments, the plan may be utilized in conjunction with a surgical navigation system and/or other computing system to facilitate performance of the surgery. In certain embodiments, the performing of the surgical procedure may be performed and/or facilitated by the first user 101, the second user 110 and/or by utilizing the first user device 102, the second user device 111, the server 140, the server 145, the server 150, the server 160, the communications network 135, any combination thereof, or by utilizing any other appropriate program, network, system, or device.

If, however, at step 5514, registration process does not effectively match the physical anatomy of the subject with the information associated with the anatomy contained in enhanced version of the image(s) in the plan, the method 5500 may proceed to step 5518. At step 5518, the method 5500 may include determining whether re-attempting or refining of the registration process is to be performed. If re-attempting or refining of the registration process is to be performed, the method 5500 may proceed to step 5520, which may include re-attempting or refining the registration process to match the anatomy of interest with the information in the enhanced version of the image(s) (or image set and/or media content) of the anatomy of interest. In certain embodiments, the re-attempting and/or refining of the registration process may be performed and/or facilitated by the first user 101, the second user 110 and/or by utilizing the first user device 102, the second user device 111, the server 140, the server 145, the server 150, the server 160, the communications network 135, any combination thereof, or by utilizing any other appropriate program, network, system, or device. Once the re-attempting and/or refining are performed, the method 5500 may proceed back to step 5514 and may continue with the subsequent steps of the method 5500 accordingly. If, however, at step 5518, the re-attempting and/or refining is not to be performed, the method 5500 may proceed to step 5522. At step 5522, the method 5500 may include having the surgeon (or device or system) proceed to conduct a conventional surgical procedure for implanting the implant onto the anatomy of the subject. In certain embodiments, the conventional surgical procedure may be conducted on the subject without using the plan. Notably, the method 5500 may further incorporate any of the features and functionality described for the system 100, any other method disclosed herein, or as otherwise described herein.

The systems and methods disclosed herein may include additional functionality and features. In certain embodiments, the system 100 may be utilized to automatically suggest anatomical landmark points in the image sets (and/or other media content) of the anatomy based on the proportions of the scanned image(s). In certain embodiments, the first points may be suggested based on the original image extent. For example, in the case of a knee implant, the knee joint is near the center of the image, while the hip joint is near the top and the ankle is near the bottom of the entire scan. After the first few landmarks are defined via the system 100, the automatic point suggestions may be refined and updated for subsequent landmark points. For example, when the hip and knee joint position is confirmed by the user (e.g. the surgeon), the ankle point may be more accurately determined using population-based statistics of leg length. Automatic landmark suggestions may also be performed using artificial intelligence and/or machine learning systems. As an example, the system may utilize convolutional neural networks that may be trained for prediction of points using already marked scans as training data. The input for such convolutional neural networks may be the image set of the anatomy of interest with normalized size and intensity, while the output may contain locations of anatomical landmarks. In certain embodiments, other types of neural networks may be utilized, such as, but not limited to, a modular neural network, a recurrent neural network, a self-organizing neural network, a radial basis function neural network, a feedforward neural network, other neural network, or a combination thereof. In certain embodiments, deep learning algorithms may optimize the neural network to predict the landmark positions based only on the preoperative scans. These predictions may be shown to the user (i.e. the surgeon) as suggestions and for automatic positioning of the image views in the planning software user interface for convenience and faster operation of the planning software.

Additionally, the volume rendering utilized by the system 100 and methods is superior to bone contouring for reasons in addition to speed and fewer user interactions required. Specifically, bone contouring only defines the outer surface of perceived bones in the image sets, while information on the internal structure of the bone is lost. In contrast, volume rendering utilized by the system 100 and methods may assign a scale of visible colors (e.g. a continuous scale or other desired scale) and opacity to various bone density in the image sets. When the planned implant model generated via the plan is observed in the context of volume rendering, the position may be optimized not only based on bone surface geometry, but also based on maximum support by dense bone contact with the implant. This may lead to more stable and longer lasting implants.

Furthermore, the system 100 and methods may initially register the surgical plan to the physical bones of the subject using landmark points defined in the image sets. The registration may undergo automatic refinement after initial point-based registration. During automatic refinement, dense bone surfaces may be automatically extracted from the input image and they may be positioned to best match the physical bone surfaces detected by tracing a tracked pointer on the subject's bones or scanned by optical or ultrasonic surface detection devices. The registered plan positions may then be used by surgical navigation systems and surgical robotic systems to guide cutting the bones and accurately positioning the implant components.

Moreover, the system 100 and methods may also incorporate the use of morphing to facilitate the operative functionality of the system 100 and methods. For example, in certain embodiments, the system 100 and methods may utilize morphing based on key anatomical points and/or conduct matching to an atlas (e.g., such as in the context of an imageless modality utilized by the system 100 and methods to provide the functionality described in the present disclosure). In certain embodiments, after defining anatomical landmark points for a specific anatomy of interest, the system 100 and methods may morph, for example, a general femur model and generic tibia model (or other model(s)) to the input image (or other content) based on the anatomical landmark points. In certain embodiments, the input image may be masked based on the morphed bone models to create a separate image for the femur and another image for the tibia. This allows the system 100 and methods to separately register and visualize these bones, which may further enhance the functionality of the system 100 and methods. For example, the system 100 and methods may allow for visualization of a femoral implant relative to a femur image and the tibial implant relative to the tibia image.

The systems and methods disclosed herein may include still further functionality and features. For example, the operative functions of the system 100 and method may be configured to execute on a special-purpose processor specifically configured to carry out the operations provided by the system 100 and method. Notably, the operative features and functionality provided by the system 100 and method may increase the efficiency of computing devices that are being utilized to facilitate the functionality provided by the system 100 and the various methods discloses herein. For example, by training the system 100 over time based on data and/or other information provided and/or generated in the system 100, a reduced amount of computer operations may need to be performed by the devices in the system 100 using the processors and memories of the system 100 than compared to traditional methodologies. In such a context, less processing power needs to be utilized because the processors and memories do not need to be dedicated for processing. As a result, there are substantial savings in the usage of computer resources by utilizing the software, techniques, and algorithms provided in the present disclosure. In certain embodiments, various operative functionality of the system 100 may be configured to execute on one or more graphics processors and/or application specific integrated processors.

Notably, in certain embodiments, various functions and features of the system 100 and methods may operate without any human intervention and may be conducted entirely by computing devices. In certain embodiments, for example, numerous computing devices may interact with devices of the system 100 to provide the functionality supported by the system 100. Additionally, in certain embodiments, the computing devices of the system 100 may operate continuously and without human intervention to reduce the possibility of errors being introduced into the system 100. In certain embodiments, the system 100 and methods may also provide effective computing resource management by utilizing the features and functions described in the present disclosure. For example, in certain embodiments, devices in the system 100 may transmit signals indicating that only a specific quantity of computer processor resources (e.g. processor clock cycles, processor speed, etc.) may be devoted to utilizing the volume rendering, generating the surgical plan for the subject, conducting the registration process, and/or performing any other operation conducted by the system 100, or any combination thereof. For example, the signal may indicate a number of processor cycles of a processor may be utilized to enhance an image set via volume rendering, and/or specify a selected amount of processing power that may be dedicated to generating or any of the operations performed by the system 100. In certain embodiments, a signal indicating the specific amount of computer processor resources or computer memory resources to be utilized for performing an operation of the system 100 may be transmitted from the first and/or second user devices 102, 111 to the various components of the system 100.

In certain embodiments, any device in the system 100 may transmit a signal to a memory device to cause the memory device to only dedicate a selected amount of memory resources to the various operations of the system 100. In certain embodiments, the system 100 and methods may also include transmitting signals to processors and memories to only perform the operative functions of the system 100 and methods at time periods when usage of processing resources and/or memory resources in the system 100 is at a selected value. In certain embodiments, the system 100 and methods may include transmitting signals to the memory devices utilized in the system 100, which indicate which specific sections of the memory should be utilized to store any of the data utilized or generated by the system 100. Notably, the signals transmitted to the processors and memories may be utilized to optimize the usage of computing resources while executing the operations conducted by the system 100. As a result, such functionality provides substantial operational efficiencies and improvements over existing technologies.

Referring now also to FIG. 56, at least a portion of the methodologies and techniques described with respect to the exemplary embodiments of the system 100 can incorporate a machine, such as, but not limited to, computer system 5600, or other computing device within which a set of instructions, when executed, may cause the machine to perform any one or more of the methodologies or functions discussed above. The machine may be configured to facilitate various operations conducted by the system 100. For example, the machine may be configured to, but is not limited to, assist the system 100 by providing processing power to assist with processing loads experienced in the system 100, by providing storage capacity for storing instructions or data traversing the system 100, or by assisting with any other operations conducted by or within the system 100. As another example, the computer system 5600 may assist with enhancing an image set taken of an anatomy of interest by conducting volume rendering.

In some embodiments, the machine may operate as a standalone device. In some embodiments, the machine may be connected (e.g., using communications network 135, another network, or a combination thereof) to and assist with operations performed by other machines and systems, such as, but not limited to, the first user device 102, the second user device 111, the server 140, the server 145, the server 150, the database 155, the server 160, any other system, program, and/or device, or any combination thereof. The machine may be connected with any component in the system 100. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 5600 may include a processor 5602 (e.g., a central processing unit (CPU), a graphics processing unit (GPU, or both), a main memory 5604 and a static memory 5606, which communicate with each other via a bus 5608. The computer system 5600 may further include a video display unit 5610, which may be, but is not limited to, a liquid crystal display (LCD), a flat panel, a solid state display, or a cathode ray tube (CRT). The computer system 5600 may include an input device 5612, such as, but not limited to, a keyboard, a cursor control device 5614, such as, but not limited to, a mouse, a disk drive unit 5616, a signal generation device 5618, such as, but not limited to, a speaker or remote control, and a network interface device 5620.

The disk drive unit 5616 may include a machine-readable medium 5622 on which is stored one or more sets of instructions 5624, such as, but not limited to, software embodying any one or more of the methodologies or functions described herein, including those methods illustrated above. The instructions 5624 may also reside, completely or at least partially, within the main memory 5604, the static memory 5606, or within the processor 5602, or a combination thereof, during execution thereof by the computer system 5600. The main memory 5604 and the processor 5602 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but are not limited to, distributed processing or component/object distributed processing, parallel processing, or virtual machine processing can also be constructed to implement the methods described herein.

The present disclosure contemplates a machine-readable medium 5622 containing instructions 5624 so that a device connected to the communications network 135, another network, or a combination thereof, can send or receive voice, video or data, and communicate over the communications network 135, another network, or a combination thereof, using the instructions. The instructions 5624 may further be transmitted or received over the communications network 135, another network, or a combination thereof, via the network interface device 5620.

While the machine-readable medium 5622 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

In certain embodiments, FIGS. 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, and 108 provide color versions of FIGS. 2-53 and may be utilized to provide further details relating to the features and/or functionality provided by embodiments of the present disclosure.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

We claim:

1. A system, comprising:
    a memory that stores instructions; and
    a processor that executes the instructions to perform operations, the operations comprising:
        obtaining an image of an anatomy of interest of a subject;
        rendering, by utilizing volume rendering, an enhanced version of the image of the anatomy of interest on a user interface;
        generating a plan for implanting an implant onto the anatomy of interest based on an input including a landmark point for the enhanced version of the image of the anatomy of interest;
        facilitating, via an implant position control, implant positioning for the plan for the implant, wherein the implant positioning is optimized based on bone surface geometry and dense bone contact with the implant indicated via the enhanced version of the image rendered by utilizing the volume rendering;
        conducting a registration process to match the anatomy of interest of the subject with the enhanced version of the image of the anatomy of interest in the plan; and
        facilitating, by utilizing the plan and based on the match conducted via the registration process, performance of a surgical procedure for implanting the implant onto the anatomy of interest of the subject.

2. The system of claim 1, wherein the operations further comprise processing the image of the anatomy of the subject by utilizing an image filter to reduce noise and eliminate portions of the anatomy that are not required for the plan, the surgical procedure, or a combination thereof.

3. The system of claim 1, wherein the operations further comprise registering the plan to the anatomy of the subject using the landmark point defined in the enhanced version of the image of the anatomy of interest.

4. The system of claim 1, wherein the operations further comprise refining the registration process by extracting bone surface information from the enhanced version of the image and positioning the bone surface information to match a physical bone surface in the anatomy.

5. The system of claim 4, wherein the operations further comprise detecting the physical bone surface in the anatomy by tracing a tracked pointer on a bone of the anatomy, scanning the bone surface by utilizing a bone surface detection device comprising an optical or ultrasonic surface detection device, or a combination thereof.

6. The system of claim 1, wherein the operations further comprise suggesting the landmark point based on proportions in the enhanced version of the image of the anatomy of interest, the image of the anatomy of interest of the subject, or a combination thereof.

7. The system of claim 1, wherein the operations further comprise obtaining the image of the anatomy of the subject by utilizing a magnetic resonance imaging device, a computerized tomography device, an x-ray device, an ultrasound device, a smartphone, a camera device, a mobile device, any type of imaging device, or a combination thereof.

8. The system of claim 1, wherein the operations further comprise visually rendering the implant position control in proximity to the enhanced version of the image of the anatomy of interest of the subject on the user interface.

9. The system of claim 1, wherein the operations further comprise updating a corresponding bone cut in the enhanced version of the image of the anatomy as the implant positioning is adjusted in real-time.

10. The system of claim 1, wherein the operations further comprise calculating measurements related to an implant pose of the implant each time the implant positioning is adjusted.

11. The system of claim 1, wherein the operations further comprise storing the implant position relative to the landmark point in the plan for the subject.

12. The system of claim 1, wherein the operations further comprise enabling automatic suggestion of a plurality of landmark points by utilizing an artificial intelligence system, wherein the artificial intelligence system comprises a convolutional neural network, a modular neural network, a recurrent neural network, a self-organizing neural network, a radial basis function neural network, a feed-forward neural network, other neural network, or a combination thereof trained for prediction of points using already marked scans as training data, other artificial intelligence technology, or a combination thereof.

13. The system of claim 12, wherein the operations further comprise utilizing an image set associated with the image of the anatomy of interest as an input into the artificial intelligence system, wherein the operations further comprise generating an output containing locations of the plurality of landmark points, and wherein the operations further comprise displaying the output as a plurality of suggestions for the plurality of landmark points.

14. A method, comprising: obtaining an image of an anatomy of interest of a subject; rendering, by utilizing volume rendering, an enhanced version of the image of the anatomy of interest on a user interface; generating, by utilizing instructions from a memory that are executed by a processor, a plan for implanting an implant onto the anatomy of interest based on an input including a landmark point for the enhanced version of the image of the anatomy of interest; facilitating, via an implant position control, implant positioning for the plan for the implant, wherein the implant positioning is optimized based on bone surface geometry and dense bone contact with the implant indicated via the enhanced version of the image rendered by utilizing the volume rendering; conducting a registration process to match the anatomy of interest of the subject with the enhanced version of the image of the anatomy of interest in the plan; and performing, by utilizing the plan and based on the match conducted via the registration process, a surgical procedure for implanting the implant onto the anatomy of interest of the subject.

15. The method of claim 14, further comprising assigning, when utilizing the volume rendering, a scale of visible colors and opacity to variable pixel values, variable voxel values, or both, in the image of the anatomy of the subject.

16. The method of claim 14, further comprising optimizing a position of the implant based on a bone geometry, bone structure, a bone characteristic, information relating to a maximum support by bone contact with the implant, anatomy surrounding the anatomy of interest, anatomy in proximity to the anatomy of interest, a type of the implant, a type of approach to be utilized for implantation, information associated with sides of the anatomy of interest, bone density information, bone surface information, information associated with the subject, or a combination thereof.

17. The method of claim 14, further comprising refining the registration process after initial point-based registration.

18. The method of claim 14, further comprising enabling a surgical navigation system, a robot, or a combination thereof, to utilize the plan to guide the cutting of a bone associated with the anatomy, accurately position a component of the implant, or a combination thereof.

19. The method of claim 14, further comprising generating the plan and conducting the registration process without utilizing bone contouring, a digital surface model, or a combination thereof.

20. A non-transitory computer-readable device comprising instructions, which, when loaded and executed by a processor, cause the processor to perform operations, the operations comprising: obtaining an image of an anatomy of interest of a subject; rendering, by utilizing volume rendering, an enhanced version of the image of the anatomy of interest on a user interface; generating a plan for implanting an implant onto the anatomy of interest based on an input including a landmark for the enhanced version of the image of the anatomy of interest; facilitating, via an implant position control, implant positioning for the plan for the implant, wherein the implant positioning is optimized based on bone surface geometry and dense bone contact with the implant indicated via the enhanced version of the image rendered by utilizing the volume rendering; conducting a registration process to match the anatomy of interest of the subject with the enhanced version of the image of the anatomy of interest in the plan; and performing, by utilizing the plan and based on the match conducted via the registration process, a surgical procedure for implanting the implant onto the anatomy of interest of the subject.

* * * * *